United States Patent

Amano et al.

[11] Patent Number: 6,095,984
[45] Date of Patent: Aug. 1, 2000

[54] ARRHYTHMIA DETECTING APPARATUS

[75] Inventors: Kazuhiko Amano, Suwa; Kazuo Uebaba, Yokohama; Hitoshi Ishiyama, Toride, all of Japan

[73] Assignee: Seiko Epson Corporation, Tokyo, Japan

[21] Appl. No.: 08/981,349

[22] PCT Filed: Apr. 17, 1997

[86] PCT No.: PCT/JP97/01322

§ 371 Date: Apr. 6, 1998

§ 102(e) Date: Apr. 6, 1998

[87] PCT Pub. No.: WO97/38626

PCT Pub. Date: Oct. 23, 1997

[30] Foreign Application Priority Data

Apr. 17, 1996 [JP] Japan .................................. 8-095731
Mar. 10, 1997 [JP] Japan .................................. 9-055263

[51] Int. Cl.[7] .................................. A61B 5/04; A61B 5/02
[52] U.S. Cl. ........................ 600/500; 600/481; 600/513; 600/515
[58] Field of Search .................................. 600/515, 513, 600/500, 509, 481

[56] References Cited

U.S. PATENT DOCUMENTS

| 3,996,928 | 12/1976 | Marx .................................. 600/515 |
| 4,261,370 | 4/1981 | Von Nettelhorst .................................. 600/481 |
| 4,338,950 | 7/1982 | Barlow, Jr. et al. . |
| 5,749,366 | 5/1998 | Odagiri et al. .................................. 600/481 |
| 5,776,070 | 7/1998 | Kitazawa et al. .................................. 600/483 |

FOREIGN PATENT DOCUMENTS

| 0 729 726 | 9/1996 | European Pat. Off. . |
| 60-135029 | 7/1985 | Japan . |
| 2-289230 | 11/1990 | Japan . |
| 4-285530 | 10/1992 | Japan . |
| 7-227383 | 8/1995 | Japan . |

Primary Examiner—Cary O'Connor
Assistant Examiner—Navin Natnithithadha

[57] ABSTRACT

The arrhythmia detecting apparatus of the present invention is provided with a pulse wave detecting means which non-invasively detects the pulse waveform, and an arrhythmia detecting means which detects arrhythmia by monitoring changes in the pulse waveform detected by the pulse wave detecting means. The arrhythmia detection means has a decision element which determines that arrhythmia has occurred when there is an interruption in the continuity of this change. Methods employed for investigating the continuity of change in the pulse waveform include a time domain method employing pulse wave interval values, and a frequency domain method in which frequency analysis (FFT or wavelet transformation) is carried out on the pulse waveform, with continuity studied based on the results of this analysis. As a result of this design, it is possible to detect arrhythmia by means of a simpler structure and easier operations as compared to an electrocardiogram and so on. Further, it is also acceptable to provide a body motion detecting means, and to determine continuity of change for a pulse wave component after the body motion component detected by the aforementioned means has been removed therefrom. In this case, since it is possible to remove the body motion component from the pulse waveform, arrhythmia can be detected even more accurately throughout the course of daily activities.

37 Claims, 43 Drawing Sheets

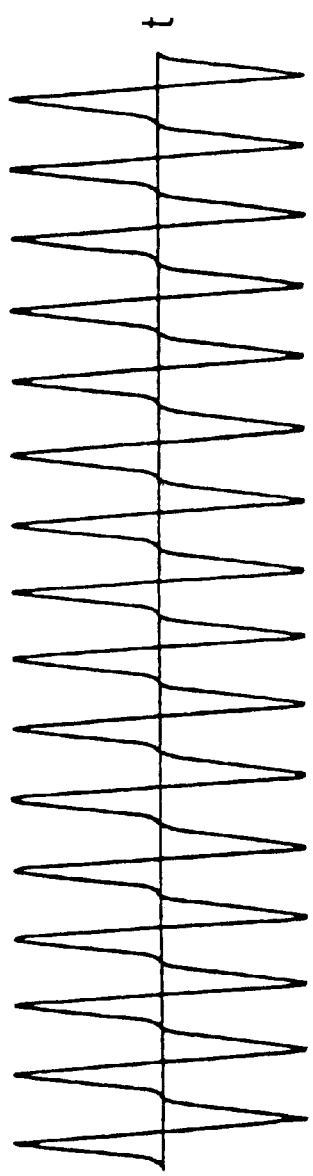
FIG. 9A ORIGINAL WAVEFORM
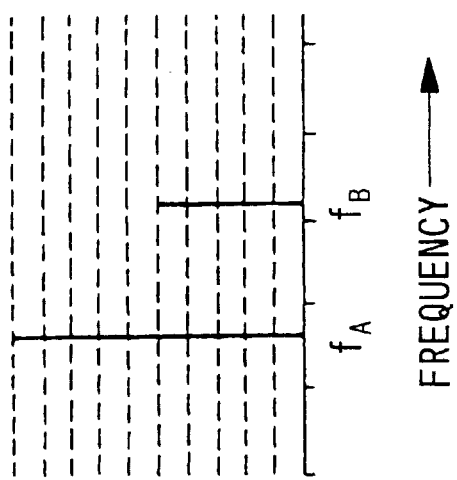
FIG. 9B

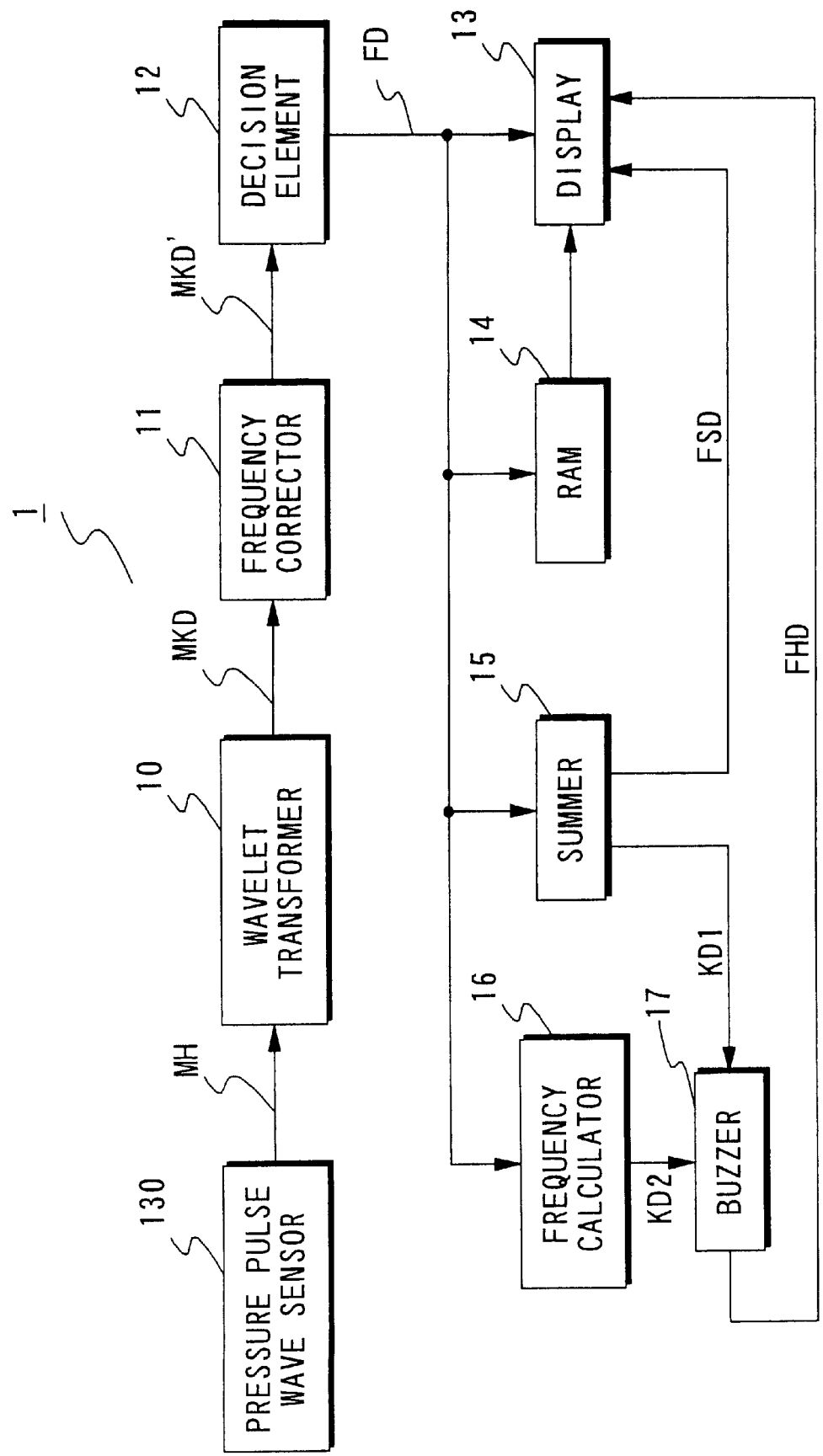

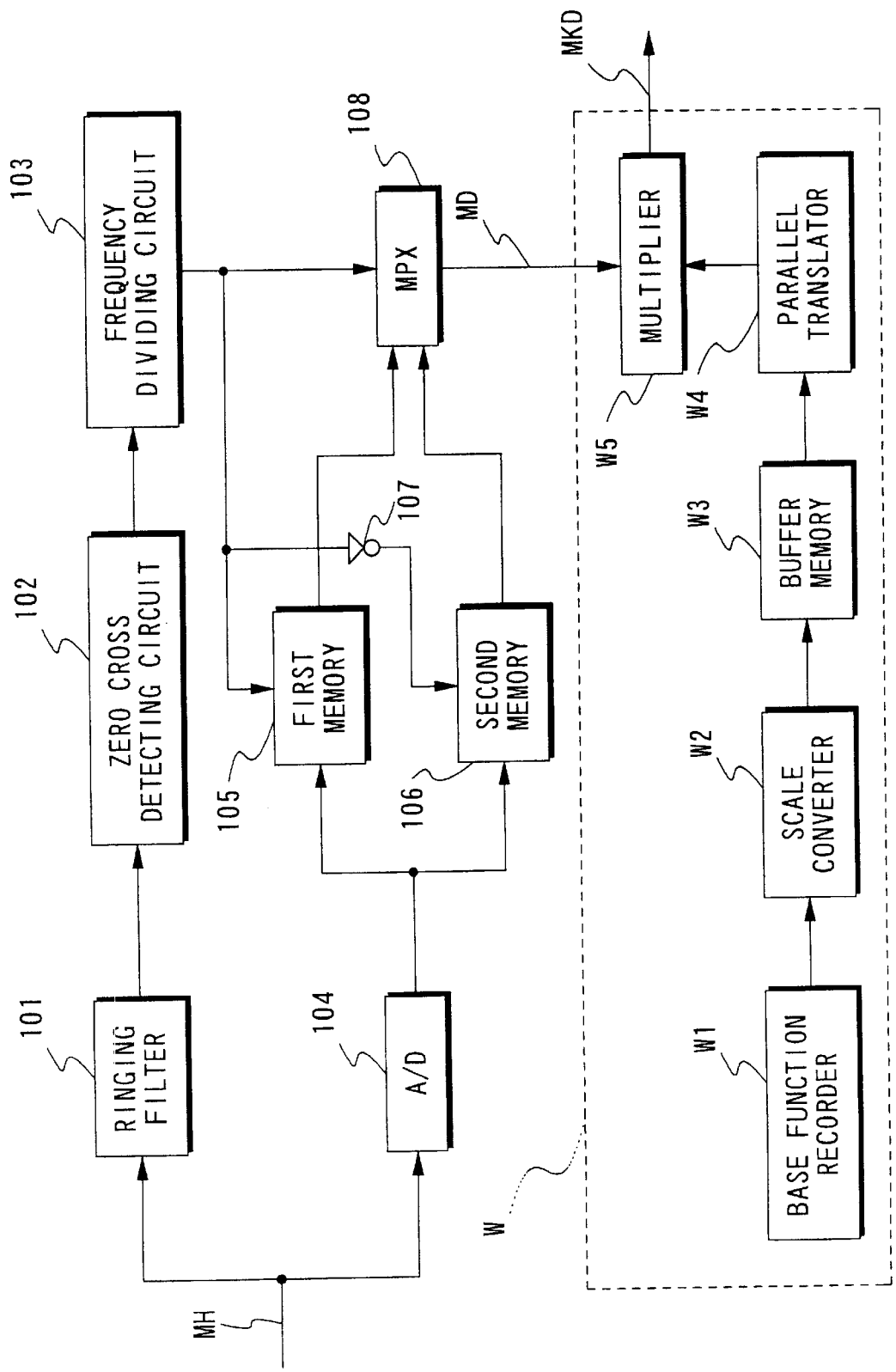

FIG. 25A MH 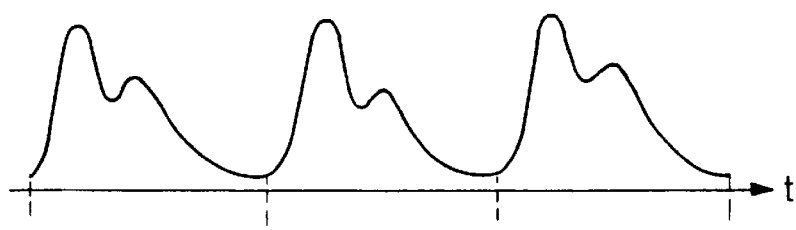

FIG. 25D CS 

FIG. 28A MH
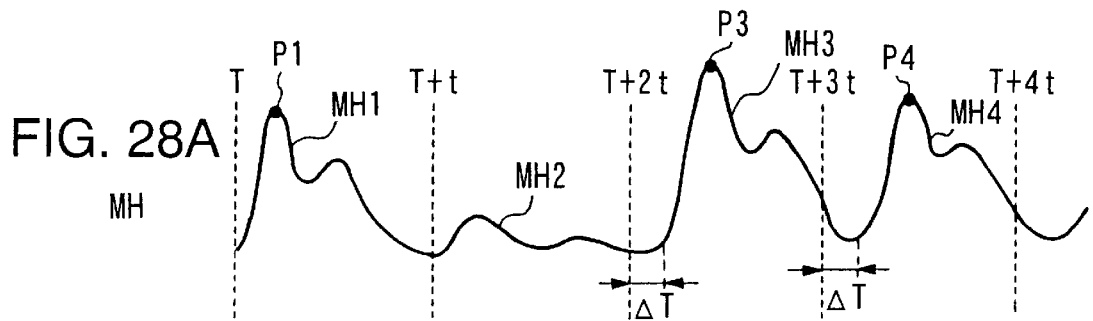
FIG. 28B
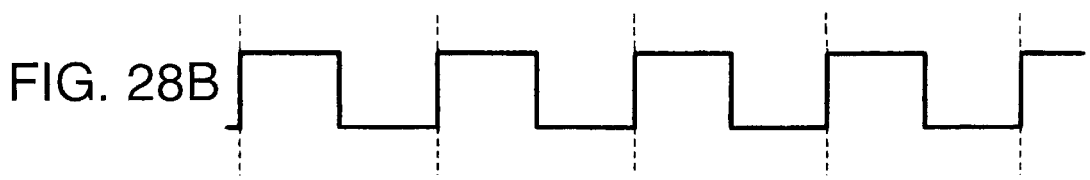
FIG. 28C MKD'
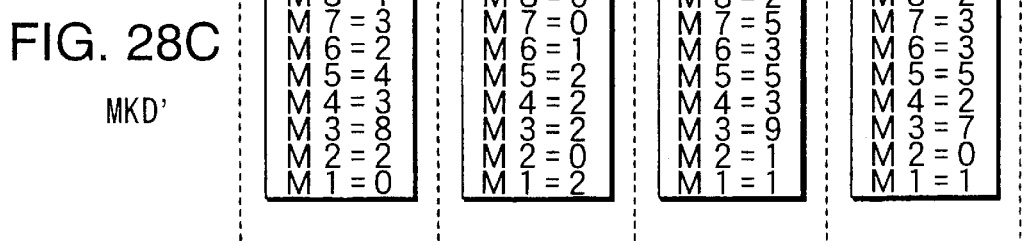
FIG. 28D
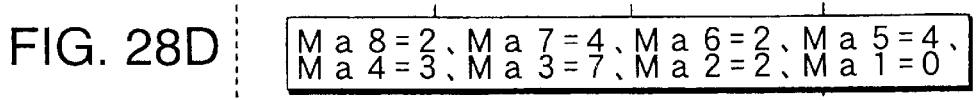
FIG. 28E QD1=0.4 QD2=2.5 QD3=0.8 QD4=0.5
FIG. 28F
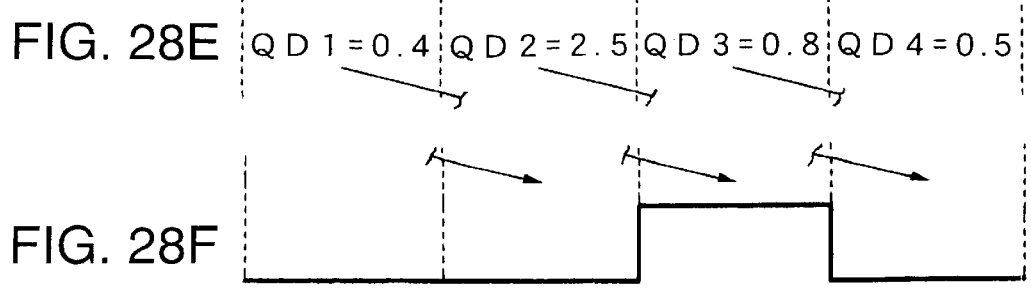

MH

TH

MH' f=1.3Hz

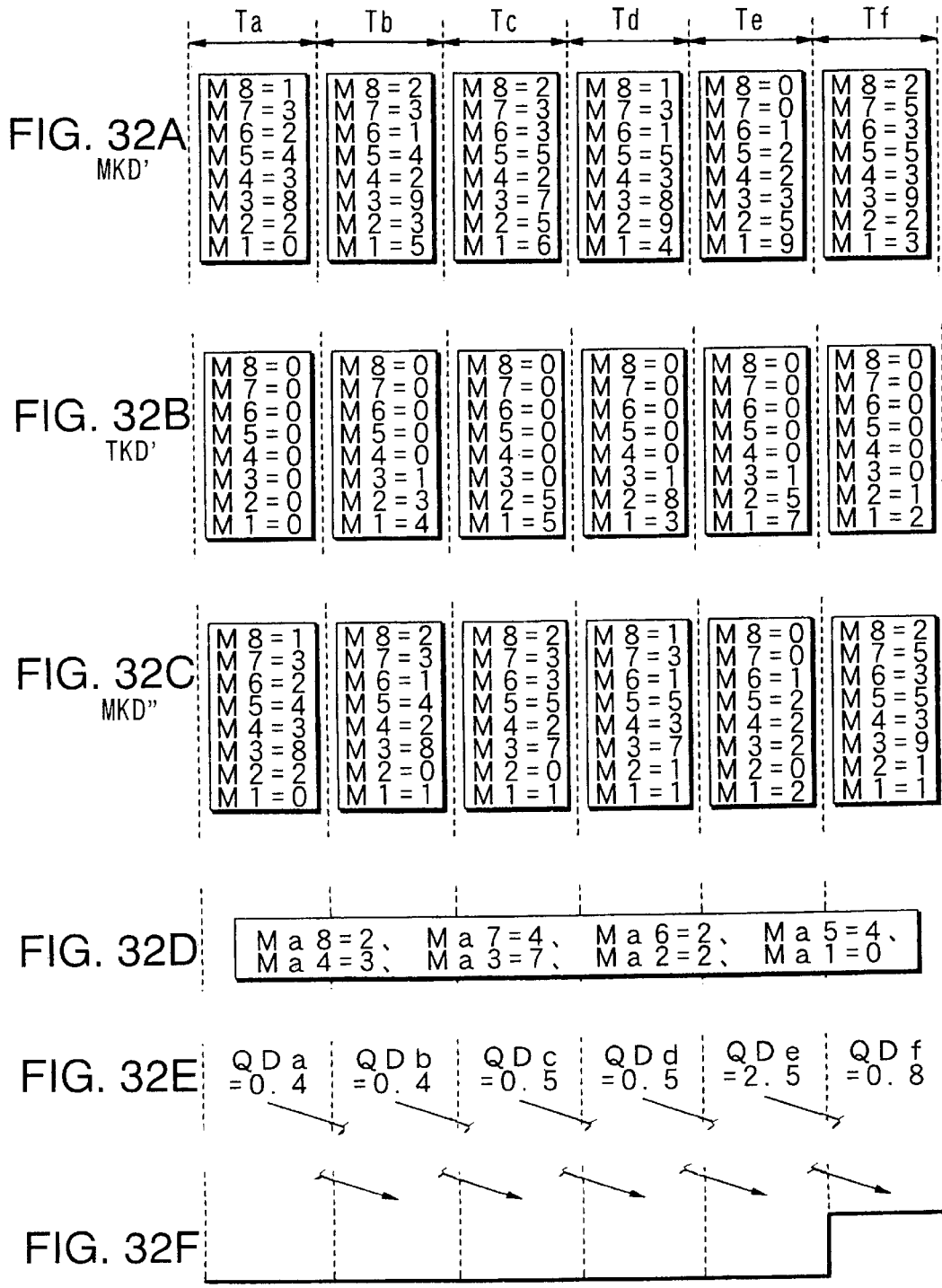

FIG. 44

| 1997/04/01 10:28:15 |
| 1997/04/01 10:59:21 |
| 19997/04/01 11:40:18 |
| ⋮ |

ARRHYTHMIA DETECTING APPARATUS

BACKGROUND OF THE INVENTION

1. Field of the Invention

The present invention relates to an arrhythmia detecting apparatus suitable for detecting arrhythmia at rest and during daily activity, from the pulse.

2. Description of the Related Art

The pulse generated by the contraction of the heart may be obtained in the form of a pulse wave (pulse waveform). This pulse waveform can be broadly separated into a "principal wave", which arises from the contraction of the heart which causes blood to be sent into the arteries, and a "dicrotic wave", which derives from closure of the heart valve. In a healthy individual, there is a regular repetition in the contraction of the heart, such that the pulse waveform exhibits a constant rhythm.

However, when the heart is weak due to an abnormality in the circulatory system, an arrhythmic pulse may occur. While these types of disorders in the pulse (hereinafter, referred to as "arrhythmia") can be caused by smoking, they are also frequently seen in cardiac diseases such as cardiac valve disease, myocardial infarction, cardiomyopathy and so on. Accordingly, arrhythmia detection would be useful for the diagnosis of some abnormalities in the circulatory system.

The danger of bradycardia (in which the pulse rate is less than 40 beats/min), caused by symptoms of complete atrio-ventricular block or Adums-Stokes syndrome, is well known. Moreover, it is also known that symptoms of sick sinus syndrome cause bradycardia or tachycardia (in which the pulse rate is 150 beats/min or more). Further, extrasystole can cause intermittent pulse (arrhythmia), so that its occurrence during exercise may be considered quite dangerous. Thus, in view of these circumstances, considerable focus has been placed on detection of arrhythmia.

It has been the conventional to detect arrhythmia such as described above by employing an electrocardiogram in which electrodes are attached to the subject's chest, and an electrocardiac potential is detected via the electrodes.

An electrocardiography is a large device, and requires the attachment of electrodes to the subject. Accordingly, the subject's movements are restrained since he cannot leave the examination room for the duration of procedure. While portable electrocardiogram recording devices have been developed in recent years, these too are problematic since they are difficult to use, and do not enable a person without specialized knowledge to detect arrhythmia on his own easily. In other words, until now, it has not been possible to detect accurately arrhythmias during in one's normal daily activities.

SUMMARY OF THE INVENTION

The present invention was conceived in consideration of the above-described circumstances, and has as its objective the provision of a portable arrhythmia detecting apparatus capable of accurately detecting arrhythmia by means of a simple operation which can be performed during the course of normal daily activities.

In order to resolve the problems discussed above, the present invention is basically provided with:

a pulse wave detecting means which non-invasively detects the pulse waveform in the body;

a body motion component excluding means which excludes the body motion component from the pulse waveform detected by the pulse wave detecting means; and a notifying means which provides notice of information showing the pure pulse waveform, which is the waveform obtained after the body motion component excluding means has excluded the body motion component.

Alternatively, the arrhythmia detecting apparatus according to the present invention may be provided with:

a pulse wave detecting means which non-invasively detects the pulse waveform in the body;

a body motion component excluding means which excludes the body motion component from the pulse waveform detected by the pulse wave detecting means;

an arrhythmia detecting apparatus which detects arrhythmia by monitoring changes in the pure pulse waveform obtained after the body motion component excluding means has excluded the body motion component; and a notifying means which provides notice of the results of the detection by the arrhythmia detecting means.

The above-described structure permits arrhythmia to be detected based on pulse waveforms which can be obtained in a non-invasive manner. Thus, arrhythmia can be detected by means of a simple operation, without requiring the attachment of electrodes to the test subject's chest. Moreover, the design of the arrhythmia detecting apparatus according to the present invention is simpler and more compact than an electrocardiograph, making it possible to realize an arrhythmia detecting apparatus with excellent portability. Additionally, it is noted here that while the pulse waveform detected by the pulse wave detecting means may be considered to include a body motion component which arise from daily activity, it is an easy matter to distinguish between the body motion component and the pulse wave component provided that the body motion is within the normal daily range. Accordingly, it is possible to obtain a pure pulse waveform, thereby allowing accurate detection of arrhythmia during the course of daily activities. Moreover, it goes without saying that by providing notice of information showing the pure pulse waveform, the individual thus notified is made aware of the presence or absence of arrhythmia.

Moreover, if a body motion detecting means which detects body motion and outputs a body motion waveform is provided, and changes in the pulse wave component obtained after excluding the body motion component from the pulse waveform are monitored, then it is possible to cancel out this body motion component. Therefore, it is possible to accurately detect arrhythmia even when the subject is exercising.

Further, the presence or absence of continuity over a time or frequency domain may also be investigated. When checking continuity over a time domain, the difference between a reference value and the pulse wave interval is monitored. However, in order to more accurately detect arrhythmia, it is also acceptable to update the pulse wave interval.

In the case where checking continuity over a frequency domain, arrhythmia is detected by carrying out frequency analysis on the waveform, and employing the result which corresponds to the pulse wave component. In this case, it is also acceptable to more accurately detect arrhythmia by changing the frequency region on which frequency analysis is performed, in response to the body's state of activity. Moreover, it is also acceptable to carry out detection of arrhythmia only when there is constancy in the activity, so that arrhythmia detection is carried out only during regular exercise (running or other intense exercise, for example). With respect to the frequency analysis method, FFT (fast Fourier transform), wavelet transformation, or another method may be suitably employed. In the case of FFT, an appropriate range of variation is first estimated for the pulse frequency. A determination that arrhythmia has occurred is then made if a frequency spectrum projecting into the estimated range of change is not present in the FFT results.

When employing wavelet transformation, the continuity of the pulse wave analysis data obtained by performing wavelet transformation on the pulse waveform is analyzed in each frequency region. A determination that arrhythmia has occurred is made if an abnormal portion is detected. In this case, it is also acceptable to correct the pulse wave analysis data based on the various corresponding frequencies so that the power density per frequency becomes constant. Corrected pulse wave data is thereby generated, and the continuity of the corrected pulse wave data is analyzed in each frequency region. If an abnormal portion is detected, then a determination is made that arrhythmia has occurred.

Wavelet transformation may also be performed on the pulse waveform and the body motion waveform, respectively, to obtain pulse wave analysis data and body motion analysis data. Then, an analysis of continuity may be carried out on the result obtained after subtracting the body motion analysis data from the pulse wave analysis data. It is of course also acceptable. to carry out the aforementioned subtraction after correcting the wavelet transformation results so that the power density per frequency becomes constant, or to carry out correction after the subtraction operation. In addition, as another method for excluding the body motion component from the pulse waveform, a method may be employed in which the frequency component corresponding to body motion is excluded from the pulse wave analysis data or the pulse wave correction data. In addition, wavelet transformation may be carried out in synchronization with the period of the pulse waveform.

When a decision is made that arrhythmia has occurred, the user may be notified of this fact, and the time of the event may be recorded. It is also acceptable to provide notice to the user after associating the information (a histogram, for example) corresponding to the recorded time of an arrhythmia event with physiological rhythms in the body. It is also acceptable to calculate the arrhythmia frequency information by calculating the number of times that a determination of arrhythmia is made within a specified period of time. In this case, notice is provided when this arrhythmia frequency information exceeds a specific value determined in advance. It is also acceptable to add the number of times that an arrhythmia determination has been made, to generate arrhythmia sum information. In this case, notice is then provided when the arrhythmia sum information exceeds a specific value determined in advance. In addition, it is also acceptable to provide notice when both the arrhythmia frequency information and the arrhythmia sum information exceed the respective specific values determined in advance therefor, or, alternatively, when at least one of these exceeds the specific value determined in advance therefor. By means of these various designs, it is thereby possible for the user to be aware of his own physical condition.

Arrhythmia detection processing and notice processing may be carried out in parallel. The pulse wave detecting means may be composed of a pressure pulse wave sensor which employs pressure to detect the arterial pulse. Alternatively, the pulse wave detecting means may be designed so as to receive the light reflected when the detection site on the body is irradiated with light having a wavelength of 300 to 700 nm, and detect the received light signal as a pulse waveform. It is also acceptable that the pulse wave detecting means be designed to receive transmitted light when the detection site is irradiated with light having a wavelength of 600 to 1000 nm, and detect the received light signal as the pulse waveform.

BRIEF DESCRIPTION OF THE FIGURES

FIG. 9A shows an example of the signal obtained by adding frequency $f_A$ and frequency $f_B$. FIG. 9B is a graph showing an example of the result obtained after performing FFT on the aforementioned added signal.

FIG. 23 is a block diagram showing the electrical structure of the arrhythmia detecting apparatus according to this embodiment.

FIG. 24 is a block diagram showing the detailed structure of the wavelet transform element according to this embodiment.

FIGS. 25A, 25B, 25C and 25D are timing charts for the wavelet transform element according to this embodiment.

FIGS. 28A, 28B, 28C, 28D, 28E and 28F are timing charts for explaining the operation of this embodiment.

FIGS. 32A, 32B, 32C, 32D, 32E and 32F are timing charts for explaining the operation of this same embodiment.

FIG. 44 is a figure showing an example of the time stamp which is recorded in the present invention.

DESCRIPTION OF THE PREFERRED EMBODIMENTS

Preferred embodiments of the present invention will now be explained with reference given to the figures.

Before explaining the preferred embodiments of the present invention, however, a discussion will first be made of the basic technical concepts of the present invention.

Ordinarily, there is a difference between exercising and non-exercising pulse rate. In either case, however, provided the individual is healthy, it is unusual for the pulse to fluctuate sharply. Rather, the change over time in the pulse waveform is continuous (regular). In contrast, while various types of pulse waveforms may characterize an arrhythmia, in all cases, the continuity of change is disrupted, or cut. Accordingly, by detecting irregular change in the pulse waveform, it is possible to detect the occurrence of arrhythmia. This fact comprises the basic technical concept of the present invention.

Figure 1:
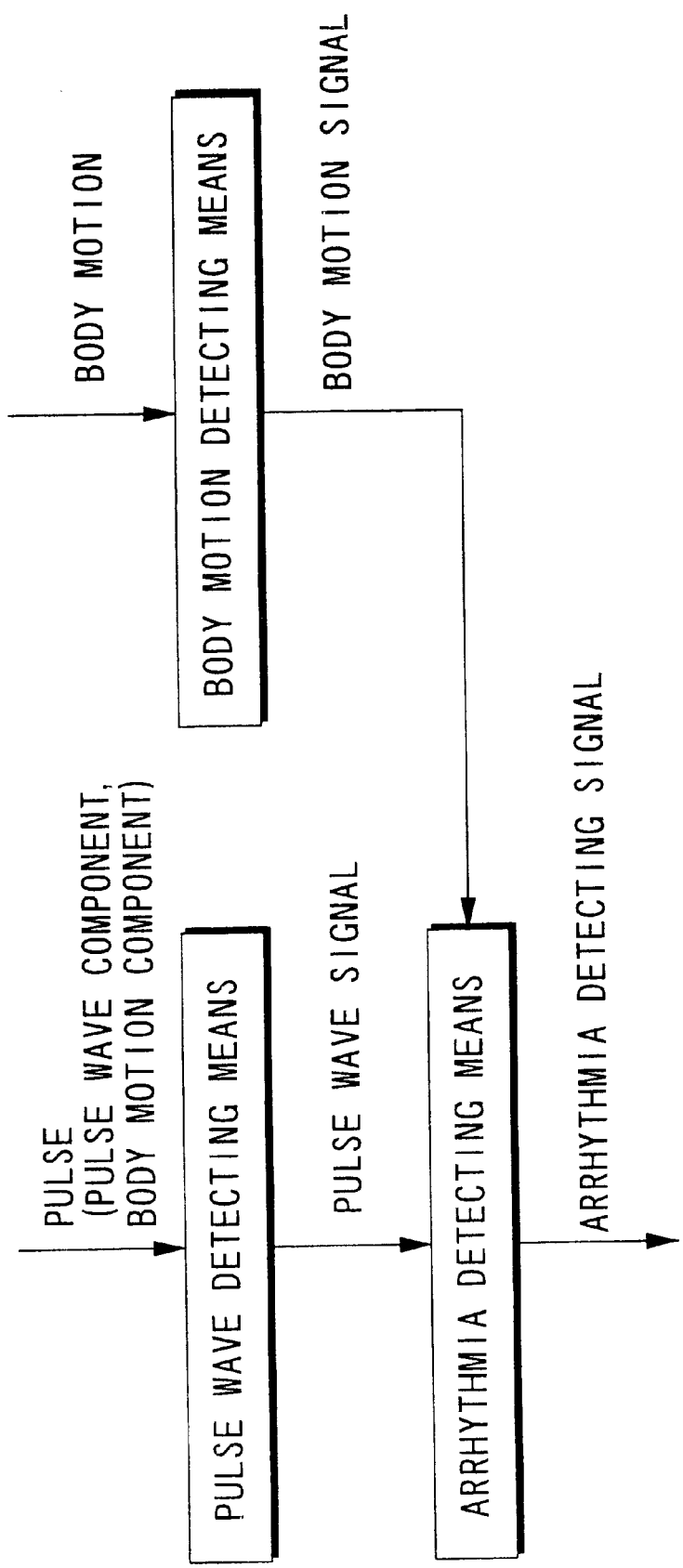
FIG. 1 is a block diagram showing an overview of the structure of an arrhythmia detecting apparatus founded on the basic technical concept of the present invention.

FIG. 1 shows an overview of the structure of an arrhythmia detecting apparatus based on this technical concept. The arrhythmia detecting apparatus in this figure is provided with a pulse wave detecting means which detects the pulse wave in a non-invasive manner and outputs a pulse wave signal (pulse waveform); a body motion detecting means which detects body motion and outputs a body motion signal (body motion waveform); and an arrhythmia detecting means which detects the presence or absence of an arrhythmia event based on the pulse wave signal and body motion signal. Body motion exerts an influence on the pulse detected by the pulse wave detecting means. Accordingly, not only the pulse wave component, but also a body motion component, are present in the pulse wave signal which is output from the pulse wave detecting means. Therefore, the arrhythmia detecting means monitors the pure pulse waveform which is expressed as a pulse wave component obtained by removing the body motion component specified by the body motion signal from the pulse wave signal output by the pulse wave detecting means. When an irregular change in this pure pulse waveform is detected, information reporting the occurrence of an arrhythmia (arrhythmia detection signal) is then output.

1. First Embodiment 1-1 Structure of the First Embodiment

Figure 2:
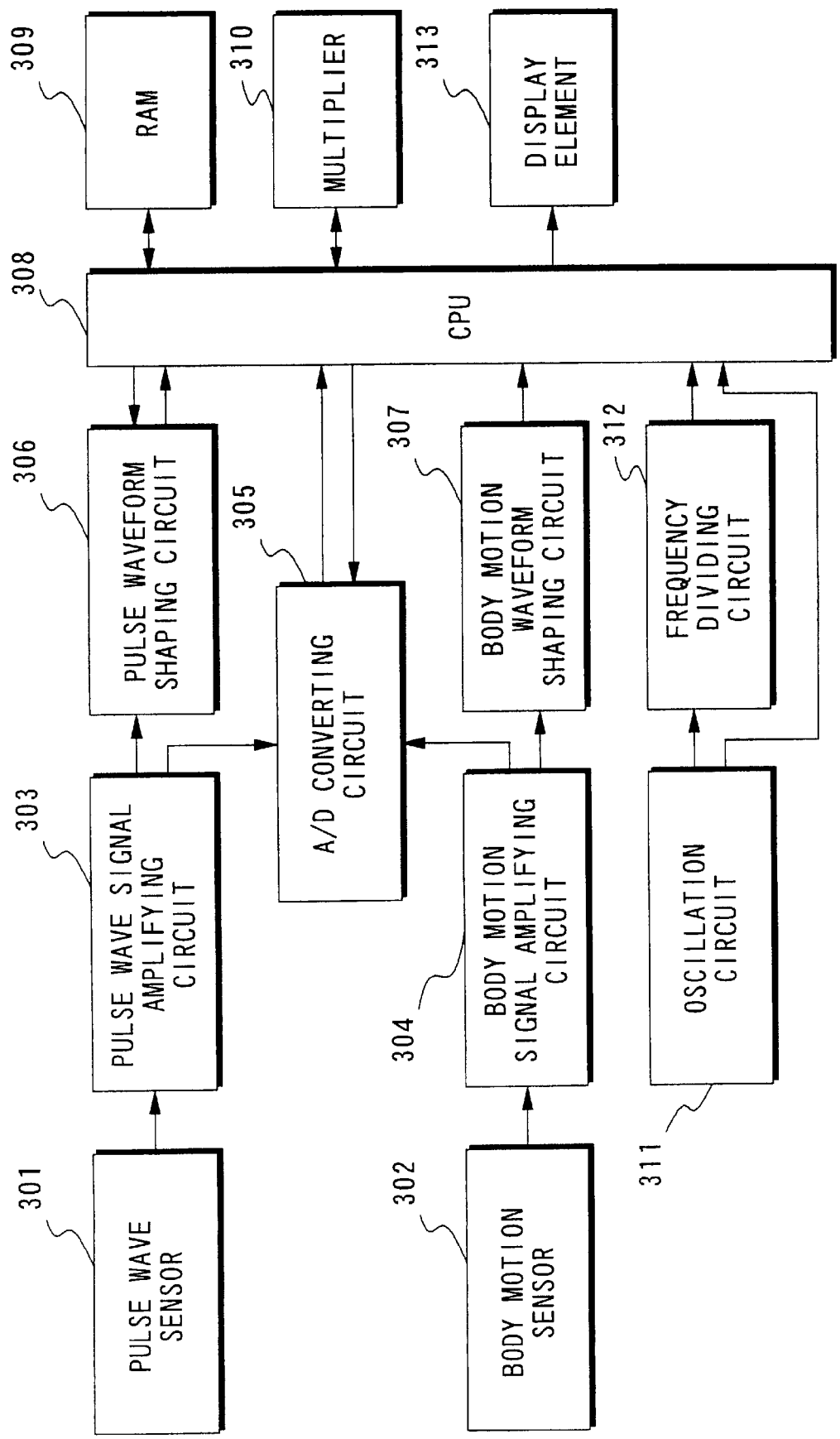
FIG. 2 is a block diagram showing an example of the structure of an arrhythmia detecting apparatus according to the first preferred embodiment of the present invention.

FIG. 2 is a block diagram showing the structure of the arrhythmia detecting apparatus according to the first embodiment of the present invention. The arrhythmia detecting apparatus shown in this figure detects an arrhythmia, counts the number of arrhythmia events, calculates the pulse beat, and the like. In the figure, pulse wave sensor 301 detects pulse in the body, and outputs a pulse wave signal complying with the detected pulse to a pulse wave signal amplifying circuit 303. Pulse wave sensor 301 may be realized by means of a voltage sensor, for example. Body motion sensor 302 detects body motion, and outputs a body motion signal complying with the detected body motion to a body motion signal amplifying circuit 304 (explained below). Body motion sensor 302 may be realized by means of an acceleration sensor, for example.

Pulse wave signal amplifying circuit 303 amplifies the detected pulse wave signal, and outputs the signal to an A/D converting circuit 305 and a pulse waveform shaping circuit 306 (explained below). Body motion signal amplifying circuit 304 amplifies the detected body motion signal, and outputs it to A/D converting circuit 305 and body motion waveform shaping circuit 307 (explained below). A/D converting circuit 305 converts the amplified pulse wave signal and body motion signal from analog signals to digital signals, and outputs the result to CPU 308 explained hereinafter.

Pulse waveform shaping circuit 306 shapes the amplified pulse wave signal and outputs it to CPU 308. Body motion waveform shaping circuit 307 shapes the amplified body motion signal, and outputs it to CPU 308. CPU 308 executes the programs stored in a recording means, such as a ROM, which is not shown in the figures. CPU 308 detects arrhythmia, counts the number of arrhythmia events, calculates pulse rate, and the like, by controlling all parts of the apparatus and carrying out the various operations described below. RAM 309 is employed as the working memory for CPU 308.

Figure 3:
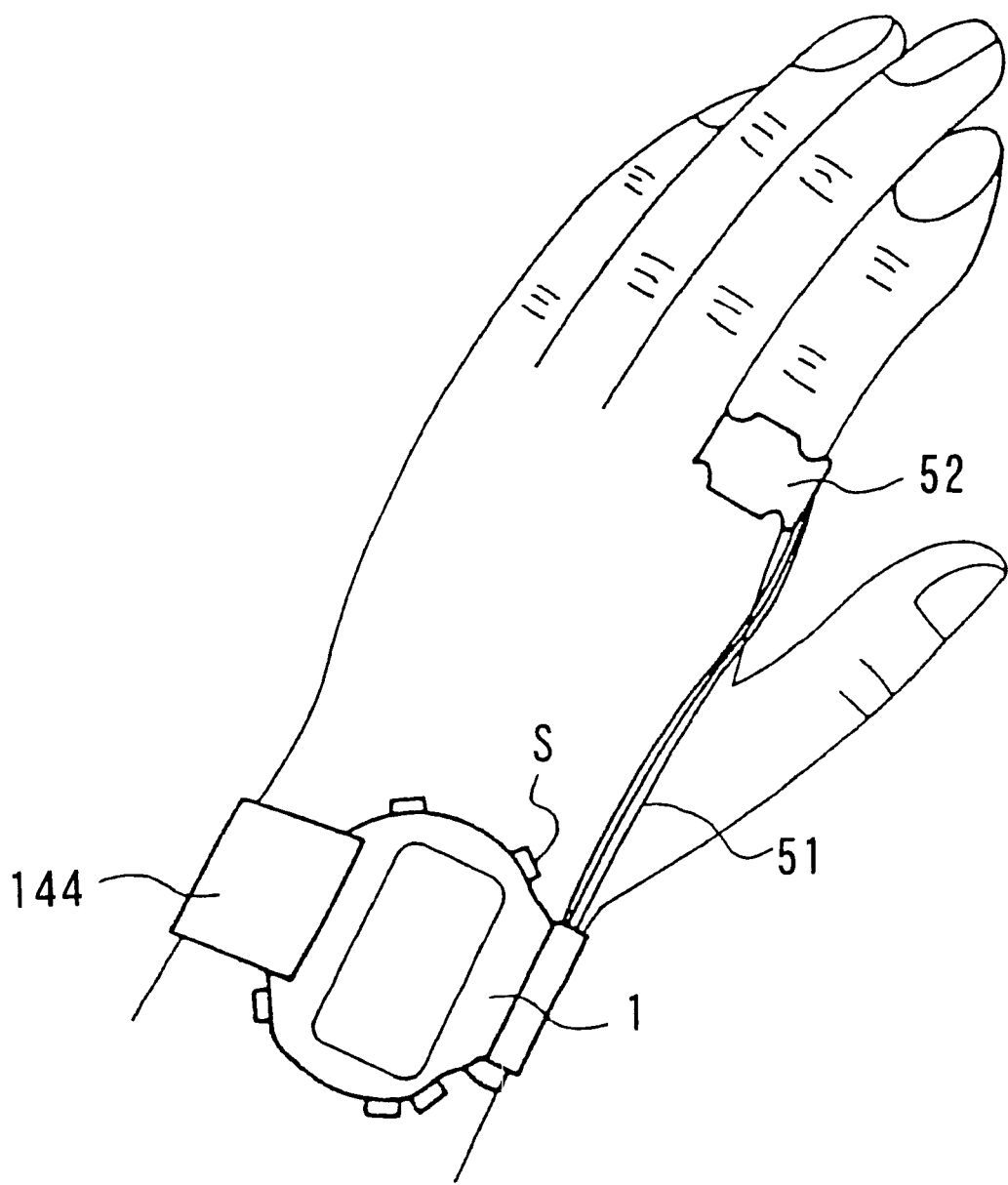
FIG. 3 is a slant view showing an example of the outer appearance of the same apparatus.

311 is an oscillation circuit which generates a fixed period clock pulse. 312 is a frequency dividing circuit which divides the clock pulse generated by oscillation circuit 311, and generates a pulse having a specific frequency. 313 is a display composed of a liquid crystal display device, for displaying the detected result. 310 is an input portion through which the user inputs commands. As shown in FIG. 3. input portion 310 has a plurality of switches which here are represented by setting switch S which is used when determining each of the setting values.

FIG. 3 is a slant view showing an example of the outer appearance of an arrhythmia detecting apparatus of the above-described design. As shown in this figure, a wristwatch design is employed for the arrhythmia detecting apparatus according to this embodiment. In other words, this apparatus not only serves as an arrhythmia detecting apparatus, but also is provided with the functions of a clock which keeps the current time (i.e., real-time clock). The apparatus is designed to be able to execute processing for both of these functions simultaneously. Further, the values for the various settings in each of these functions may be automatically set in response to a signal supplied from the outside via an interface (not shown), or may be set using a mode switch which switches the setting switches S and the mode (setting mode/measuring mode). The clock function in this embodiment is equivalent to that in a conventional digital wristwatch, with the exception that the time keeping results (i.e., time information) are used to record the time at which an arrhythmia event is detected. Accordingly, a description of the structure for realizing the clock function, and the operation thereof, will be omitted here.

In FIG. 3, the main body 1 of the apparatus is attached to the user's wrist by means of a band 144. Pulse wave sensor 301 and body motion sensor 302 (see FIG. 2) are fixed in place to the user's finger by means of a band 52 for holding the sensors in place. The outer appearance of this device is roughly the same as that of the arrhythmia detecting apparatus according to the third and fourth embodiments described below. Accordingly, the device's outer appearance will be described only briefly here, with a more detailed description provided in the discussion of the third embodiment.

1-2. Operation of the First Embodiment

The operation of the arrhythmia detection mode in an arrhythmia detecting apparatus of the above-described design can be broadly divided into two types of operations, with switching between these two modes taking place in response to the state of detection of body motion. Hereinafter, these two modes will be referred to as "first arrhythmia detection operation" and "second arrhythmia detection operation." Separate explanations of each of these follows below.

1-2-1. First Arrhythmia Detecting Operation (1) The user presses a switch indicating the start of measurement. As a result, the apparatus begins detecting the pulse waveform using the method described below under section 1-2-3, "Pulse Waveform Detecting Method".

(2) CPU 308 obtains the average of a specific number of pulse wave intervals immediately following the start of measurement, the pulse wave interval being the interval between the pulse waves which form the pulse waveform. This average value is defined as the initial value of the pulse wave interval. In addition, the reciprocal of this initial value is multiplied by 60, with the resulting value set as the initial value of the pulse rate.

(3) CPU 308 sets the above-described initial pulse wave interval as the reference pulse wave interval I.

(4) CPU 308 obtains the interval value $i_n$ between pulse waves at an optional point in time $t_n$, and divides this interval value $i_n$ by reference pulse wave interval I.

(5) CPU 308 determines that arrhythmia has occurred when the result of the division operation described in (4) above is outside a predetermined allowed range (i.e., outside the acceptable range of variation). CPU 308 then increases the arrhythmia counter, which is realized by means of an internal resistor, and sets the pulse rate from the previous calculation as the current pulse rate. Note that the allowed range which is employed by CPU 308 as the standard for determining whether arrhythmia has occurred is a specified range within the pulse rate region which is centered about the pulse rate obtained in the previous calculation. For example, if the specified range is ±5%, the reference pulse wave interval I is approximately 0.3529 s, and the previously calculated pulse rate is 170 beats/min., then 170×0.05=8.5. Accordingly, the allowed range for pulse rate within the pulse rate region is 161.5~178.5 beats/min. The corresponding range in the time region is therefore: $60/161.5 \approx 0.3715$ and $60/178.5 \approx 0.3361$. In other words: from approximately 0.3361~0.3715 s. Since $0.3361/0.3529 \approx 0.9524$, and $0.3715/0.3529 \approx 1.0527$, the allowed range for the result of the division operation described in (4) above is approximately 0.9524~1.0527.

(6) When the results of the division operation in (4) above are within the aforementioned allowed range, then CPU 308 sets the interval $i_n$ as the reference pulse wave interval I, and sequentially stores intervals $i_n$ in the interval region of RAM 309. CPU 308 also obtains the average of a specific number of intervals most recently stored in the interval region of RAM 309, and multiplies the reciprocal of this average value by 60, to obtain the pulse rate.

(7) CPU 308 uses display 313 to display the pulse rate and the counter number of the arrhythmia counter.

(8) CPU 308 repeats operations (4) through (7) until the user presses a switch indicating the conclusion of measurement. Please note that the counter value of the arrhythmia counter does not have to be displayed in real time; rather the arrhythmia counter value may be displayed for the first time when the user presses the aforementioned switch.

1-2-2. Second Arrhythmia Detecting Operation (1) The user presses a switch indicating the start of measurement. As a result the apparatus begins detecting the pulse waveform using the method described below under section 1-2-3, "Pulse Waveform Detecting Method".

(2) Next, with respect to the pulse waveforms obtained in (1) above, CPU 308 extracts the frequency spectral line lines in which the amplitude (power) exceeds a specific value, from among the surrounding frequency spectral lines (side lobes) which are centered about the frequency spectral line (main lobe) of the fundamental wave of the pulse wave.

(3) CPU 308 determines whether or not the frequency spectral lines extracted in (2) displays irregular values.

Figure 42A:
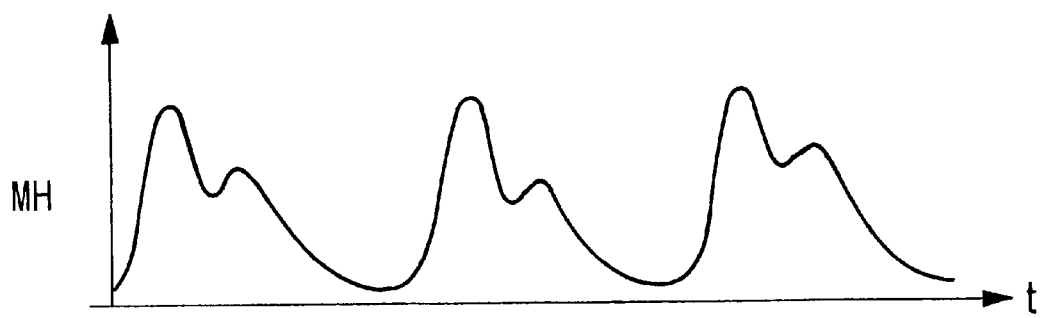
FIGS. 42A and 42B shows the pulse waveform, 42A showing a normal pulse wave and 42B showing an arrhythmia pulse wave.
Figure 42B:
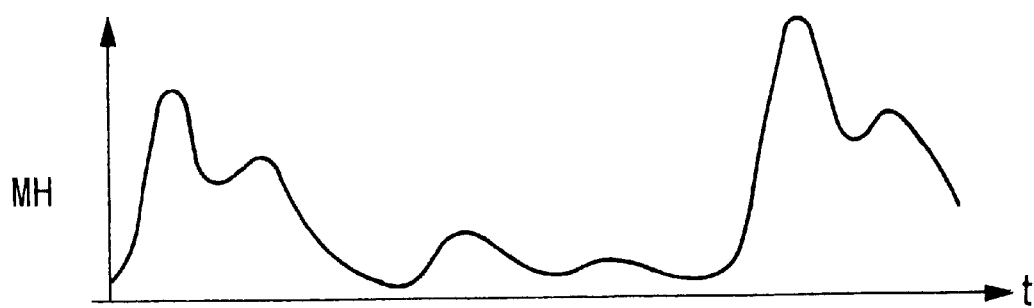

The term "irregular" as used here will now be explained. FIG. 42A shows the radius artery waveform when arrhythmia is not present, while FIG. 42B shows the radius artery waveform when arrhythmia is present. As is clear from a comparison of the two figures, the second pulse waveform in FIG. 42B is flat as a result of the arrhythmia. The fingertip plethysmograph also displays this type of deformation in the pulse waveform when arrhythmia is present. Accordingly, the fingertip plethysmogram is not shown in the figures.

Figure 4:
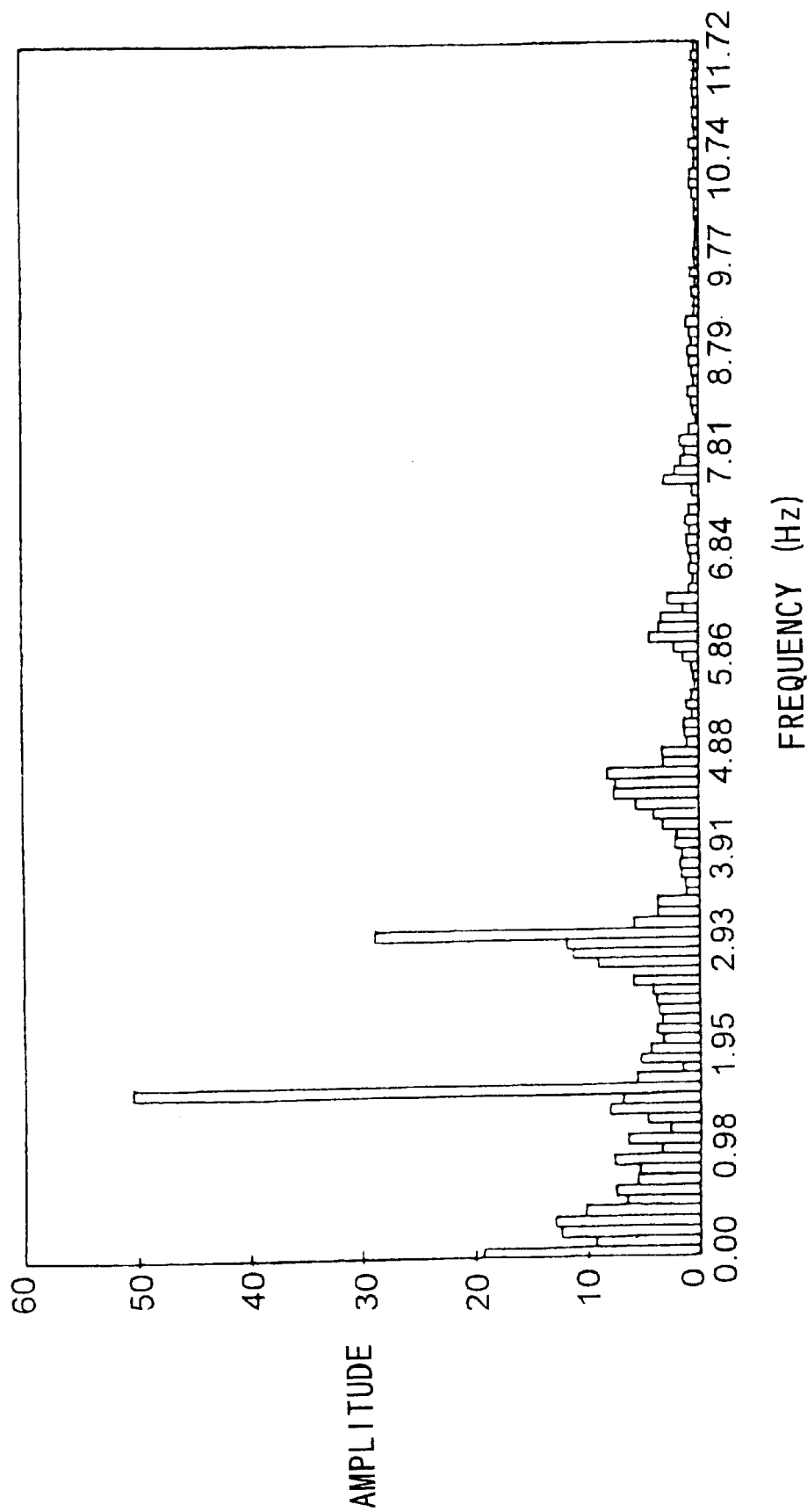
FIG. 4 is a block diagram showing an example of the results of frequency analysis of the fingertip plethysmogram when arrhythmia is not present.
Figure 5:
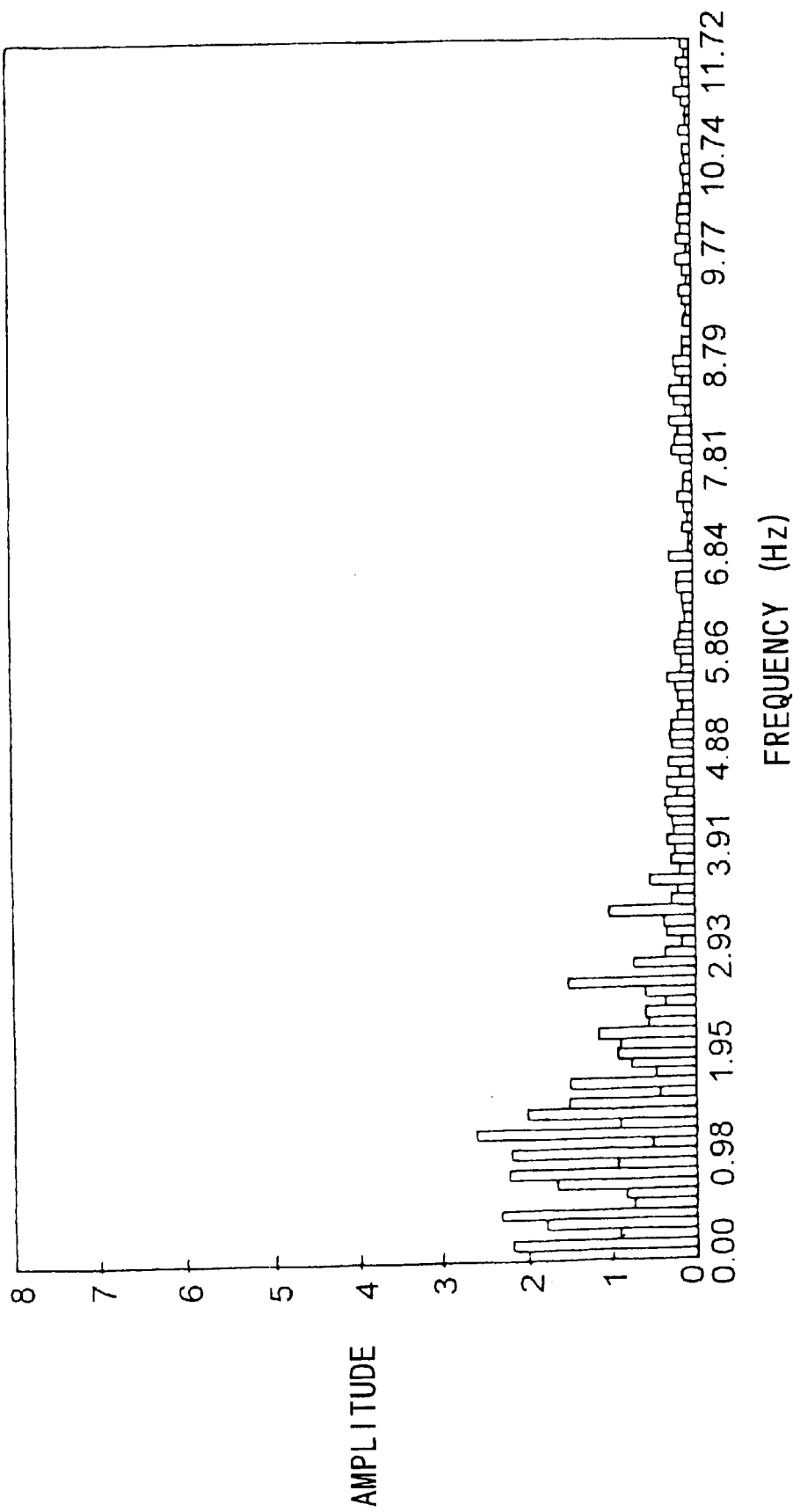
FIG. 5 is a block diagram showing an example of the results of frequency analysis of the fingertip plethysmogram when arrhythmia is present.
Figure 6:
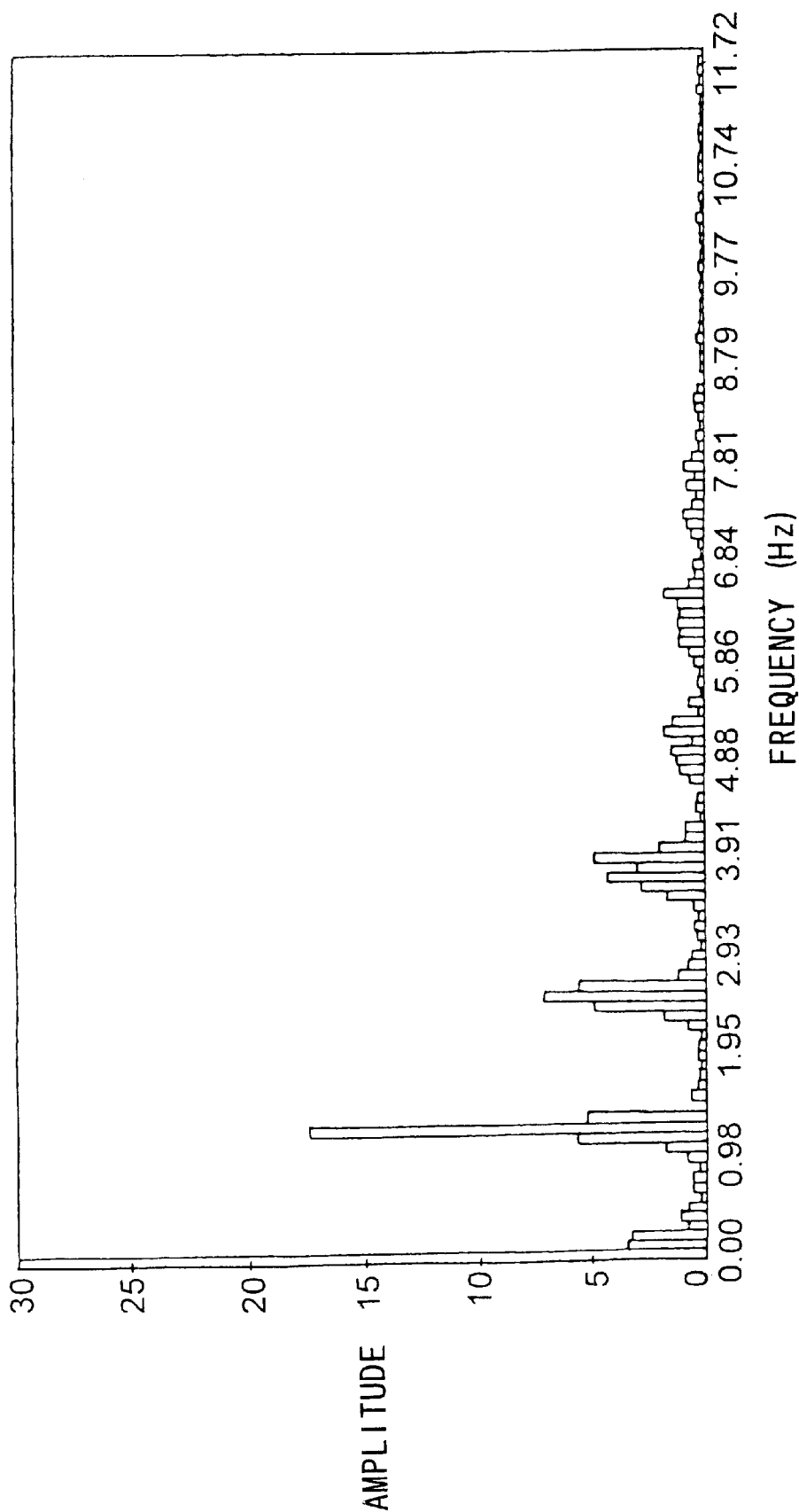
FIG. 6 is a block diagram showing an example of the results of frequency analysis of the radius artery pulse wave when arrhythmia is not present.
Figure 7:
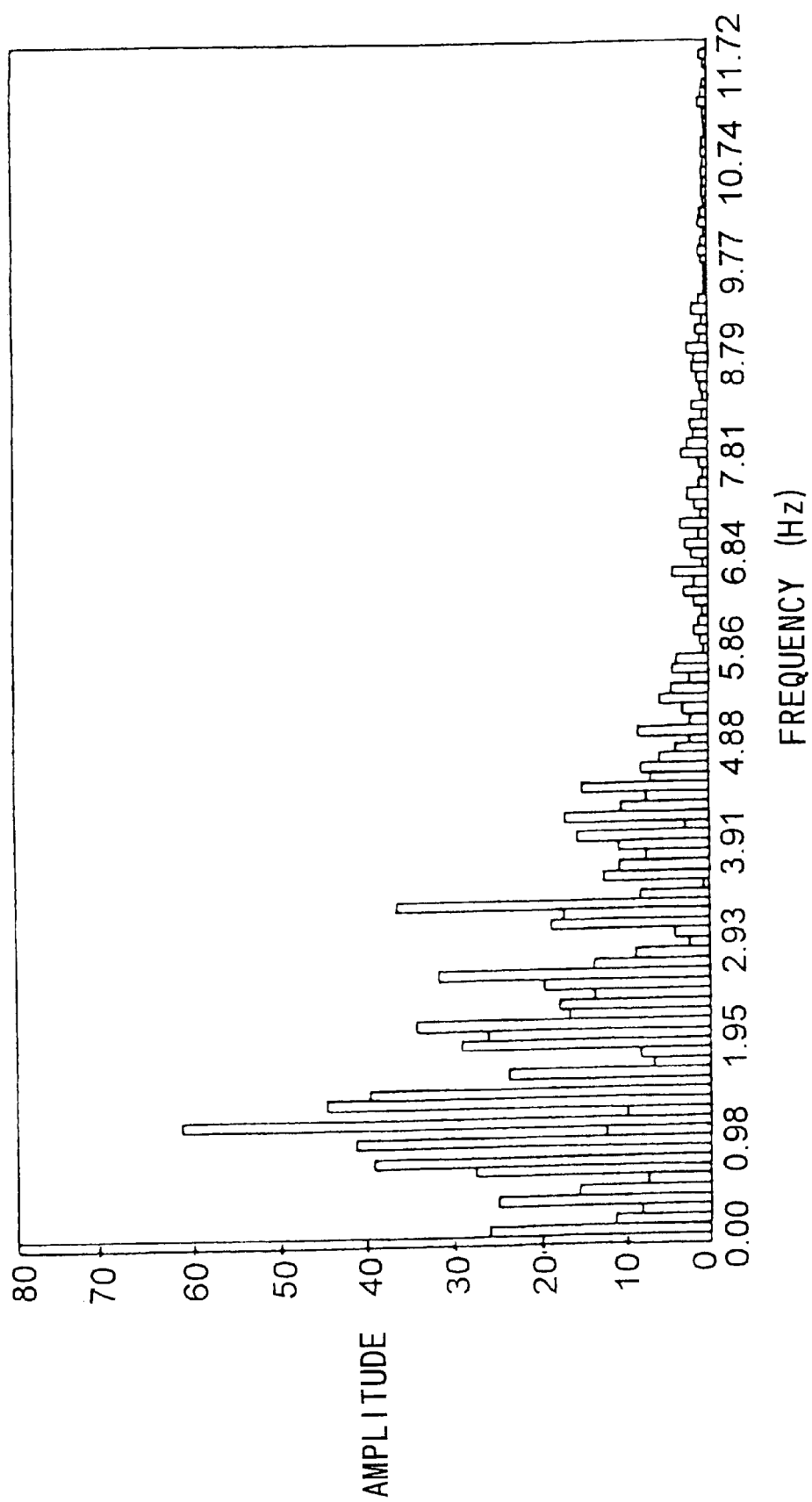
FIG. 7 is a block diagram showing an example of the results of frequency analysis of the radius artery pulse wave when arrhythmia is present.

FIG. 4 is a graph showing an example of the results obtained after carrying out FFT on the fingertip plethysmogram in the case where arrhythmia is not present. FIG. 5 is a graph showing an example of the results obtained after carrying out FFT on the fingertip plethysmogram in the case where arrhythmia is present. FIG. 6 is a graph showing an example of the results obtained after carrying out FFT on the radius artery waveform in the case where arrhythmia is not present. FIG. 7 is a graph showing an example of the results obtained after carrying out FFT on the radius artery waveform in the case where arrhythmia is present. As is clear from these graphs, when a waveform resulting from arrhythmia is present in the pulse waveform during FFT analysis, then there is no rise in the amplitude above the base line, so that the essential effect of FFT frequency analysis is lost. CPU 308 employs this fact to detect the occurrence of arrhythmia.

(4) When an arrhythmia occurrence is detected, CPU 308 displays this fact on display 313, and displays the previously calculated pulse rate without modification as the current pulse rate.

(5) When an arrhythmia occurrence is not detected, CPU 308 calculates the pulse rate by multiplying the spectral line frequency extracted in (2) above by 60, and displaying this pulse rate on display 313.

The processing in (2) and (3) in the second arrhythmia detecting operation are carried out in the following order.

(I) Within the range (generally, 0.6~3.5 Hz) in which the frequency of the fundamental wave of the pulse wave may be present, the frequency spectral line having the maximum power after excluding the body motion component is selected from the spectrums obtained as a result of FFT processing of the pulse wave signal. If the power of this spectral line exceeds a specific value, and if the difference between this spectral line's power and the power of other base lines within the aforementioned range after body motion components have been excluded therefrom is greater than 30%, then this spectral line is extracted as the frequency spectral line of the fundamental wave of the pulse wave.

(II) Taking the extracted frequency spectral line as the main lobe, when the scope of the side lobes thereabout broaden appropriately, and the frequency of the extracted spectral line is within the preconceived allowed range, then CPU 308 determines that arrhythmia is not present.

In this case, determination of whether or not the scope of the aforementioned side lobes spreads appropriately is made by deciding whether the power of the spectral lines on either side of the extracted frequency spectral line is less than 95% of the power of the extracted frequency spectral line. The allowed range for the frequency of the pulse wave's fundamental wave is defined as the range in the frequency domain which corresponds to a specified range which is centered about the previously calculated pulse rate, within the pulse rate domain. For example, if the previously calculated pulse rate was 170 beats/min (frequency of the fundamental wave of the pulse wave: ~2.8333 Hz), and the allowed range in the pulse rate domain is ±5%, then the allowed range in the frequency domain is a range of ±5% centered about the frequency of the fundamental wave of the previous pulse wave (i.e., approximately 2.8333±0.1417 Hz). On the other hand, if the required analysis time for one FFT process is 16 s, then each spectral line is obtained at intervals of 1/16= 0.0625 Hz. In other words, discrete frequency spectral lines such as 2.6875, 2.7500, 2.8750, 2.9375, 3.0000 Hz are obtained in the vicinity of the pulse frequency. Accordingly, by comparing the frequency of the extracted spectral line and the aforementioned discrete frequencies, it is possible to decide whether or not the frequency is within the allowed range. It is of course also acceptable to compare the frequency of the extracted spectral line and the continuous allowed range in the frequency domain (approximately 2.8333±0.1417 Hz), without taking into consideration spectral line discreteness in this way.

However, as is clear from the preceding example, wherein 2.6875<2.8333−0.1417<2.7500 and 2.9375<2.8333+ 0.1417<3.0000, the three spectral lines in the range 2.7500~2.9375 Hz are included in continuous allowed range, while the two spectral lines at 2.6875 Hz and 3.0000 Hz are not included in the continuous allowed ranges. Accordingly, it is possible to conceive of two approaches— one in which these two spectral lines are taken into consideration, and one in which they are not. In order to actively avoid incorrect detection of a normal pulse as an arrhythmia in this embodiment, however, the former approach is employed. Therefore, in this embodiment, CPU 308 determines that arrhythmia has not occurred in the case where the frequency of the extracted spectral line is 2.6875, 2.7500, 2.8750, 2.9375 or 3.0000 Hz.

1-2-3. Pulse Waveform Detecting Method

Figure 8:
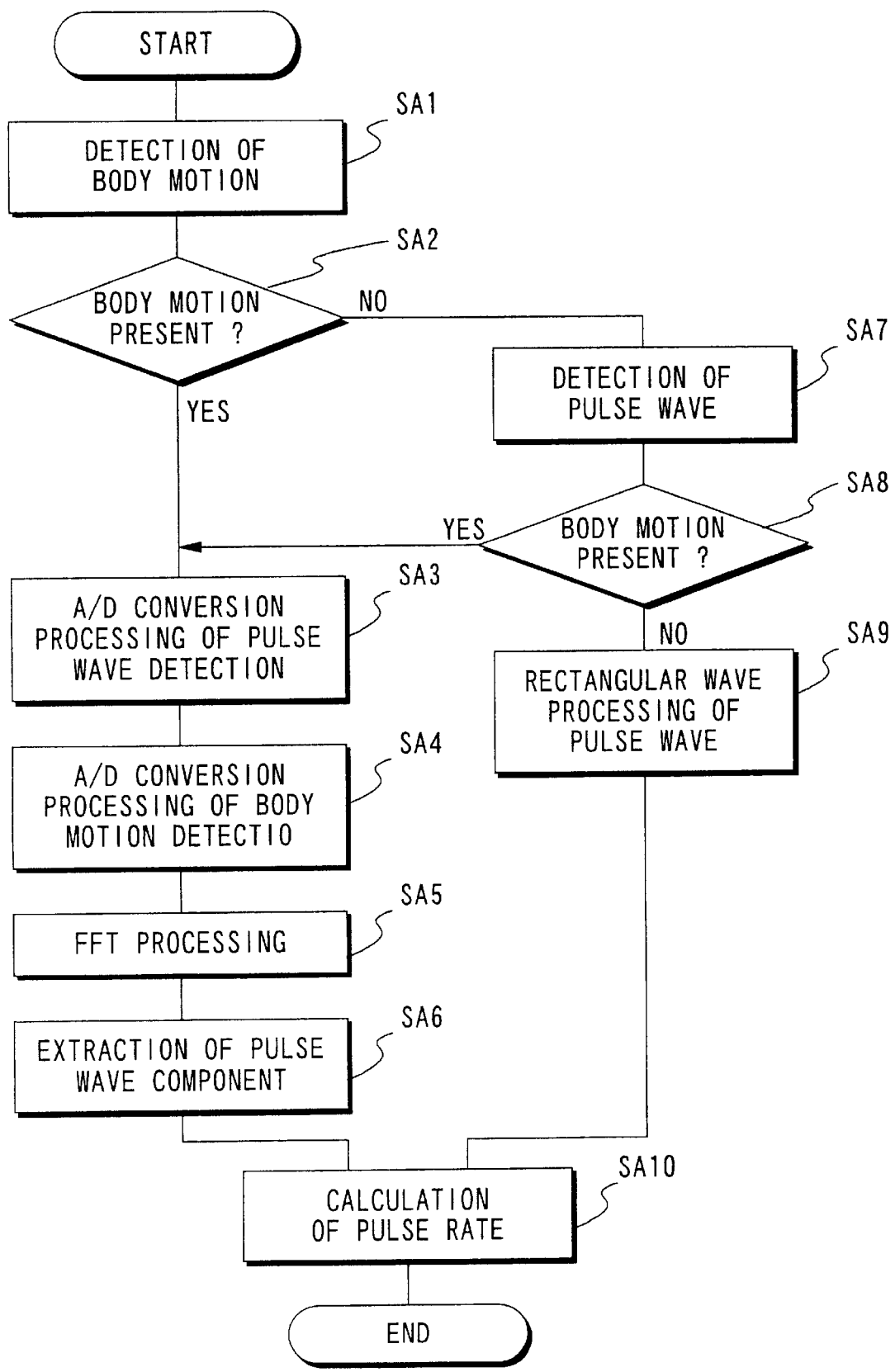
FIG. 8 is a flow chart showing an example of the pulse waveform detection operation according to the first preferred embodiment of the present invention.

FIG. 8 is a flow chart showing an example of the operation for detecting the pulse waveform in the apparatus of the present invention. In the example shown in this figure, in step SA1, CPU 308 detects the body motion waveform from the signal (body motion signal) output from body motion waveform shaping circuit 307. In the following step SA2, CPU 308 decides whether or not body motion is present based on the body motion waveform. When the result of this decision is "YES", then CPU 308 proceeds to step SA3, while when the result of this decision is "NO", CPU 308 proceeds to step SA7.

In step SA3, pulse wave sensor 301 detects the pulse, and outputs the pulse wave signal. The pulse wave signal is amplified by pulse wave signal amplifying circuit 303, and the amplified pulse wave signal is converted from an analog to a digital signal by A/D converting circuit 305. In step SA4, body motion sensor 302 detects body motion, and outputs a body motion signal. This body motion signal is amplified by body motion signal amplifying circuit 304, and the amplified body motion signal is converted from an analog to a digital signal by A/D converting circuit 305. Note that steps SA3 and SA4 are actually carried out in parallel. CPU 308 then performs FFT (step SA5) to the A/D converted pulse wave signal (pulse waveform) and the body motion signal (body motion waveform), respectively. Then, based on the FFT results (spectrum), the frequency components of the pulse wave (pulse wave components) are extracted using a method which will be described below (step SA6).

In step SA7, CPU 308 detects the pulse waveform from the signal (pulse wave signal) output from pulse waveform shaping circuit 306, and, in step SA8, again decides whether or not body motion is present. When the result of this determination is "YES", CPU 308 proceeds to step SA3, while when the result is "NO", CPU 308 proceeds to step SA9. In step SA9, CPU 308 converts the pulse waveform to a rectangular wave.

In step SA10, CPU 308 calculates the pulse rate from the pulse wave component extracted in step SA6 or from the rectangular wave converted in step SA9.

Next, the basic strategy of processing to obtain the pulse wave component (pure pulse waveform) from the pulse wave signal output from pulse waveform shaping circuit 306 will be explained.

FIG. 9A shows the change over time in the amplitude of the signal obtained when the signal of frequency $f_A$ and the signal of frequency $f_B$ are added (where, however, the amplitude of the signal of frequency $f_B$ is ½ that of the signal of frequency $f_A$). FIG. 9B is a graph showing the results after performing FFT on the signal shown in FIG. 9A. The lowest frequency obtained as a result of FFT processing is determined by taking the reciprocal of the analysis duration. For example, if the duration of analysis is 16 s, then the line spectral line can be obtained with a resolution of ¹⁄₁₆ s, i.e. 62.5 ms. Accordingly, the signal to be processed can be resolved into a higher harmonic wave component which is an integer multiple of 16 Hz, in the frequency domain, to obtain a spectrum such as shown in FIG. 9B, in which the power of the each higher harmonic wave component is shown along the vertical axis. For example, in FIG. 9B, the spectral line power for frequency $f_A$ is twice that of the spectral line power of frequency $f_B$.

Figure 10A:
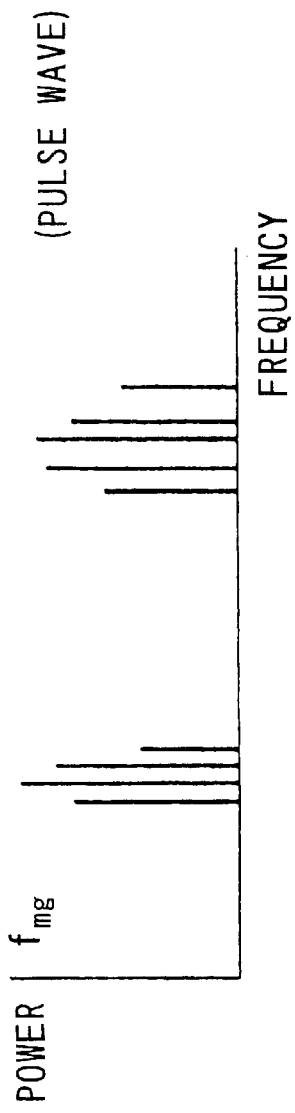
FIGS. 10A, 10B and 10C are graphs showing an example of the result obtained after performing FFT on the signals output from the pulse wave sensor and the body motion sensor when the subject is exercising.
Figure 10B:
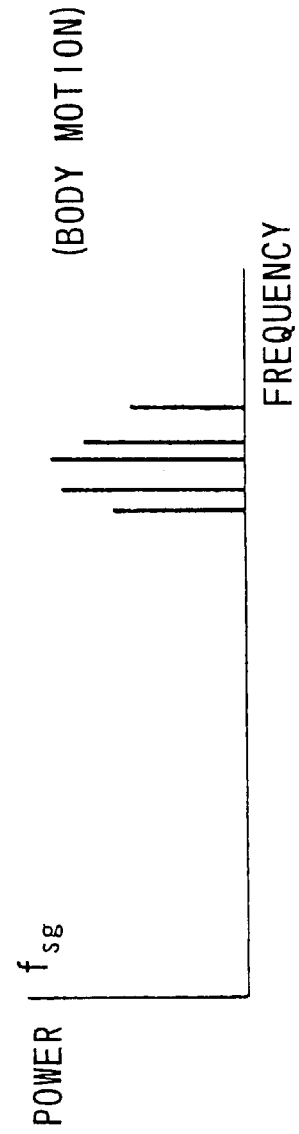
Figure 10C:
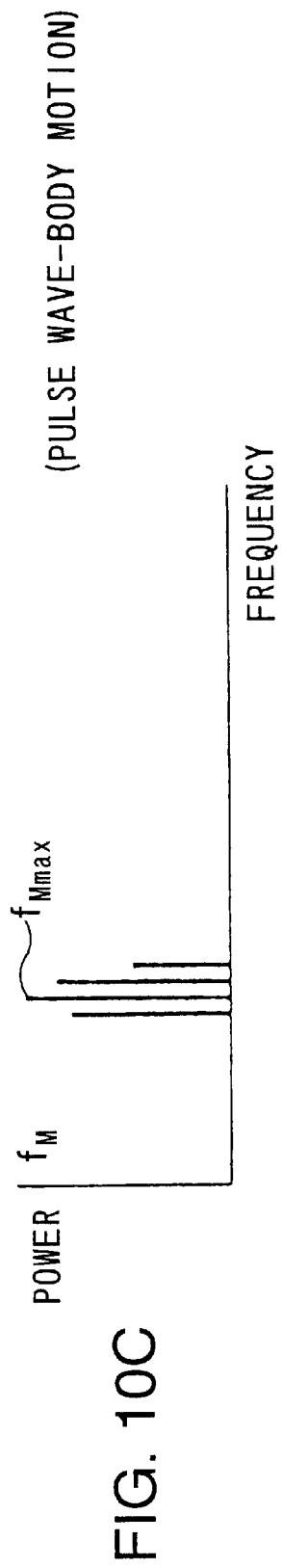

FIG. 10 is a graph showing an example of the results obtained when FFT is performed on the signal output from pulse wave sensor 301 and the signal output from body motion sensor 302 in the case where the subject is exercising. FIG. 10A shows the result (pulse wave spectrum $f_{mg}$) obtained when FFT is performed to the signal (pulse wave signal) output from pulse wave sensor 301; FIG. 10B shows the result (body motion spectrum $f_{sg}$) obtained when FFT is performed to the signal (body motion signal) output from pulse wave sensor 302; and FIG. 10C shows spectrum $f_M$ which is obtained when body motion spectrum $f_{sg}$ is subtracted from pulse wave spectrum $f_{mg}$.

As shown in FIG. 10A, both a pulse wave component and a frequency component generated by body motion are present in pulse wave spectrum $f_{mg}$. On the other hand, body motion sensor 302 responds to body motion only, so that only the frequency component generated by body motion is present in body motion spectrum $f_{sg}$ shown in FIG. 11B. Accordingly, by subtracting body motion spectrum $f_{sg}$ from pulse wave spectrum $f_{mg}$, it is possible to specify the obtained spectrum $f_M$ as the spectrum of the pulse wave component. The pulse wave component is extracted by means of this type of method in step SA6 in FIG. 8.

Next, an explanation will be made of the method for obtaining the frequency of the fundamental wave of the pulse wave which is needed in order to calculate pulse rate.

Figure 11:
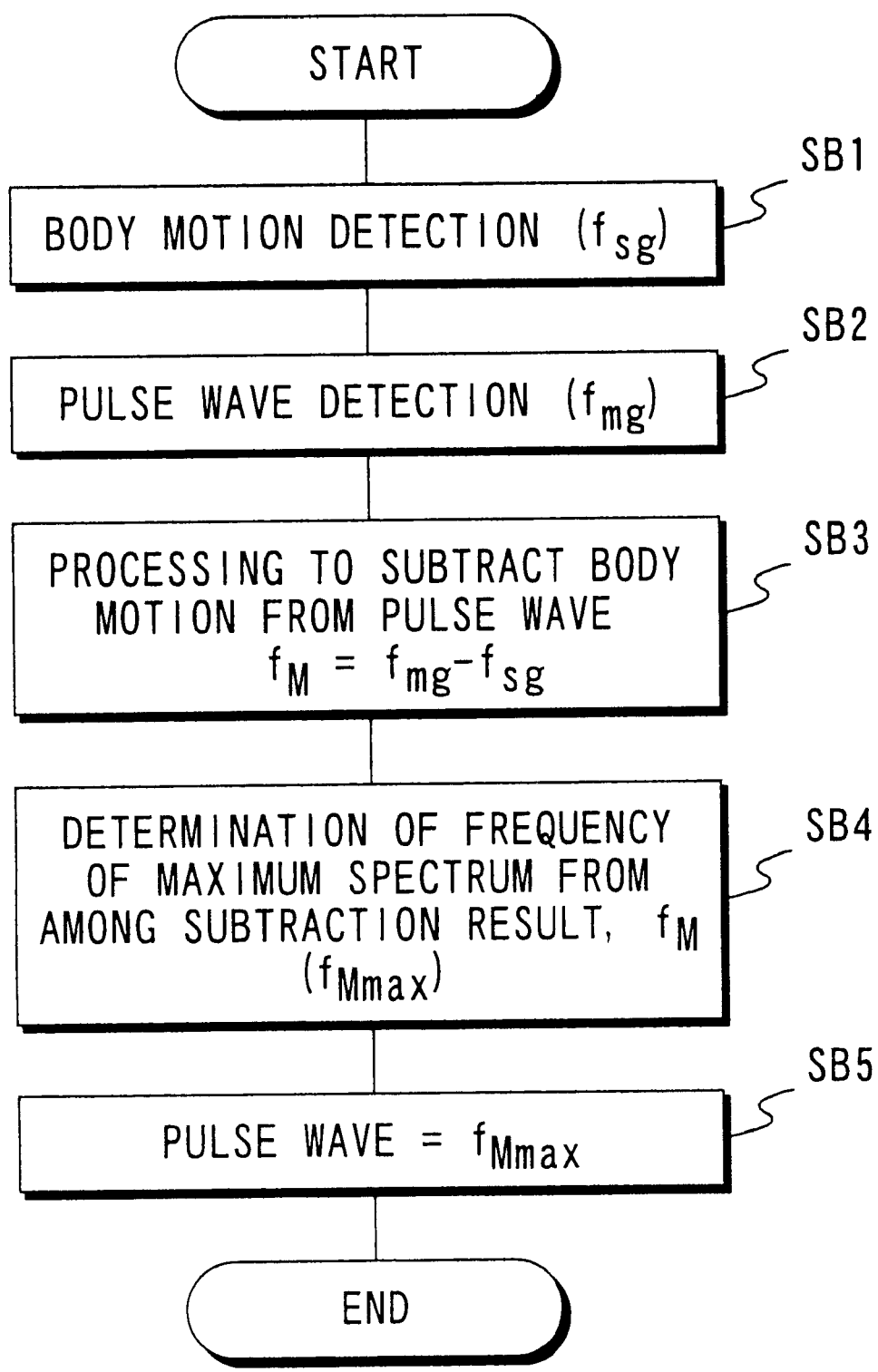
FIG. 11 is a flow chart showing an example of the method for specifying the pulse wave component in the arrhythmia detecting apparatus according to a first preferred embodiment of the present invention.

FIG. 11 is a flow chart showing an example of the method for specifying the frequency of the fundamental wave of the pulse wave. In this figure, CPU 308 first obtains the pulse wave spectrum $f_{mg}$ and the body motion spectrum $f_{sg}$ using FFT (steps SB1, SB2). In the following step SB3, CPU 308 carries out the subtraction operation described above (i.e., $f_M = f_{mg} - f_{sg}$), to extract spectrum $f_M$ of the pulse wave component. In steps SB4 and SB5, CPU 308 extracts the maximum power spectrum from the extracted spectrum $f_M$, and specifies this spectral line frequency $f_{Mmax}$ as the frequency of the fundamental wave of the pulse wave.

In reality, the higher harmonic wave signal exerts an influence, even when simply obtaining the difference between the signals output from the respective sensors using FFT. Accordingly, it can be difficult to obtain a spectrum which corresponds to the pulse wave component only. Therefore, in this embodiment, a spectrum subtraction operation is not carried out. Rather, the body motion component is specified, and the frequency of the fundamental wave of the pulse wave is specified from the frequency component which excludes the specified body motion component.

Figure 12:
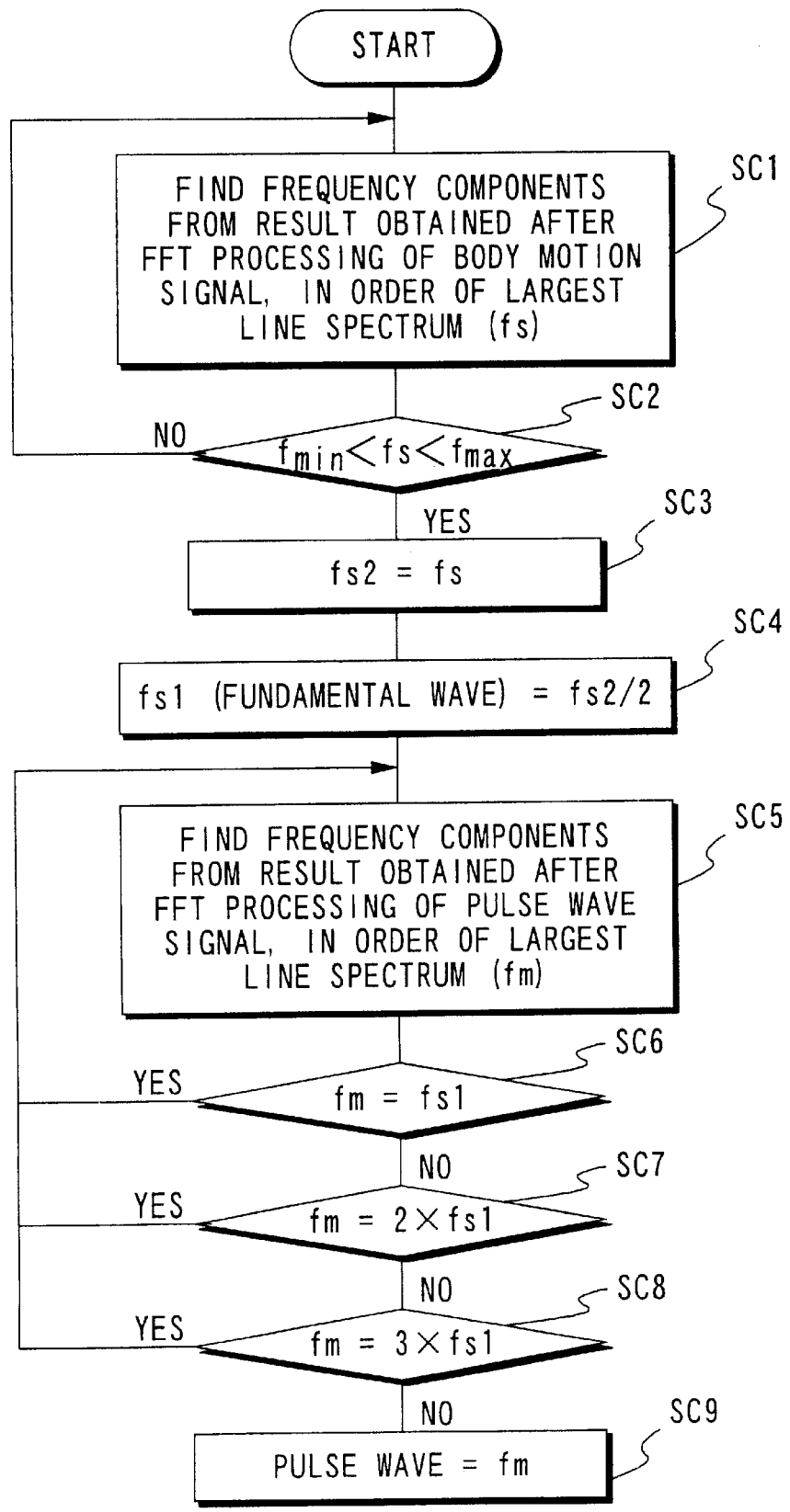
FIG. 12 is a flow chart showing an example of the method for specifying the pulse wave component in this same apparatus.

FIG. 12 is a flow chart showing another example of the method for specifying the frequency of the fundamental wave of the pulse wave. In steps SC1~SC3 in the example shown in this figure, CPU 308 specifies the frequency fs2 of the second higher harmonic wave of body motion, which is relatively easily detected as a body motion component. In reality, this processing is realized by extracting the spectral line having maximum power in the range $f_{max}$~$f_{min}$ (where $f_{max} > f_{min}$), and defining frequency $f_s$ as the frequency $f_{s2}$ of the second higher harmonic wave of body motion.

In the case where the user is performing an exercise, such as running, for example, then the fundamental wave of the body motion in this case typically may appear within a frequency range of 1~2 Hz, while the second higher harmonic wave of body motion typically may appear within a frequency range of 2~4 Hz. Accordingly, in this embodiment, $f_{min}$ is defined to be 2 Hz, i.e., the frequency which is the lower limit for the second higher harmonic wave of body motion. Thus, frequency components below this limit are excluded. On the other hand, when the sampling frequency for the A/D conversion of the body motion signal is set to 8 Hz, then, according to the sampling theorem, the maximum frequency at which the original waveform reappears is automatically determined to be 4 Hz. Therefore, in this embodiment, $f_{max}$ is defined to be 4 Hz, i.e., the maximum frequency as described above. Thus, frequency components above the aforementioned frequency are excluded. Note that it is also acceptable to determine $f_{max}$ by comparing the maximum frequency and the frequency which is the upper limit at which the second higher harmonic wave may appear, and then employing the lower of the two frequencies.

Next, in step SC4, CPU 308 obtains frequency fs1 of the fundamental wave of body motion by dividing frequency fs2 of the second higher harmonic wave of body motion by 2. Then, in steps SC5~SC8, CPU 308 extracts the maximum power spectral line from the pulse wave signal spectrum, within the frequency band from which the frequency components corresponding to the fundamental wave (frequency: fs1), the second higher harmonic wave (frequency: 2×fs1), and the third higher harmonic wave (frequency: 3×fs1) of body motion have been excluded. In step SC9, the frequency of the maximum power spectral line is specified as the frequency fm of the fundamental wave of the pulse wave.

The reason for extracting the maximum power spectral line in the frequency band from $f_{min\sim fmax}$, and treating this frequency as the second higher harmonic wave of the body motion component in the example shown in FIG. 12 will now be explained.

Figure 13:
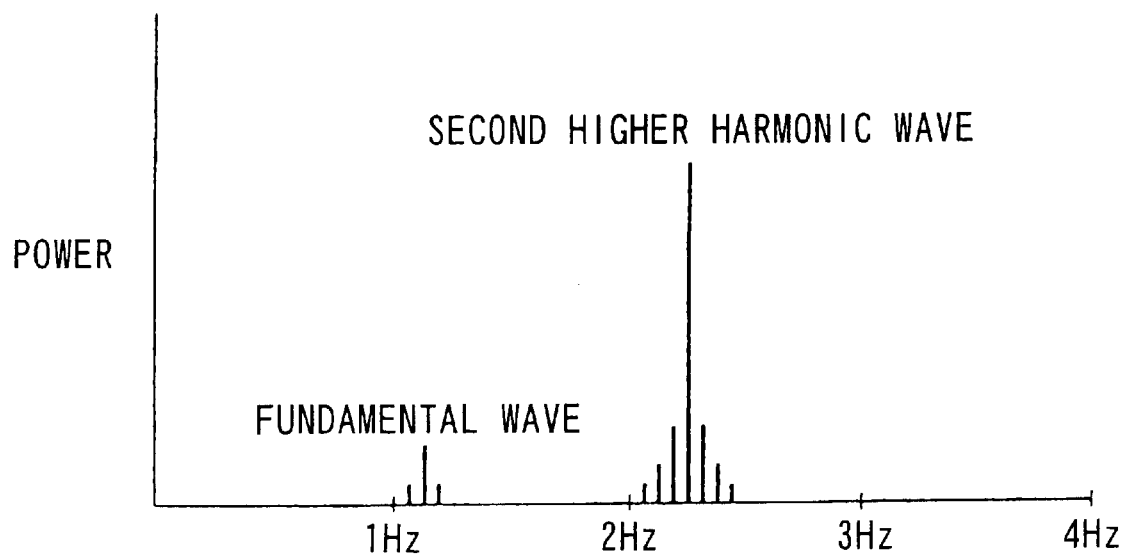
FIG. 13 is a graph showing an example of the result obtained when FFT is performed on the signal output from the body motion sensor.

FIG. 13 shows an example of the result obtained when FFT is performed to the output of body motion sensor 302. In general, when the user is exercising, and particularly when the user is running, then the power of the second higher harmonic wave of body motion becomes even larger as compared to the fundamental wave of body motion, such as shown in FIG. 13 (i.e., a 3- to 10-fold increase when carrying out running of an average intensity). The following two factors may be considered when analyzing the factors for detecting acceleration of body motion sensor 302.

1. upward and downward motion during running
2. swinging forward and drawing back motion of the arms With respect to (1), the upward and downward motion appears uniformly when taking a step with the right foot and when taking a step with the left foot, so that this motion becomes the second higher harmonic wave component of body motion. With respect to (2), a component appropriate to pendulum motion, in which the swinging forward and drawing back motion of the arms constitutes one period, becomes the fundamental wave component of body motion. Typically, however, it is difficult to render the swinging of the arms during running into a smooth pendulum motion, while the power of this component is weak. Conversely, the power of the second higher harmonic wave component of body motion, which is generated because acceleration is applied at the instant the arms swing forward and the instant they are drawn back, is strong. Accordingly, the second higher harmonic wave component of body motion is characteristically obtained in the spectrum of the body motion signal. Thus, the frequency of the maximum power spectral line may be treated as the frequency of the second higher harmonic wave of the body motion component.

Further, as explained above, in the case of ordinary running, given a range of 2 to 4 Hz, it is possible to cover the region in which the second higher harmonic wave appears, regardless of whether the pace of running is slow or fast. Accordingly, by extracting the frequency component of the maximum power after limiting the region in this way, it is possible to extract the frequency component corresponding to the second higher harmonic wave of body motion with certainty. Thus, it is possible to increase the accuracy of detection of the frequency of the fundamental wave of body motion.

Next, the method for specifying the frequency of the fundamental wave of the pulse wave will be explained with reference to FIG. 14, under the condition that the power of the frequency component of the second higher harmonic wave of body motion in the spectrum for the body motion signal is not limited to being a maximum.

When the frequency of the fundamental wave of body motion is set to 1~2 Hz, and $f_{min}$=2 Hz and $f_{max}$=4 Hz, then the frequency components of the fundamental wave, second higher harmonic wave and third higher harmonic wave are the frequency components at which maximum power may be obtained within the range $f_{min}$~$f_{max}$. Since the fourth and higher harmonic waves do not give rise to the primary factors for (1) and (2) above, the power of the frequency components of these harmonic waves, even if present, does not take on a maximum value in the range $f_{min}$~$f_{max}$.

Figure 14:
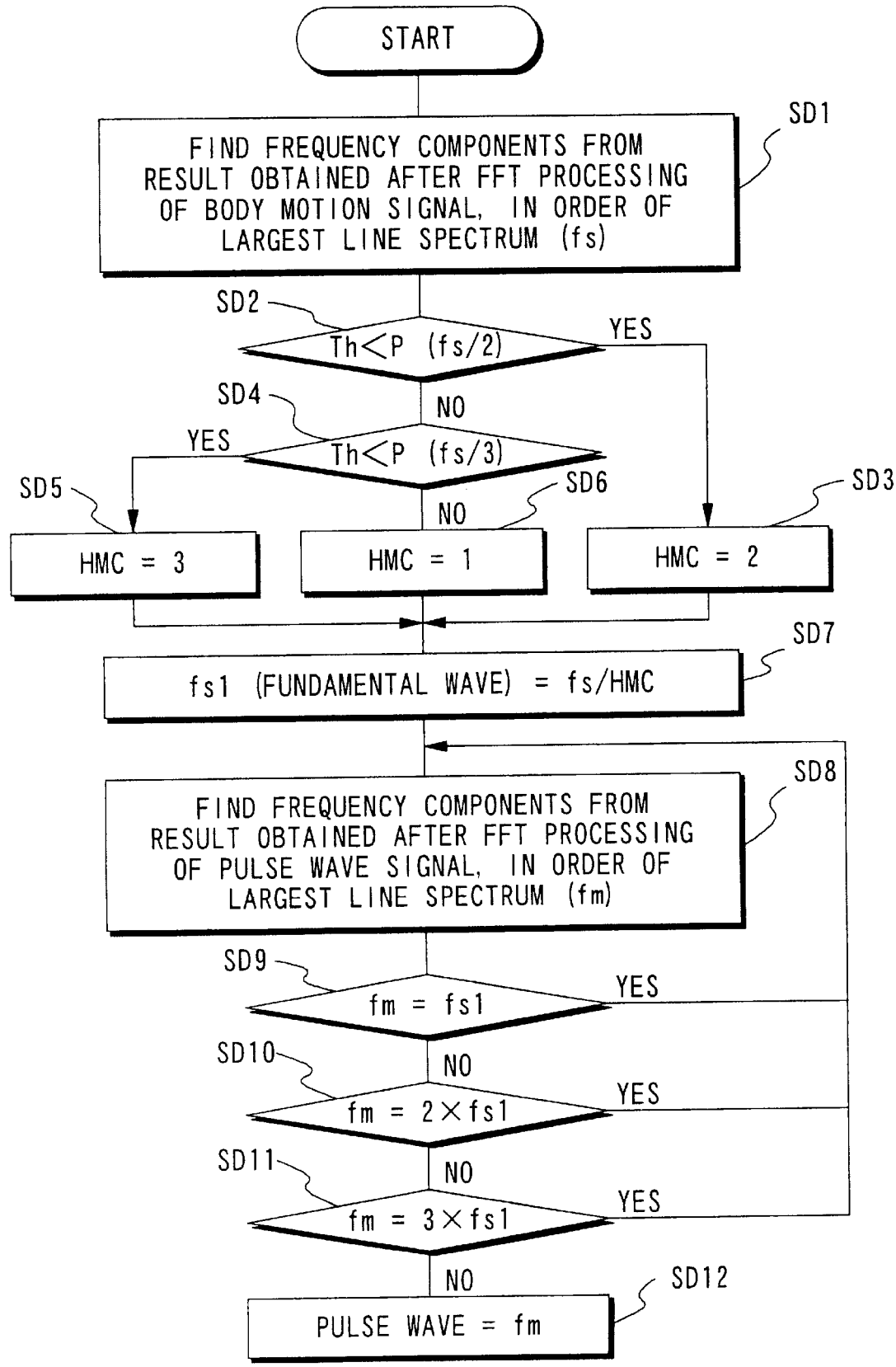
FIG. 14 is a flow chart showing an example of the method for specifying the pulse wave component in the arrhythmia detecting apparatus according to a first preferred embodiment of the present invention.

In view of this, in step SD1 in the method shown in FIG. 14, CPU 308 determines the frequency fs of the line spectral line at which power P is maximal, based on the results of frequency analysis of the body motion signal. Thereafter, in steps SD2 and SD4, CPU 308 specifies whether frequency fs is the frequency component of the fundamental wave, second higher harmonic wave, or third higher harmonic wave of body motion. Specifically, CPU 308 decides whether or not a frequency component above a given fixed value Th is present at a frequency position which is one-half that of frequency fs (step SD2) When the result of this determination is "YES", then, in step SD3, frequency fs is specified as frequency fs2 of the second higher harmonic wave (HMC=2) of body motion. When the result of this determination in step SD2 is "NO", i.e., when a frequency component above a given fixed value Th is not present, then CPU 308 decides whether or not a frequency component above a given fixed value Th is present at a frequency position which is ⅓ that of frequency fs (step SD4). When the result of this determination is "YES", then, in step SD5, CPU 308 specifies frequency fs as frequency fs3 of the third higher harmonic wave (HMC=3) of body motion. When the result of the determination in step SD4 is "NO", i.e., when a frequency component above a given fixed value Th is not present at a frequency position which is ⅔ or ⅓ of frequency fs, then, in step SD6, CPU 308 specifies frequency fs as frequency fs1 of the fundamental wave of body motion.

As a result of the preceding processing, the frequency fs obtained in step SD1 is specified as the frequency of either the fundamental wave (HMC=1), second higher harmonic wave (HMC=2), or third higher harmonic wave (HMC=3) of body motion. Then, in step SD7, CPU 308 divides the frequency fs by HMC, to obtain the frequency fs1 of the fundamental wave of body motion. Subsequently, as a result of processing equivalent to that shown in steps SC5 through SC9 in FIG. 12, CPU 308 extracts the maximum frequency component from which the frequency components coinciding with the fundamental wave, second higher harmonic wave, and third higher harmonic wave of the body motion component have been excluded, and specifies this as frequency fm of the fundamental wave of the pulse wave (steps SD8 through SD12).

Figure 15:
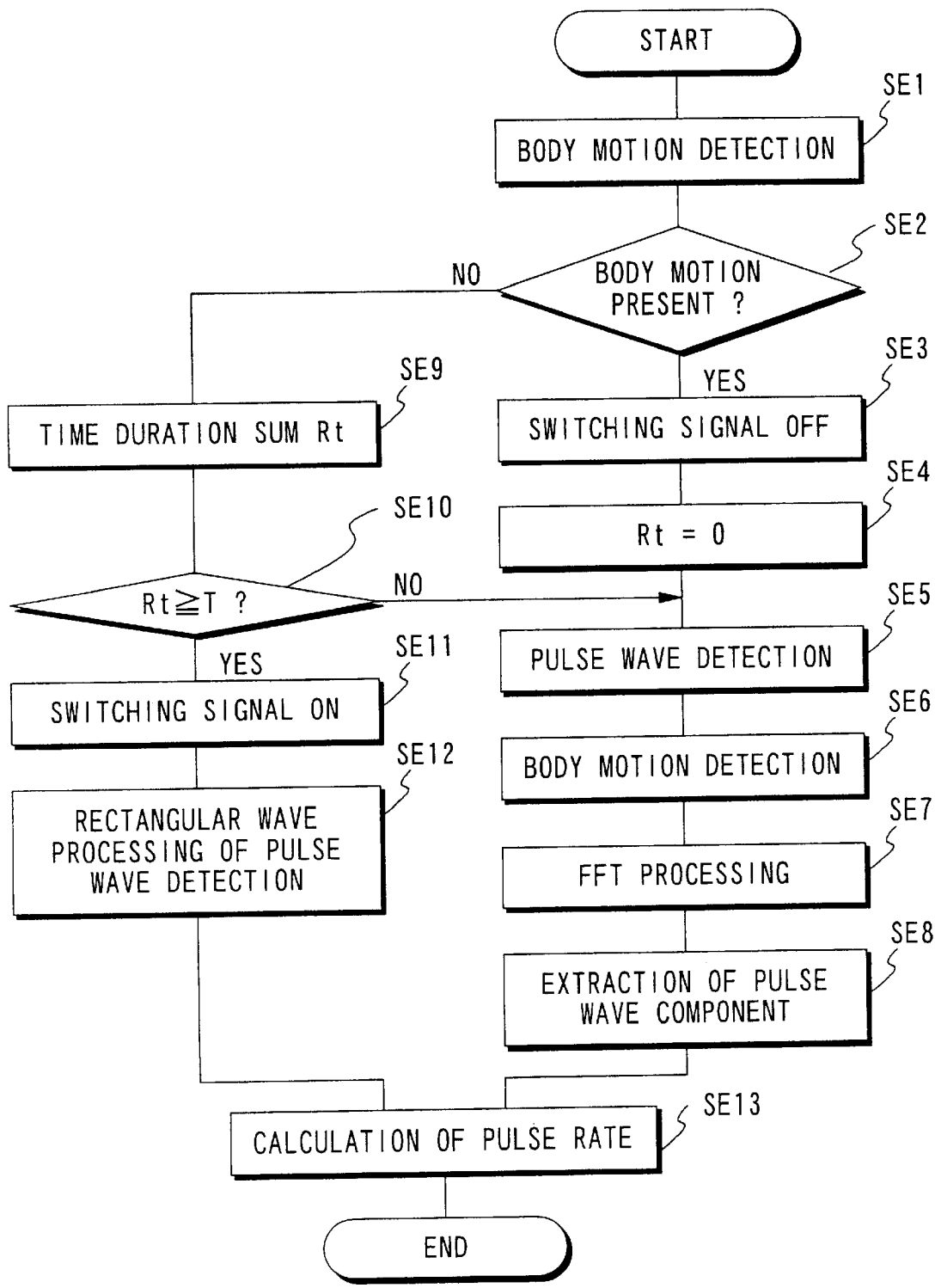
FIG. 15 is a flow chart showing an example of the method for specifying a pulse wave component in this same apparatus.

FIG. 8 shows an example wherein the processing immediately shifts to rectangular wave processing once the body motion signal ceases to be detected. In reality, however, it is possible that when the user is exercising a "body motion not detected" result could occur according to the instantaneous value of the body motion signal. Accordingly, the apparatus is design to switch from a calculation method to a rectangular wave processing method once the time period during which the body motion signal is not detected exceeds a given fixed time period T. The procedure for this switching will now be explained with reference given to FIG. 15.

In steps SE1 and SE2, CPU 308 decides whether or not body motion is present according to the signal (body motion signal) output from body motion waveform shaping circuit 307. When the result of this determination is "YES", processing proceeds to step SE3. In step SE3, CPU 308 sets the switching signal for switching the pulse rate calculating method to "OFF". In step SE4, the cumulative time Rt during which there is no body motion is set to zero.

In steps SE5 and SE6, pulse wave sensor 301 detects the pulse and outputs a pulse wave signal. This pulse wave signal is amplified by pulse wave signal amplifying circuit 303. The amplified pulse wave signal is converted from an analog to a digital signal at A/D converting circuit 305. At the same time, body motion sensor 302 detects body motion and outputs a body motion signal. This body motion signal is amplified by body motion signal amplifying circuit 304, and the amplified signal is then converted from an analog to a digital signal by A/D converting circuit 305.

In step SE7, CPU 308 carries out FFT to the A/D converted body motion signal and the pulse wave signal, respectively. In step SE8, the pulse wave components (pure pulse waveform) is extracted from the FFT processed results (spectrum), and the frequency of the fundamental wave of the pulse wave is specified.

On the other hand, if the result of the determination in step SE2 is "NO", then, in steps SE9 and SE10, CPU 308 starts calculating time based on the output signals from oscillation circuit 311 and frequency dividing circuit 312. Time period Rt is cumulatively summed, and CPU 308 decides whether or not cumulative time Rt exceeds a fixed time period T which is determined according to the sampling period or the sampling number of the signal which is used in FFT processing. When the result of the determination is "YES", then processing proceeds to step SE11, while when the result of the determination is "NO", processing proceeds to step SE5.

In step SE11, CPU 308 sets the switching signal for switching the pulse rate calculating method to "ON", and halts A/D conversion processing and FFT processing. Note that when carrying out rectangular waveform processing, A/D conversion processing and FTT processing may be carried out in parallel, however, from the perspective of energy consumption, it is preferable to suspend A/D conversion processing and FFT processing when carrying out processing for the rectangular wave, as these are only necessary in the processing for frequency analysis.

In step SE12, pulse waveform shaping circuit 306 converts the pulse wave signal to a rectangular wave. In step SE13, the pulse rate is calculated from the frequency specified by CPU 308 in step SE7 or from the rectangular wave converted in step SE12.

2. Modifications of the First Embodiment

Arrhythmia may be caused by factors which are quite dangerous, as well as by factors for which there is little cause for concern. However, given that the pulse is an indicator of the body's state of health, a disturbance therein, such as arrhythmia, is hardly desirable. Namely, such a disturbance indicates an anomaly in physical state. Hypothetically, arrhythmia may result even in a healthy person having no illness, due to lack of sleep, for example. Similarly, arrhythmia may also occur as a result of the intake of too much coffee or excessive psychological stress. Therefore, it is possible to know the extent of an individual's state of health by referring to the number of times arrhythmia is detected.

Further, unlike arrhythmia which occurs in a healthy person, it is known that arrhythmia which is caused by a serious cardiac or vascular disease may show up 200 times or more per day in an electrocardiogram in the case where there is just a single cause, or may take on a variety of forms in the electrocardiogram when there are multiple causes present. Accordingly, a threshold value may be set to 200, for example, with the user notified when the number of times arrhythmia is detected exceeds this value.

In the case of an individual with a cardiac or vascular disease, arrhythmia occurring frequently within a short period of time may be considerably dangerous, and may even result in sudden death in the most extreme cases. Thus, if the notice is provided of how frequently arrhythmia occurs, then the user is able to monitor his own state of health. For example, in the case where the user feared being late to a meeting and was about to rush, if the aforementioned arrhythmia frequency is displayed at this time and the value thereof is large, the user can restrain himself from running.

When arrhythmia occurs frequently during sleep, such that a dangerous physical condition results, then a buzzer 17 sounds when arrhythmia frequency information FHD exceeds a threshold value. Thus, the user is made aware he is in a dangerous physical state, allowing him to take appropriate countermeasures such as taking medicine. Thus, the most extreme circumstance of sudden death may be avoided.

In other words, in the first embodiment described above, the time elapsed since the start of measurement is measured. When the detected frequency or number of arrhythmia events exceeds a specified frequency (such as 200 times/day) or number (such as 200 times), then the user may be cautioned by notice to this effect. In this case, notice may be provided at the point in time when the detected frequency or number exceeds the specified frequency or number, at the conclusion of measurement, or at a point in time after the conclusion of measurement. However, with the perspective of providing the user with information which he can use to determine exercise intensity, it is preferable to provide notice at the point in time when the detected frequency or number of arrhythmia events exceeded the specified values. An explanation of the notifying means will be provided under section 4, "Modifications of the Embodiments".

When renewing the reference value for the pulse wave interval, it is acceptable to employ the average value of a specific number of the most recent pulse wave intervals as the new reference value, rather then simply defining the most recent pulse wave interval as the reference value. In this case, it is acceptable to obtain the average value after weighting, so that the more recent intervals are weighted more heavily. This approach may also be applied in the case where the pulse rate is calculated based on a specific number of the most recent pulse wave intervals.

Further, all the pulse wave intervals may be sequentially stored in RAM 309, rather than storing the pulse wave interval in RAM 309 only when arrhythmia has not been detected. In this case, then, the pulse wave interval reference value and the pulse rate may be calculated based on pulse wave intervals which do not include pulse wave intervals obtained at the time of detection of an arrhythmia. In this case, it is necessary to decide whether or not a pulse wave interval corresponds to the time of an arrhythmia detection. This can be done by assigning specific information only to those pulse wave intervals corresponding to the time of an arrhythmia detection, and then storing these in RAM 309. The specific information which is assigned to pulse wave intervals corresponding to the time of detection of an arrhythmia may be fixed information indicating only that the pulse wave interval corresponds to the time of detection of an arrhythmia, or may be variable information indicating the clock time at which the arrhythmia was detected. Naturally, it is also acceptable to directly assign the aforementioned specific information to the pulse wave interval, or to indirectly assign the specific information using the address and so on in which the pulse wave interval is stored.

Further, when carrying out rectangular wave processing (when not exercising), it is acceptable to use a method other than division to determine whether or not the difference (deviation) in the most recent pulse wave interval with respect to the reference value of the pulse wave interval is within the allowed range. For example, a range of within ±5% of the pulse wave interval reference value may be obtained, and a decision may be made as to whether or not the most recent pulse wave interval is within this allowed range. Moreover, it is also acceptable to obtain a reference value based on pulse wave intervals detected after the elapse of a specific amount of time since the start of the arrhythmia detection operation, rather than obtaining the reference value based on the pulse wave intervals immediately subsequent to the start of the detection operation.

The pulse wave signal includes not only the fundamental wave component of the pulse wave, but also the higher harmonic wave components of the pulse wave. When the power of the higher harmonic wave component is greater than the power of the fundamental wave component, then, in the preceding first embodiment, a determination is made as to whether or not the frequency of the higher harmonic wave component is present within the allowed range for the fundamental wave component, with the result that an arrhythmia is incorrectly determined to have occurred. In order to avoid this type of error, it is acceptable to apparatus to decide that arrhythmia is not present in the case where, during frequency analysis, the frequency of the maximum power spectral line in the pulse wave component is equivalent to an integer multiple (i.e., frequency of each higher harmonic wave) of the value (pulse frequency) obtained by dividing the previous pulse rate by 60.

The first embodiment provided that rectangular wave processing was carried out when there was no body motion, while frequency analysis processing was carried out when body motion was present. However, it is acceptable to carry out frequency analysis processing in either of these cases. Moreover, rectangular wave processing may also be applied in either case, so long as it is possible to provide a means for removing components other than the pulse wave from the pulse wave signal at the pulse wave signal input stage. Additionally, it is also possible in these embodiments to constantly carry out processing to remove a body motion component from the pulse wave signal, irrespective of whether body motion is present or not. In this case, even if processing is carried out, there is no component to be removed from the pulse wave component when there is no body motion present. Accordingly, the result obtained is equivalent to that in the first embodiment, in which the details of processing change in response to the presence or absence of body motion.

When carrying out rectangular wave processing, it is acceptable to provide notice of the difference between the actual pulse wave interval and the reference pulse wave interval. As a result, the degree of deviation in the pulse wave can be quantified.

3. Second Embodiment

Arrhythmia may occur in even a healthy person, as a result of intense exercise such as running, for example. Ascertaining the conditions under which this type of arrhythmia is generated may be deemed useful to controlling physical condition during exercise. However, in the first embodiment, detection of arrhythmia was carried out regardless of whether or not the user was carrying out intense exercise. In other words, the first embodiment did not discriminate between an arrhythmia generated during intense exercise and an arrhythmia generated when the user is engaging in more moderate activity. Accordingly, the second embodiment takes advantage of the fact that there is a constancy in body motion during such intense exercise as running, and is designed to detect only arrhythmia which occurs during exercise having a constancy in the pitch of the body motion, such as intense exercise.

The second embodiment of the present invention will now be explained with reference to the figures. As in the case of the first embodiment, the apparatus for detecting arrhythmia according to this second embodiment is realized in the form of a wristwatch such as shown in FIG. 3. The arrhythmia detecting apparatus according to the second embodiment has a time measuring mode and an arrhythmia detection mode. Arrhythmia detection, counting of the number of arrhythmia events, and calculation of the pulse rate are carried out in the arrhythmia detection mode. An explanation of those aspects of the second embodiment which are common to those of the first embodiment will be omitted here.

3-1. Structure of the Second Embodiment

The structure of the arrhythmia detecting apparatus according to the second embodiment is approximately the same as that shown in FIG. 2, with only the functioning of CPU 308 differing from that in the first embodiment.

Namely, CPU 308 in the arrhythmia detecting apparatus according to the second embodiment differs from that of the first embodiment in that, arrhythmia detection in the arrhythmia detection mode is carried out only when constancy is present in body motion. The determination of whether or not constancy is present may be made by carrying out processing on the body motion signal which is equivalent to the processing executed on the pulse wave signal when determining the presence or absence of arrhythmia using frequency analysis in the first embodiment. The details of this decision will be discussed in the explanation of the operation of the second embodiment. Additionally, note that in the arrhythmia detection processing in the first embodiment, a determination is made as to the presence or absence of arrhythmia by specifying the fundamental wave of the pulse wave. The second embodiment, however, decides the constancy of body motion by specifying the second higher harmonic wave of body motion.

3-2. Operation of the Second Embodiment

The operation of the arrhythmia detecting apparatus (i.e., operation of arrhythmia detecting mode) according to the second embodiment will now be explained. The operation of the arrhythmia detection mode in this second embodiment can be broadly divided into a "First Arrhythmia Detecting Operation" and a "Second Arrhythmia Detecting Operation". However, as the former is equivalent to the "First Arrhythmia Detecting Operation" of the first embodiment, an explanation thereof will be omitted here.

3-2-1. Second Arrhythmia Detecting Operation According to the Second Embodiment

The operation of the second arrhythmia detecting operation according to this embodiment differs from that of the first embodiment in that processing is carried out to decide the presence or absence of arrhythmia based on the results of frequency analysis of the pulse wave signal in the case where there is constancy in body motion. However, when body motion is lacking constancy, then the processing is not carried out in this embodiment.

3-2-2. Method for Deciding Body Motion Constancy

Examples of methods for deciding whether or not constancy is present in body motion include a "time domain decision method" and a "frequency domain decision method".

3-2-2-1. Time Domain Decision Method

As a time domain decision method, a method may be cited in which the range of the wave intervals of the second higher harmonic wave of body motion complying with a specific range (for example, ±5%) in the pulse rate domain is defined as the allowed range. When the wave interval of the second higher harmonic wave of body motion is within this allowed range, then a determination is made that constancy is present in body motion. If, however, the value is not in this range, then a determination is made that constancy is not present in body motion.

For example, given a pulse rate of 170 beats/min, then: 170×0.05=8.5. Accordingly, the ±5% range in the pulse rate domain is ±8.5 beats/min., while the corresponding range in the frequency domain is ±0.1417 Hz. If we assume that there is a linear correspondence between the frequency range in which the fundamental wave of the pulse wave may be present (generally, 0.6~3.5 Hz) and the time range in which the interval of the second higher harmonic wave of body motion may be obtained (0.5~0.25 s), then the allowed range in the time domain related to the interval of the second higher harmonic wave of body motion corresponding to ±0.1417 Hz becomes: ±0.1417×(0.5−0.25)/(3.5−0.6) ±0.0122. Accordingly, assuming the reference value of the interval of the second higher harmonic wave of body motion is 0.28 s, then a determination is made that "constancy is present" when the interval of the second higher harmonic wave of body motion is within the range of 0.28±0.0122 s, while a determination is made that "constancy is not present" when the value is outside this range.

3-2-2-2. Frequency Domain Decision Method

As a frequency domain decision method, a method may be cited in which the highest power frequency spectral line within the range (2~4 Hz) in which the spectral line of the second higher harmonic wave of body motion may be present is extracted from the results of frequency analysis on the body motion signal. When the scope of the side lobes of this spectral line broaden appropriately, and there is a sufficient power difference between the spectral line and other spectral lines in this range (30% or greater, for example), then a decision is made as to whether or not the spectral line frequency is equal to twice that of the frequency corresponding to the previous pulse rate (i.e., frequency of the fundamental wave of body motion). When these are determined to be equivalent, then a decision is made that "constancy is present". Note that the determination of whether or not the scope of the side lobes broadens appropriately is made according to the same method employed in the first embodiment. Further, as in the case of the first embodiment, it is not necessary that the two frequencies be strictly equal; rather, there is an allowed range as described below.

The allowed range in which the frequencies as described above may be judged "equal" may be optionally set. There is, however, a correlation between the pulse rate and the frequency of the fundamental wave of body motion. In this embodiment, the allowed range for a determination of "equal" with respect to the pulse rate in arrhythmia detection is set in the same way as in the first embodiment. Therefore, the second embodiment defines the limits corresponding to the allowed range for a determination of "equal" with respect to pulse rate to be the allowed range for a determination of "equal" with respect to the second higher harmonic wave of body motion.

For example, assuming a pulse rate of 170/min (frequency of the fundamental wave of the pulse wave of approximately 2.833 Hz), and an allowed range of ±5% for a determination of "equal" in connection to the pulse rate, then the allowed range with respect to the frequency of the fundamental wave of the pulse wave (i.e., the allowed range in the frequency domain) is also ±5%, or ±0.1417 Hz. If we assume a linear correspondence between the frequency range (2~4Hz) in which the second higher harmonic wave of body motion may be present and the frequency range (0.6~3.5 Hz) in which the fundamental wave of the pulse wave may be present, then the allowed range in connection with the second higher harmonic wave of the pulse wave corresponding to the aforementioned allowed range (±0.1417 Hz) is ±0.1417×(4−2)/(3.5−0.6)=±0.0977 Hz. On the other hand, if the duration of frequency analysis is set to 16 s, then spectral lines are obtained at discrete frequencies such as 3.3750, 3.4375, 3.5000, 3.5625, 3.6250, and 3.7667 Hz, in the vicinity of a frequency which is twice (3.53 Hz, for example) the frequency corresponding to the previous pulse rate. Accordingly, provided that the spectral line selected as the spectral line of the second higher harmonic wave of body motion is one of these discrete spectral lines, then it will be within the allowed range of 3.53±0.0977 Hz. Accordingly, a decision of "equal" is rendered in this case, while a decision of "not equal" is rendered in all other cases.

The reason for carrying out a determination of equality as described above, is so that the arrhythmia detection operation will not be carried out if body motion is determined to lack constancy, even in the case where body motion changes in a step manner. For example, if the user quickly changes the pitch of exercise which exhibits constancy, and, moreover, that change occurs during the transition from the time period which was the subject of the previous frequency analysis to the time period which is the subject of the current frequency analysis, then the frequency of the second higher harmonic wave of body motion which is specified based on the results of the previous frequency analysis, and the frequency of the second higher harmonic wave of body motion which is specified based on the results of the current frequency analysis, will differ. Accordingly, a determination that body motion exhibits constancy should not be made. Further, when the duration of frequency analysis is sufficiently long, then a problem occurs in which arrhythmia is detected when constancy is not present in body motion, even if the above-described "equal" determination is omitted.

Note that processing equivalent to that shown in FIG. 14 is carried out under the condition that the power of the frequency component of the second higher harmonic wave of body motion is not limited to being stronger than the power of the other frequency spectrum components. Namely, the maximum power frequency component in the preconceived frequency range (2~4 Hz, for example) is assumed to be the frequency component of either the fundamental wave, second higher harmonic wave or third higher harmonic wave of body motion. By investigating the power in frequencies which are ½ or ⅓ that of the aforementioned maximum power frequency component, it is possible to specify whether the aforementioned frequency component is one of either the fundamental wave, second higher harmonic wave or third higher harmonic wave components of body motion or not. In FIG. 14, the frequency of the fundamental wave of body motion is specified based on the specified component, however, in the second embodiment the second higher harmonic wave of body motion is specified.

3-2-2. Overall Operation of Second Embodiment

The overall operation of the second embodiment will now be explained with reference to FIG. 16. Unless specifically stated, operations are carried out by CPU 308.

Figure 16:
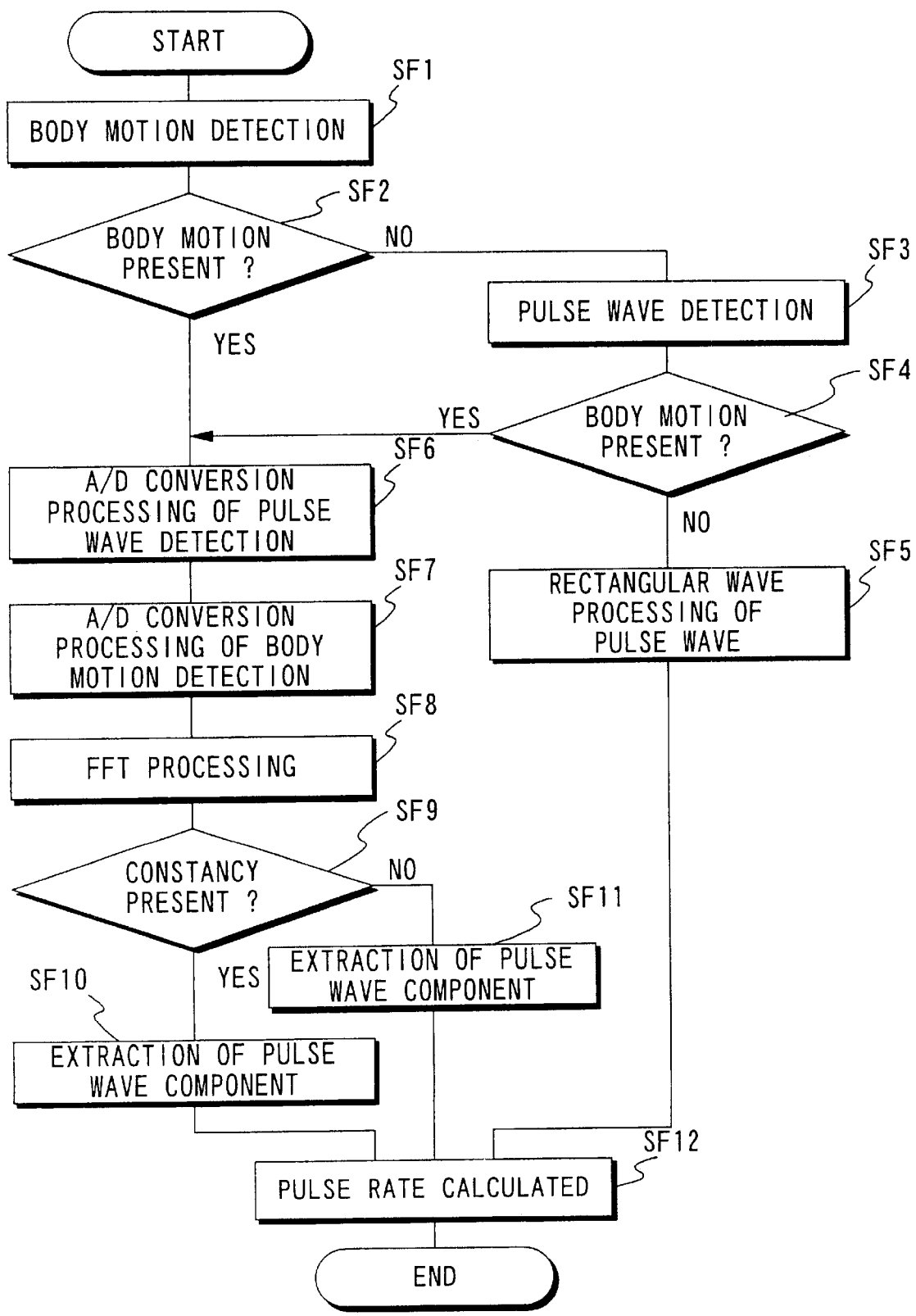
FIG. 16 is a flow chart showing an example of the operation to detect the pulse waveform in the arrhythmia detecting apparatus according to a second preferred embodiment of the present invention.

The processing in steps SF1~SF8 in FIG. 16 are equivalent to the processing performed in steps SA1~SA5, SA7~SA9 of FIG. 8. Namely, when a body motion signal (body motion waveform) is present, then the pulse wave signal (pulse waveform) is detected, and rectangular wave processing is carried out on the pulse wave signal. On the other hand, when a body motion signal is present, then the pulse wave signal and the body motion signal are detected and converted from analog to digital signals, with FFT processing subsequently carried out on each of these respectively. Then, based on the results of FFT processing of the body motion signal, in step SF9, the processing described above is carried out to decide whether or not constancy is present in the body motion. When constancy is present, then processing equivalent to that of step SA6 in FIG. 8 is carried out in step SF10. Accordingly, if arrhythmia has occurred, it is reported at this stage of the processing. On the other hand, when a decision is made that body motion is lacks constancy in step SF9, then processing to determine only the frequency of the fundamental wave of the pulse wave is carried out in step SF11. In other words, arrhythmia detection processing is not performed in step SF11, but rather only the processing for determining the frequency of the fundamental wave of the pulse wave from the results of frequency analysis of the pulse wave signal is performed.

Next, the pulse rate is calculated in step SF12, based on the rectangular waveform signal obtained in step SF5, the information obtained in step SF10 (i.e., the frequency of the fundamental wave of the pulse wave or else the fact that the frequency could not be specified), or the information obtained in step SF11 (the frequency of the fundamental wave of the pulse wave or else the fact that the frequency could not be specified). Note that when the frequency of the fundamental wave of the pulse wave could not be specified in steps SF10 or SF11, then the pulse rate is not calculated in step SF10, but rather the previous pulse rate is employed as the current pulse rate.

In this way, by means of the second embodiment, it is possible to detect arrhythmia during exercise in which there is constancy in the body motion (i.e., during intense exercise such as running, or during running in which the body motion pitch is 80 times per minute).

4. Modifications of the First and Second Embodiments

The first and second embodiments of the present invention were explained in detail above with reference given to the accompanying figures. The specific structures of these embodiments are not limited thereto, however. Rather, provided they remain within the intended scope of the invention, various design modifications are also included within the present invention.

For example, the first and second embodiments may be combined, with a mode for detecting arrhythmia when there is constancy in body motion and a mode for carrying out arrhythmia detection irrespective of constancy in body motion provided to the same arrhythmia detecting apparatus. In this way, the user may select the preferred mode.

Further, each of the preceding embodiments presupposed that the allowed range in which an "equal" determination will be reached was fixed. However, the present invention is not limited thereto. Rather, it is acceptable for the allowed range to be variable. For example, the width of the allowed range may be varied in response to the operation of a specific switch. In this case, it is preferable to provide a design which notifies the individual making the settings of information showing the width of the allowed range (±5%, for example). In addition, it is also acceptable to dynamically change the width of the allowed range in response to the reference value of the pulse wave interval, the previous pulse rate, the frequency of the previous fundamental wave of body motion and so on. Also, in general, the width of appropriate variation in the pulse rate when the user is not exercising is small as compared to that during exercise. Thus, if the allowed range related to the frequency of the fundamental wave of the pulse wave when there is no body motion is set to be narrower than the allowed range when body motion is present, then it is possible to detect arrhythmia with even greater accuracy. Moreover, an arrangement may also be considered in which the widths of the various allowed ranges is defined to be an absolute value which is not dependent on the pulse rate or the frequency of the fundamental wave of body motion.

In each of the preceding embodiments, with respect to the results obtained after performing FFT processing on the pulse wave signal and the body motion signal, a determination was made as to whether or not the scope of the side lobes around the targeted spectral line broadened appropriately. However, it is also acceptable to extend this determination to all spectral lines within a specific range, rather than to just the spectral lines neighboring the targeted spectral line. For example, a design may be provided wherein the scope of the side lobes is determined to broaden appropriately only if the power difference between the targeted spectral line and its neighboring spectral lines is 5% or more, and the power difference between the targeted spectral line and spectral lines which are one interval further away is 10% or greater. Alternatively, it is also acceptable to decide that the scope of the side lobes broadens appropriately only in the case where the aforementioned power difference is 5% or more for all spectral lines within the allowed range in which a determination of "equal" is obtained.

It is also acceptable to provide a design which informs a remote monitor when the duration during which the pulse wave is not detected, which is equivalent to the heart stopping, exceeds a specific time period. As a result, a monitor such as a physician, who is physically removed from the user, who suffers from heart disease for example, to whom the apparatus has been attached, can be notified immediately that the user's heart has stopped. Thus, the appropriate counter measures can be taken immediately. Note that the time duration which is the reference in this case may be a fixed duration common for all users, or may be set separately for each user. The specific system for notifying a remote monitor in the case of an emergency will be discussed in detail below under the section titled "Systemization".

The site of attachment of the pulse sensor is not limited to the finger. Rather, any site (ear, neck, etc.) is acceptable, provided it is possible to obtain a pulse wave measurement there. Also, in addition to an acceleration sensor, an optical sensor may also be employed for the body motion sensor. The site of attachment of the body motion sensor is not limited to the arm, but may be located any where on the body. Further, each of the sensors may be fixed in place using a finger sack or finger belt, for example.

Figure 43A:
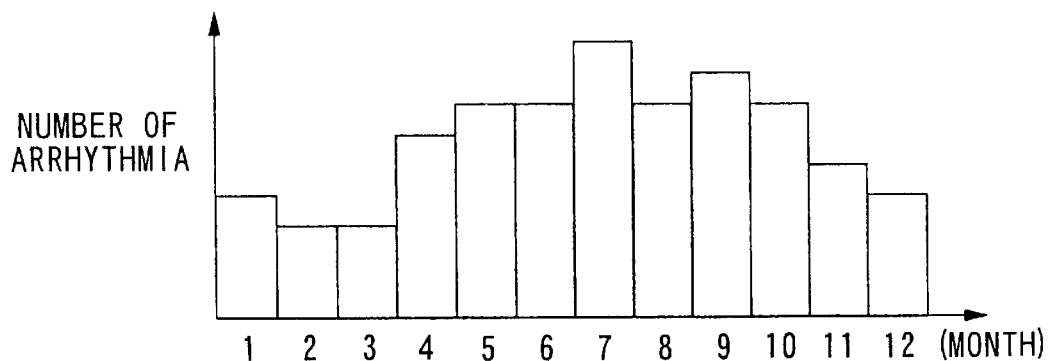
FIGS. 43A, 43B and 43C are figures showing an example of the notifying means according to the present invention, wherein 43A, 43B and 43C show monthly, weekly and hourly histograms, respectively.
Figure 43B:
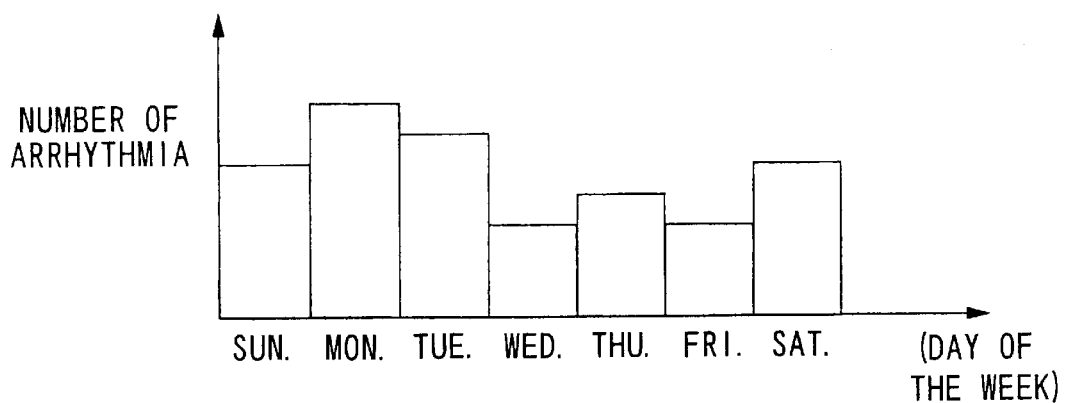
Figure 43C:
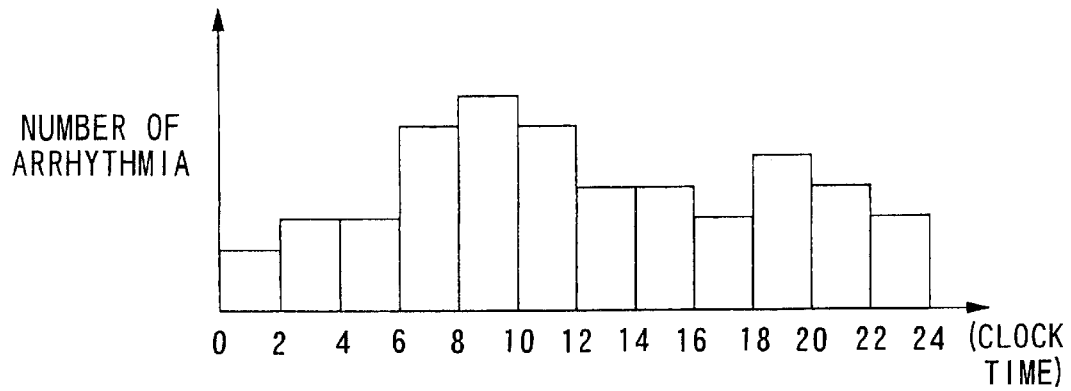

The apparatus may be designed to display the clock time at which arrhythmia was detected upon request by the user. In addition, a histogram may be displayed with the detection time along the horizontal axis, and notice provided to the user of how the frequency of arrhythmia detection transitioned over time. If the apparatus is designed to display a histogram showing the number of times arrhythmia occurs during each cycle of change in the biorhythms, i.e., monthly, weekly, daily, then it is possible to more accurately grasp the condition of the user's body. An example of a displayed histogram is shown in FIG. 43. For example, FIG. 43A shows the number of arrhythmia over the past year, on a monthly basis. Employing this histogram, it is possible to know the trend in the change in frequency of arrhythmia events over the past one year. Naturally, it is also acceptable to display the number of arrhythmia on a daily or weekly basis, rather than on a monthly basis. FIG. 43B shows the number of arrhythmia on each day of the week. Employing this histogram, it is possible to know the trend in change in the frequency of arrhythmia events daily for the past week or the past several weeks. FIG. 43C shows the number of arrhythmia during time intervals throughout the day. Employing this histogram, it is possible to know the trend in change in the frequency of arrhythmia events during one day or several days in the past.

As shown in FIG. 44, it is also acceptable to continuously record the clock time (time stamp) at which arrhythmia is detected, with the arrhythmia detecting apparatus or an external device (explained below) referring to the recorded time of arrhythmia occurrence and displaying a data array showing the clock time at which arrhythmia was detected. Additionally, the number of times arrhythmia occurs during each cycle of change in the biorhythm may be obtained, rendered into a histogram as shown in FIG. 43, and displayed. In addition, a pulse waveform which includes an arrhythmia may be recorded after being assigned to the clock time at which the arrhythmia was detected, with the pulse waveform then displayed in response to a command from the user or a monitor. Note that FIG. 44 shows an example in which the clock times at which arrhythmia was detected are recorded sequentially in order of detection time. However, these may be recorded in any order. Of course, it is also acceptable enable the date to be arranged in an optional order, when providing notice of the data array showing the clock time of arrhythmia detection.

Further, the above-described notice processing can be executed at an optional timing. For example, the notice processing may be executed during the operation to detect arrhythmia, or may be executed in response to a command from the user or monitor. As a method for carrying out notice in parallel with the arrhythmia detection processing, there is available a method employing an interrupt using a real time clock, for example. Namely, if arrhythmia detection processing is executed using a real time clock interruption, then there is no interruption in the processing for arrhythmia detection,.even if the aforementioned notice processing is carried out.

Furthermore, the pulse waveform may be displayed as is, or after processing. In this case, the user or monitor carries out the arrhythmia determination.

It is also acceptable to compare the arrhythmia detection frequency with a threshold value, and notify the user of the difference there between, when requested or when the threshold value is exceeded. Additionally, it is acceptable to provide constant notice of body motion constancy in the second embodiment. For example, an arrangement may be considered in which an electronic sound is generated having the same period as the fundamental wave of body motion when constancy is present in the body motion. Additionally, it is also acceptable to notify the user of the average value of the frequency of the fundamental wave of body motion during the period when there is constancy in body motion, upon request from the user.

4-1. Notifying Means

Each of the preceding embodiments were explained employing a display as an example of the means for providing notice of various data. However, the following arrangements as described below may also be cited as a means for providing notice from the apparatus to a user. It is suitable to categorize these means based on the five physiological senses. Naturally, these means may be used alone or in combinations of two or more. Moreover, as will be explained below, provided that a notice means is used which does not relay on the sense of sight, for example, it then becomes possible for a period with impaired vision to understand the contents of the notice. Similarly, it is possible to provide notice to a hearing impaired period, as long as a means which does not rely on hearing is employed. Accordingly, a device may be composed which superior with respect to its use by individuals who are physically impaired.

4-1-1. Hearing

There are available notifying means relying on the sense of sound, these including means designed to inform the user of the occurrence of arrhythmia, and the results of the analysis or diagnosis thereof, or to issue a warning to a person. For example, a buzzer which sounds upon the occurrence of an event such as an arrhythmia detection, or a speaker which provides notices of various values or the details of an event by means of a voiced sound upon occurrence of an event such as arrhythmia detection or surpassing of a threshold value, may be cited. As specific examples, a means may be considered in which the person to be notified is provided with a portable pager, and notice is carried out by means of the apparatus calling the pager. When carrying out notice to a user using this kind of equipment, it is frequently desired to communicate some sort of information along with the notice. In this case, the levels of information such as pitch, volume, tone, sound, and type of music (program, etc.) may be changed in response to the details of the information to be communicated.

4-1-2. Touch

Figure 17:
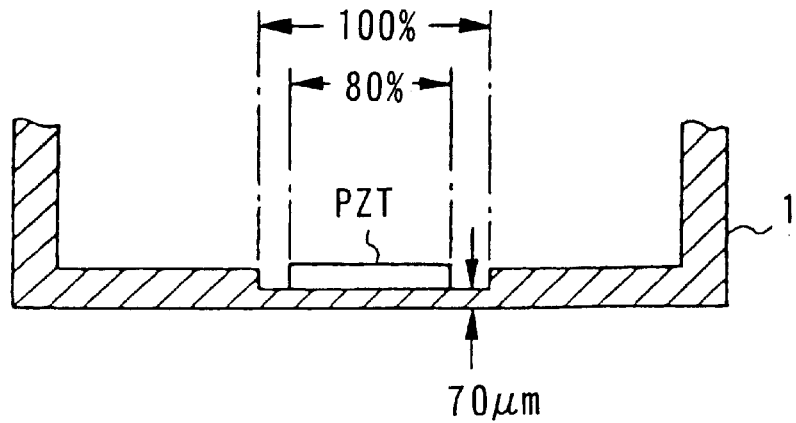
FIG. 17 is a cross-sectional view showing an example of installation in the case where a piezo element is employed as the notifying means.

A means relying on the sense of touch may also be considered as a notifying means, examples thereof including the following. First, electrical stimulation may be employed wherein a form memory alloy projecting outward from the rear surface of a portable device such a wrist watch is provided, with electricity passed through this form memory alloy. Mechanical stimulation may also be used, wherein a retractable projection (such as a needle-shaped object which is not very pointed) may be formed to the rear of a portable device such as a wrist watch, and stimulation may be administered via this projection. As another example of mechanical stimulation, an arrangement may be considered which employs a vibration alarm which communicates vibration by rotating an eccentric load, or, as shown in FIG. 17, which employs a piezoelement which is attached to a concavity formed in a portion of the inner side of the bottom surface of the main body having a thickness of 70 $\mu$m. When an alternating current of a suitable frequency is impressed on this piezoelement, the piezoelement vibrates, with this vibration communicated to the user. Accordingly, if an alternating current is impressed when arrhythmia is detected, then it is possible to provide a tactile notice of exercise intensity. Additionally, the piezoelement may have a thickness of 100 $\mu$m, with a diameter length which is 80% of the length of the diameter of the concavity.

Since it is possible to communicate a warning to the user with certainty in the case of a notifying means which uses a sense of touch, this means is suitably employed in combination with or in place of the above-described notifying means employing the sense of hearing. As a result, when arrhythmia occurs frequently during sleep, such that the frequency of thereof reaches a dangerous state, the user may be awakened so that he can take counter measures such as the administration of medication.

4-1-3. Sight

A means relying on sight may be employed when the objective is to inform the user of various measured results or messages from the device, or to provide a warning. The following equipment may be considered as such types of means: display device, CRT (cathode ray tube display device), LCD (liquid crystal display), printer, X-Y plotter, lamp and so on. Additionally, a lens projector is also available as one type of specialized display device. Further, the following variations may also be considered when providing notice: separate analog or digital displays in the case of notice involving numerical values, a display using a graph, addition of contrast to a display color, a bar graph display in the case of notice of a numerical value as is or when applying a grade to a numerical value, a pie chart graph, a face chart and so on.

Figure 18:
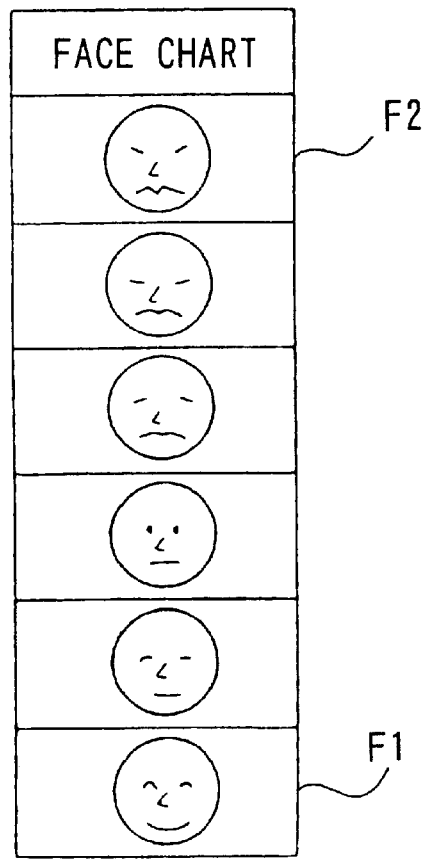
FIG. 18 shows a face chart which may be employed as a modification in each of the embodiments of the present invention.

FIG. 18 shows an example of a face chart. In the case where employing the face chart in this figure, then an arrangement may be considered in which the threshold value is compared and the picture indicated by F1 in FIG. 18 is displayed when the arrhythmia detection frequency is low, while the picture indicated by F2 in FIG. 18 is displayed when the arrhythmia detection frequency is high. In addition, it is also acceptable to provide notice of an arrhythmia event by means of a flashing display, an inverted display, or by a color change.

When displaying the arrhythmia detection frequency and so on, it is acceptable to display this information after applying a grade to it. For example, when displaying arrhythmia detection frequency, words such as "danger", "caution", "normal", "moderate" or "good" may be displayed on an LCD. In this case, the letters A, B, C, D, and E may be applied as grades to each of these displays, respectively, with these symbols then displayed on an LCD and so on.

4-1-4. Smell

A mechanism for emitting a fragrance and so on may be provided as a means relying on the sense of smell. A correspondence can be formed between the notice details and the odor, with the apparatus emitting a fragrance in response to the notice contents. A micropump and so on, is optimally employed for the mechanism for emitting fragrance and so on.

4-2. Systemization

In each of the above-described embodiments, the detected data was stored inside an arrhythmia detecting apparatus embodied in the form of a wristwatch. Accordingly, the user or monitor can display and analyze desired data by manipulating various switches on the apparatus. Where the apparatus is realized in the form of a wristwatch, however, there are limits to the size of the display, the memory capacity, the CPU processing capability, the operability of the command input means, and the like. Further, it some cases it might be necessary to carry out data exchange between the apparatus and another data processing device.

Figure 19:
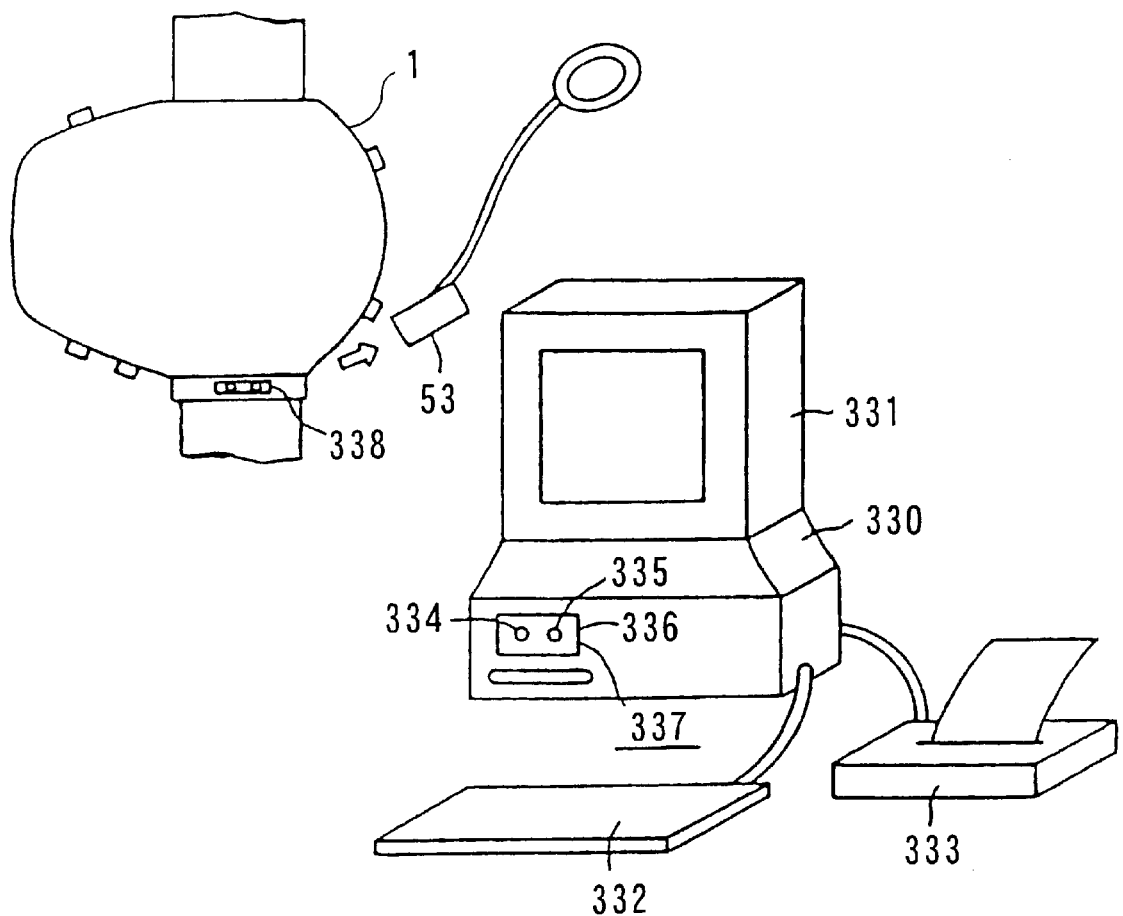
FIG. 19 shows the structure of a system employing the arrhythmia detecting apparatus according to each of the embodiments of the present invention.

An explanation of the communication means for carrying out communication between the arrhythmia detecting apparatus and an external piece of equipment will now be explained with reference to FIG. 19. As shown in the figure, the personal computer is composed of a main body 330, display 331, key board 332, and printer 333. Since this is an ordinary personal computer, an explanation of the internal structure thereof will be omitted with the exception of the following points.

Namely, main body 330 contains transmission and receiving controllers (not shown) for sending and receiving photo signal data. The transmission controller has a LED 334 for transmitting a photo signal, and the receiving controller has a phototransistor 335 for receiving a photo signal. An infrared type device using near infrared (for example, medium wavelengths of around 940 nm) is employed for LED 334 and phototransistor 335, and carries out optical transmission from a transmission window 337 for transmitting light which is provided to the front surface of main body 330, via a visible light cutting filter 336 which blocks visible light.

The arrhythmia detecting apparatus connected to the personal computer has the structure shown in FIGS. 2 and 3. As described above, a connector 53 is formed in a detachable manner to device main body 1 of the wrist watch. Accordingly, transmission is possible by attaching a communications connector 338 to the connector portion from which the connector 53 has been removed. Similarly, the LED, phototransistor, and interface for optical communication are incorporated to communication connector 338 on the computer side. Further, an optical interface (not shown) for optical communications may be provided inside device main body 1 of the wrist watch.

In order to send the various information stored in the computer's RAM or hard disk to the arrhythmia detecting apparatus from the computer, a transfer command is charged from key board 332, for example. As a result, the information in the personal computer is output via LED 334 and communication window 337 as near infrared light. The near infrared light is thus sent to the optical interface of the arrhythmia detecting apparatus via communication connector 338.

When various information is sent to the personal computer from the arrhythmia detecting apparatus, the direction of communication is the reverse of that described above. In other words, the user of the arrhythmia detecting apparatus operates the button switches provided on the apparatus main body in order to set the device to the mode for transferring data. As a result, the information which the processor inside the apparatus is to transfer is read out from RAM and so on, and sent to the optical interface. Thus, the measured value is converted to an photo signal, sent from communication connector 338, and transferred to the personal computer via communication window 337 and phototransistor 335.

Naturally, it is acceptable to design the present invention without providing a data transmission mode, so that data transmission from the arrhythmia detecting apparatus to the external device, or from the external device to the arrhythmia detecting apparatus, is automatically initiated when a specific signal is received from an external device via the interface. Additionally, it is also acceptable to provide both a data transmission mode and a function for automatically initiating data transmission, with the user or monitor able to select one of these modes.

A design is also acceptable in which, when a real time clock can be employed, as in this example, the data (time clock data) output from the real time clock is monitored, and the arrhythmia detecting apparatus requests that communications be initiated at each elapse of a specific time duration. In this case, provided a suitable reply signal is obtained, then data transmission is initiated. If a suitable reply signal is not obtained, however, then a request is again made after the elapse of a specific time period by the arrhythmia detecting apparatus to initiate communications. Further, as will be explained below, it is also acceptable to provide a design wherein, when an urgent event occurs, such as when the detected arrhythmia exceeds a preset threshold value or a determination is made that the heart has stopped, then that event serves as a trigger causing the arrhythmia detecting apparatus to immediately request that communications be initiated. In this case, if an appropriate reply signal is obtained, then data transmission begins. If an appropriate reply signal is not obtained, however, then a request is again made after the elapse of a specific time period, which corresponds to the degree of urgency, by the arrhythmia detecting apparatus to initiate communications.

When carrying out optical communication as above, in the case where it is not possible to identify which device has transmitted the information, it sometimes occurs that information which should be received by a different device is mistakenly received. Therefore, the I/O interface means employs identification information showing which equipment sent the information when information is sent or received. This identification information is stored in a ROM (not shown) inside the apparatus main body 1, for example, and communicates with an external device when communications are initiated.

By enabling communications with an external device in this way, it is not only possible to transfer information form the arrhythmia detecting apparatus to the external device, but also to carry out various settings and commands from the external device to the arrhythmia detecting apparatus.

For example, the external device may be set up under the supervision of a monitor, such as a physician. The monitor can then input into the external device a threshold value (200 times/day, for example) or allowed range (±5%) depending on the user of the arrhythmia detecting apparatus. The threshold value or allowed range are stored in the external device after creating an association between the threshold value or allowed range and the identification information for the arrhythmia detecting apparatus, and setting can be carried by transmission from the external device to the arrhythmia detecting apparatus. Further, it is also acceptable to store the identification information for the arrhythmia detecting apparatus in the external device in the case where relaying detection data from the arrhythmia detecting apparatus to the external device. If the external device is a personal computer, then it is possible to employ an external recording device having sufficient memory, a high speed CPU, software for various types of data analysis, processing and management, a display capable of outputting a large amount of data in an easily to view manner, printer, and the like. Thus, the trouble and effort associated with analysis of cumulative data is significantly reduced for the monitor.

Note that when the speed of data transmission with respect to the data quantity to b transferred is slow, then the data may be sent after first compressing it. Further, the communication interface between the arrhythmia detecting apparatus and the external device is not limited to an optical interface, but may also be an electrical interface such as an RS-232C, or an interface which employs electric waves as the transmission medium. Further, if an external device capable of communication with an arrhythmia detecting apparatus is provided on the user's side, and an interface is provided to this device and to an external device on the monitor's side which is capable of communication via a specialized circuit or public lines, then it is not necessary for the user to remain under the supervision of the monitor, but rather detected data can be relayed via the specialized circuit or public lines. Naturally, in this case, data transmission and setting in the reverse direction is also possible. When carrying out the sending and receiving of signals in this way, then a function for providing notice of the details of the transmission data and information which can specify the data's transmission source should be provided. In particular, when remote setting of the allowed range (±5%) or the threshold value (200 times per day, for example) in the arrhythmia detecting apparatus on the user's side is carried out from the external device on the monitor's side, then received data should be used to notify the user of the fact that the threshold value and allowed range are being set, using received data, irrespective of the setting details. It is also acceptable to provide a design in which the arrhythmia detecting apparatus sends the threshold value or allowed range established during remote setting back to the monitor's side. The external device on the monitor's side then compares the data sent to the arrhythmia detecting device with the data actually set on that end, and confirms that the settings have been correctly carried out.

In the case where data is to be sent quickly to the monitor in the preceding embodiments, a situation may be considered in which this rapid transmission is not possible because the user cannot move, forgets or is in a distant location. Accordingly, a function may be provided to the arrhythmia detecting apparatus for automatically sending detection data and so on to an external device on the monitor's side in the case of an emergency. As a result, in emergencies such as the user's heart stopping, or the frequency of arrhythmia exceeding a specific value, for example, the monitor is notified of this fact and provided with the detected data. Thus, the monitor can refer to the detected data,.and take such counter measures such as confirming the user's state or restricting his activities.

Further, it is acceptable to set the threshold or other maintenance value in the external device on the monitor's side only. In this case, if the user himself changes the threshold value, for example, then it is possible to avoid a situation in which the monitor is not automatically informed of this fact, even in the case where the monitor side must be informed very quickly. The opposite arrangement may be realized in the same manner.

A design is also possible in which directions from the monitor are communicated to a user at a remote location. As a result, in the case where, for example, the user is running at a remote location, and the detection data indicates to the monitor that the arrhythmia frequency in the user has exceeded a threshold value, then the monitor manipulates the external device on his end to send a direction to reduce running pitch to the user's arrhythmia detecting apparatus at the remote location. Thus, the user is also made aware of the situation. Moreover, in the case of a deterioration in the condition of a patient being cared for at home, the physician is able to quickly provide appropriate direction to the patient (user) or care giver.

Naturally, the relay of detection data to the external device on the monitor's side is not limited to emergencies only. Rather, a real time clock may be employed to regularly relay the detected data to the external device on the monitor's side. When constantly sending the detected data to the monitor's external device, the arrhythmia determination may be made by the external device, with the results of this determination sent by the external device to the user's device.

Regarding the pulse waveform frequency analysis method, methods such as maximum entropy, wavelet transformation and the like may be considered, in addition to FFT. An explanation will now be made with reference to the figures of an embodiment in which the arrhythmia detecting apparatus employs the wavelet transformation method, which is a time frequency analysis method.

Figure 20:
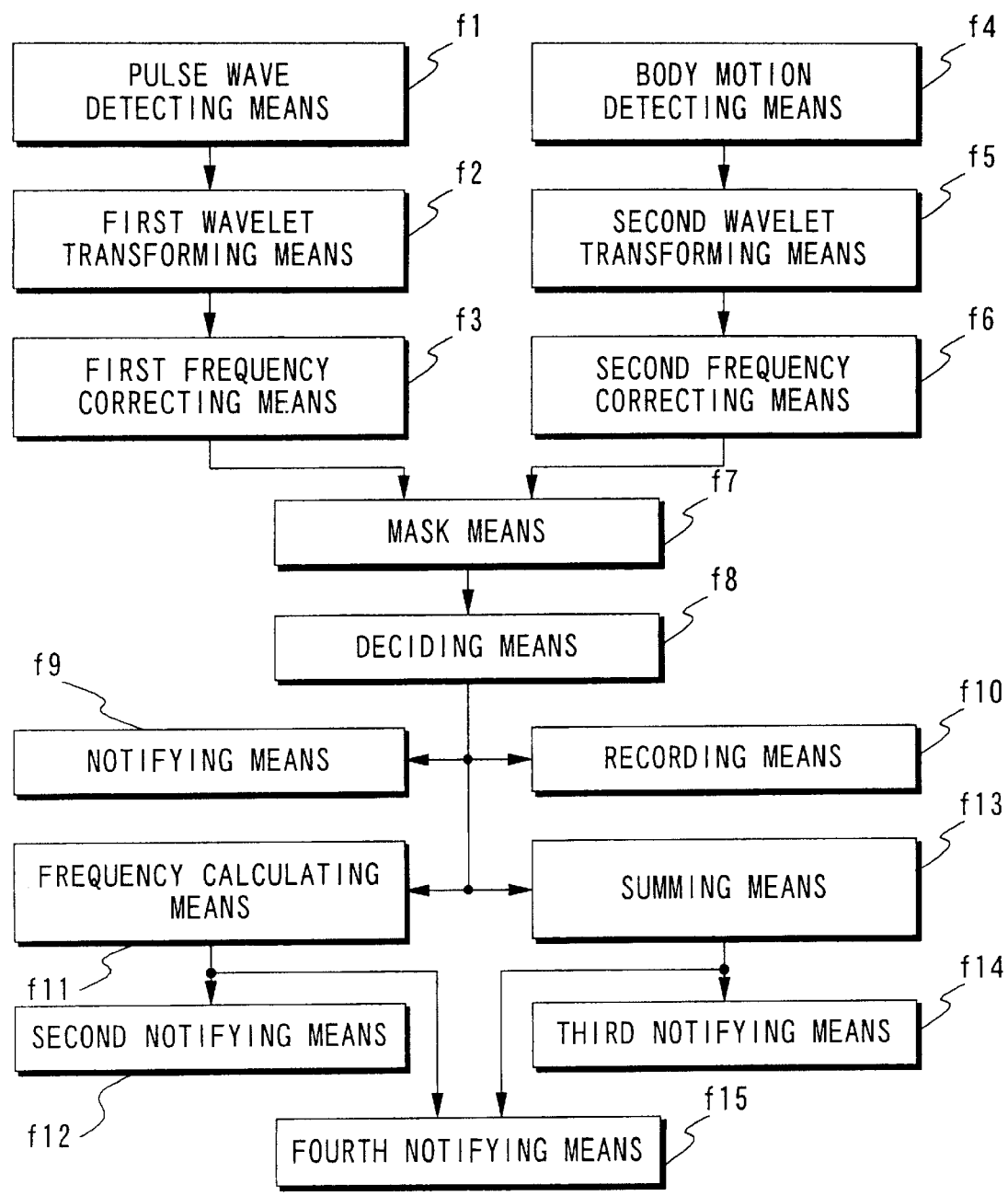
FIG. 20 is a functional block diagram for the arrhythmia detecting apparatus according to the third through fifth preferred embodiments of the present invention.

5. Functional Structure of an Embodiment for an Arrhythmia Detecting Apparatus Employing the Wavelet transformation Method The functional structure of an embodiment of a pulse wave detecting apparatus which employs the wavelet transformation method will first be explained, with reference given to the accompanying figures. FIG. 20 is a functional block diagram of the pulse wave detecting apparatus according to the present embodiment. In this figure, f1 is a pulse wave detecting means which detects the pulse waveform. The pulse waveform is detected by applying pressure on the radius artery via the skin, for example. f2 is a first wavelet transforming means which performs wavelet transformation to the pulse waveform detected by the pulse wave detecting means f1, and generates pulse wave analysis data for each frequency region. f3 is a first frequency correcting means, which performs correction on the pulse wave analysis data based on the corresponding frequencies, so that the power density per frequency becomes constant. f3 then generates corrected pulse wave data. As a result, wavelets detected in different frequency regions can be compared.

Next, f4 is a body motion detecting means, which detects body motion and outputs a body motion waveform. As a result, it is possible to detect when the individual is moving. f5 is a second wavelet transforming means which performs wavelet transformation on the body motion waveform detected by body motion detecting means f4, and generates body motion analysis data for each frequency region. f6 is a second frequency correcting means which performs correction on the body motion analysis data based on the corresponding frequencies, so that the power density per frequency becomes constant. f6 then generates corrected body motion data. Since frequency correction has been performed, it is thus possible to compare the thus-calculated corrected body motion data and the corrected pulse wave data.

f7 is a mask means which subtracts the corrected body motion data from the corrected pulse wave data, and generates corrected pulse wave data from which body motion has been removed. f8 is a deciding means which decides that arrhythmia has occurred when an anomalous portion is detected by analyzing the continuity of the corrected pulse wave data generated by mask means f7 in each frequency region.

When carrying out arrhythmia detection while the subject is in a state of sleep or repose, it is not necessary to carry out body motion detection. Accordingly, body motion detecting means f4, second wavelet transforming means f5, second frequency correcting means f6, and mask means f7 may be omitted. Further, a frequency correcting means may be provided at a subsequent to mask means f7, in place of first frequency correcting means f3 and second frequency correcting means f6, so that the structure is simplified. It is also acceptable to omit all of the frequency correcting means.

f9 is a notifying means which provides notice that arrhythmia has been determined by deciding means f8. As a result, the user or a third party such as a physician is able to confirm the presence or absence of arrhythmia. f10 is a recording means which records the clock time at which an arrhythmia event occurred when deciding means f8 decides that arrhythmia has occurred. Accordingly, it is possible to know after the fact what time the arrhythmia event occurred. f11 is a frequency calculating means which calculates the number of times in a specified period of time that deciding means 8 determines arrhythmia, and defines this as arrhythmia frequency information. f12 is a second notifying means which provides notice when the arrhythmia frequency information exceeds a specified value predetermined in advance. As a result, an individual suffering from heart disease can be informed should his condition become dangerous, so that he take appropriate counter measures such as administering medication.

f13 is an adding means which generates arrhythmia sum information by adding the number of times that deciding means f8 determines arrhythmia. f14 is a third notifying means which provides notice when the arrhythmia sum information exceeds a predetermined specified value. As a result, the user is able to know when a deterioration in his physical condition has occurred.

f15 is a fourth notifying means which provides notice when the arrhythmia frequency information exceeds a predetermined specified value and the arrhythmia sum information exceeds a predetermined specified value. As a result, it is possible to even more accurately inform the user or monitor when the user's condition has entered a dangerous state.

6. Third Embodiment 6-1. Structure of the Third Embodiment

The structure of the arrhythmia detecting apparatus according to the third embodiment of the present invention will now be explained with reference to the accompanying figures.

6-1-1. Outer Structure of the Third Embodiment

Figure 21:
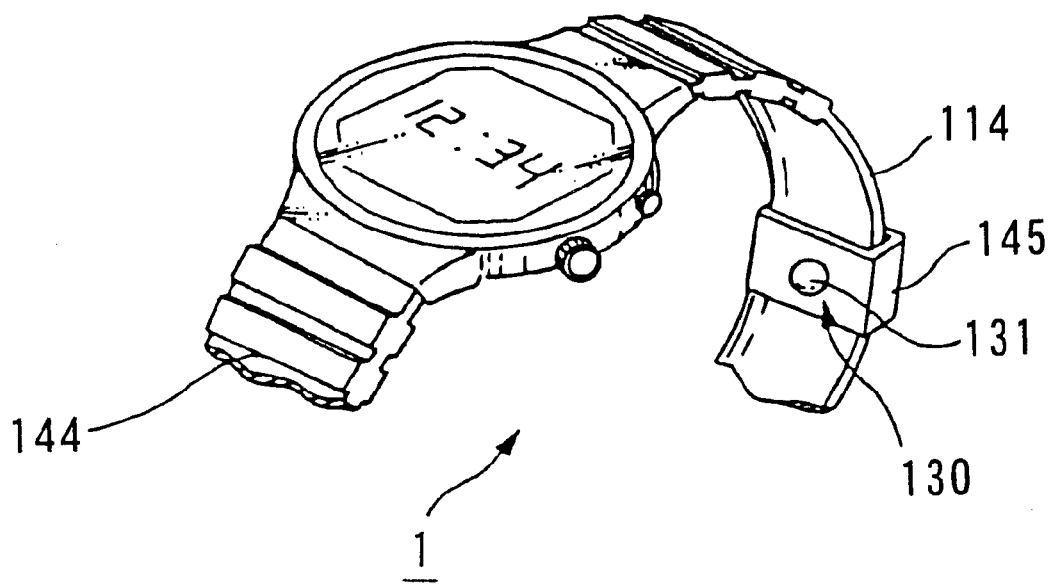
FIG. 21 is a slant view of the arrhythmia detecting apparatus according to the third embodiment of the present invention.

FIG. 21 is a slant view showing the outer structure of the arrhythmia detecting apparatus according to the third embodiment of the present invention. As shown in this figure, arrhythmia detecting apparatus 1 is designed in the form of a wristwatch. Arrhythmia detecting apparatus 1 is provided with a pair of bands 144,144. As shown in the figure, the elastic rubber 131 of pressure sensor 130 projects outward from the fastening side of a belt-shaped fastener 145 which is provided to one of bands 144,144. Although not shown in detail in the figure, the band 144 provided with belt-shaped fastener 145 has a structure wherein the FPC (flexible printed circuit) substrate which is to supply the detection signal from pressure sensor 130 is coated with a soft plastic.

Figure 22A:
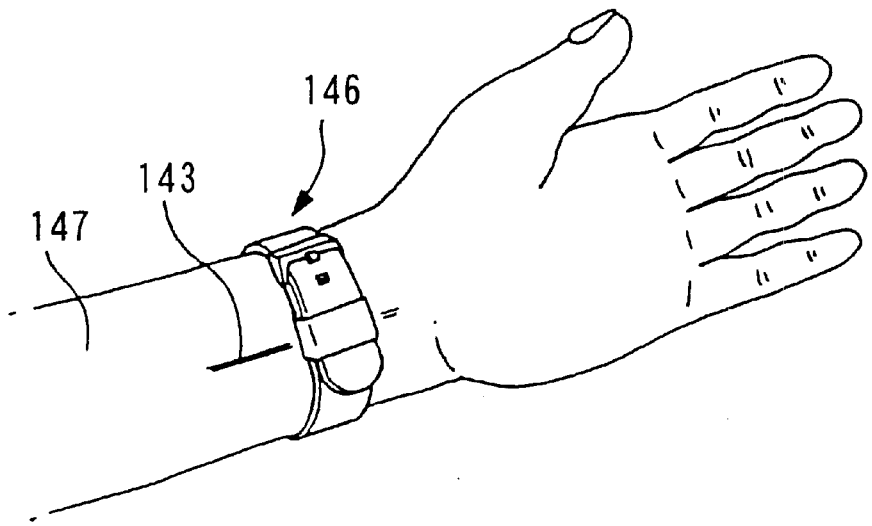
FIGS. 22A and 22B are explanatory figures showing the state of the arrhythmia detecting apparatus according to this embodiment at the time of use.
Figure 22B:
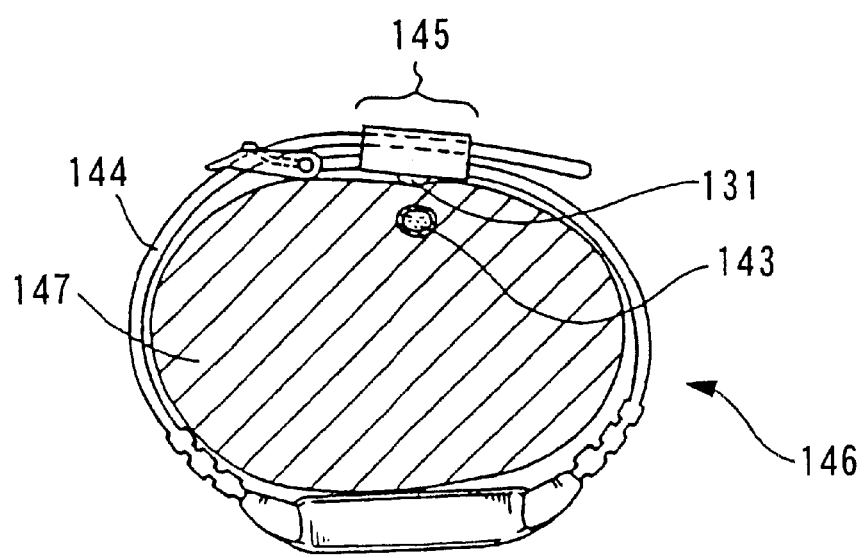

A principal component having a electrical structure which analyzes the pulse wave is incorporated in arrhythmia detecting apparatus 1. Additionally, a display is also provided in the apparatus. As shown in FIGS. 22A and 22B, when in use, wristwatch 146 is wrapped around the left wrist 147 of a test subject so that the elastic rubber 131 provided to belt-shaped fastener 145 is positioned in the vicinity of radius artery 143, enabling constant detection of the pulse wave. Further, the operation to wrap this device around the arm of the user is equivalent to that when using an ordinary wrist watch.

When elastic rubber 131 is pressed against the vicinity of the subject's radius artery 143, the changes in blood flow (i.e., pulse wave) are communicated to the pressure pulse wave sensor 130 via elastic rubber 131, and are detected as blood pressure by pressure pulse wave sensor 130.

6-1-2. Electrical Structure of the Third Embodiment

The electrical structure of an arrhythmia detecting apparatus will now be explained with reference to FIG. 23. FIG. 23 is a block diagram showing the electrical structure of an arrhythmia detecting apparatus.

Arrhythmia detecting apparatus 1 is composed of the following parts. Namely, 10 is a wavelet transform element, which performs conventional wavelet transformation on the pulse waveform MH output from pressure pulse wave sensor 130, and generates pulse waveform analysis data MKD.

In general, in time frequency analysis in which the signal is simultaneously analyzed in both the time and frequency domains, the wavelet forms are the unit by which the signal part is extracted. Wavelet transformation shows the size of the each part of the signal extracted as these units. As the base function for defining wavelet transformation, a function $\psi(x)$ which has been localized with respect to both time and frequency is introduced as the mother wavelet. Here, wavelet transformation employing the mother wavelet $\psi(x)$ of a function f(x) is defined as follows.

$$(W_\psi f)(b, a) = \int_{-\infty}^{\infty} \frac{1}{\sqrt{a}} \psi\left(\frac{x-b}{a}\right) f(x) dx$$

In equation 1, b is the parameter employed when translating the mother wavelet $\psi(x)$, while a is the parameter used when scaling. Accordingly, wavelet $\psi((x-b)/a)$ in equation 1 is the wavelet obtained when transitioning mother wavelet $\psi(x)$ by b only, and scaling it by a only. Since the width of the mother wavelet $\psi(x)$ is extended in correspondence to the scale parameter a, 1/a corresponds to the frequency. The detailed structure of wavelet transform element 10 will be explained below.

Frequency corrector 11 carries out frequency correction on pulse wave analysis data MKD. When comparing data from different frequency regions, it is necessary to correct for the effect of the term $[1/a^{1/2}]$ corresponding to frequency in the preceding equation 1. Frequency corrector 11 is provided for this purpose. Namely, frequency corrector 11 generates corrected pulse wave data MKD' by multiplying wavelet data WD by a coefficient $a^{1/2}$. As a result, it is possible to carry out correction based on each of the corresponding frequencies, so that the power density per frequency becomes constant.

Next, decision element 12 detects arrhythmia based on corrected pulse wave data MKD', and generates arrhythmia detection information FD. The structure of decision element 12 will be explained in detail below. Display 13 is composed of a ROM, control circuit, LCD display and the like. Arrhythmia detection information FD is supplied to display 13. The control circuit detects this, reads out characters stored in ROM, and displays these on the liquid crystal display. Letters spelling out "arrhythmia", or specific symbols or icons, may be used. As a result, the user or physician is notified that arrhythmia has occurred.

The number 14 indicates a RAM. The clock time at which the arrhythmia detection information FD was generated is sequentially stored in RAM 14. This clock time is read out from RAM 14 when an operational part, not shown in the figures, is manipulated, and is displayed on display 13. As a result, it is possible to know after the fact the time at which the arrhythmia occurred, which is useful in diagnosis. Additionally, it is acceptable for this clock time to be sent to an external device (such as a personal computer) via an interface not shown here. In this case, a more precise analysis and diagnosis of arrhythmia can be carried out. Please note that the system disclosed in section 4-2 entitled "Systemization" can be employed as is, or with only slight modification, for the systemization of the external device and the arrhythmia detecting apparatus according to the third embodiment, and to the fourth and fifth embodiments which will be explained below. Accordingly, an explanation will be omitted here.

Next, summer 15, which is provided with an internal memory and comparator, adds the number of times arrhythmia detection information FD was generated, generates arrhythmia summed data FSD which indicates the summed value, and stores this information in the internal memory. When the operational portion not shown in the figures is manipulated, arrhythmia summed data FSD which is stored in the internal memory is reset, or the arrhythmia summed data FSD at the time of manipulation of the operational portion is read out and displayed on display 13. A predetermined threshold value is set in internal memory, and is compared to the arrhythmia summed data FSD by the comparator. When the arrhythmia summed data FSD exceeds the threshold, then the comparator generates first warning information KD1. When first warning information KD1 is supplied to buzzer 17, buzzer 17 sounds, thereby notifying the user that he is in a dangerous physical condition.

As discussed above, arrhythmia may indicate a serious condition, or one in which the danger is only very small, depending on its cause. Arrhythmia summed data FSD is useful for knowing the extent of a person's health. It is known that arrhythmia which occurs accompanying serious cardiac or vascular disease may appear 200 times or more per day even when there is only a single cause, and may display an electrocardiogram of a variety of forms in the case where there are multiple causes for the arrhythmia. Accordingly, if the threshold is set at 200 times, for example, then a first warning information KD1 is generated each time this value is exceeded, and a buzzer is sounded to notify the user. In this was, a warning is provided to the user.

The number 16 is a frequency calculator. Frequency calculator 16 is provided with an internal memory and a comparator, and generates arrhythmia frequency information FHD by counting the number of times that arrhythmia detection information FD is generated per unit time. This arrhythmia frequency information FHD is displayed on display 13 when the user manipulates the operational portion. A predetermined threshold value is set in the internal memory, with frequency calculator 16 designed to compare this threshold value with the arrhythmia frequency information FHD. When the arrhythmia frequency information FHD exceeds the threshold value, then second warning information KD2 is generated. When second warning information KD2 is supplied to buzzer 17, then buzzer 17 sounds, notifying the user that he is in a dangerous physical condition.

The display of arrhythmia frequency information FHD on display 13 is useful in enabling the user to manage the state of his own health. The sounding of buzzer 17 when arrhythmia occurs frequently during sleep, or when the arrhythmia frequency information FHD exceeds a threshold value indicating that the user's condition has fallen into a dangerous state, is useful for notifying the user of the danger.

6-1-3. Wavelet transform element

The structure of wavelet transform element 10 will be explained in detail using the figures. FIG. 24 is a block diagram of the wavelet transform element 10 according to the third embodiment.

Figure 25B:
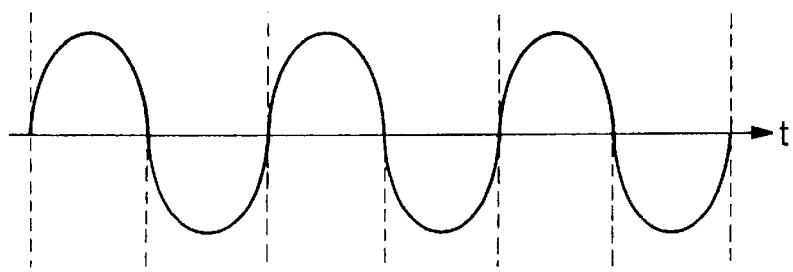

In this figure, ringing filter 101 is a filter with a high Q value having a central frequency of 2.2 Hz and a pass band of 0.8 to 3.5 Hz. The fundamental wave component of the pulse waveform is typically in the range of 0.8 to 3.5 Hz. Thus, when pulse waveform MH passes through ringing filter 101, that fundamental wave component is extracted. For example, when the pulse waveform MH shown in FIG. 25A passes through ringing filter 101, then the sinusoidal wave shown in FIG. 25B is obtained.

Figure 25C:
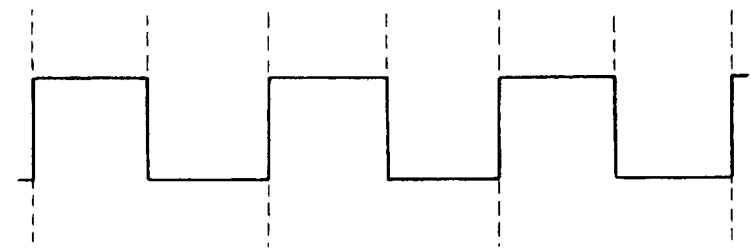

Zero cross detecting circuit 102 is composed of a comparator and so on. Zero cross detecting circuit 102 compares the output signal and grand level of ringing filter 101, and generates a rectangular wave. This rectangular wave is synchronized with heart beat. For example, if the output signal of ringing filter 101 is as shown in FIG. 25B, then the output signal of zero cross detecting circuit 102 becomes as shown in FIG. 25C.

Next, frequency dividing circuit 103 divides in half the signal output from zero cross detecting circuit 102, and generates a control signal CS shown in FIG. 25D. One high level or low level period of this control signal CS corresponds to the interval of one heart beat.

Next, pulse waveform MH is converted to a digital signal by A/D converter 104, and then stored in first memory 105 and second memory 106. Control signal CS is directly supplied to the light enable terminal of first memory 105, and is supplied to the light enable terminal of second memory 106 after being inverted by inverter 107. Pulse waveform MH is alternately stored in first and second memory 105, 106 in heartbeat units. Further, multiplexer 108 selects pulse wave data MD read out alternately from first and second memory 105 and 106, and outputs this to base function developer W. Pulse wave data MD is read out from second memory 106 during the write period of first memory 105, and written to second memory 106 during the read out of first memory 105.

Base function developer W is designed to carry out the calculations for the preceding equation (1) above, and is composed of a base function recorder W1 which records the mother wavelet ψ(x); a scale converter W2 which converts scale parameter a; buffer memory W3; parallel translator W4 which carries out translation; and multiplier W5. Please note that various types of wavelets may be suitably employed for mother wavelet ψ(x) which is stored in base function recorder W1, including Gabor wavelet, Mexican hat wavelet, Harr wavelet, Meyer wavelet, Shannon wavelet and the like.

When a mother wavelet ψ(x) is read out from base function recorder W1, conversion of scale parameter a is carried out by scale converter W2. Scale parameter a corresponds to period, thus, the bigger a is, the more the mother wavelet extends above the time axis. In this case, the quantity of data for mother wavelet ψ(x) recorded in base function recorder W1 is fixed, so that when a gets larger, the amount of data per unit time decreases. Scale converter W2 carries out interpolation to correct this, and generates a function ψ(x/a) by performing weeding out processing when a gets smaller. This data is stored once in buffer memory W3.

Next, parallel translator W4 reads out function ψ (x/a) from buffer memory W3 at a timing in response to translation parameter b, carrying out the parallel transition of function ψ(x/a), to generate a function ψ(x−b/a).

Next, multiplier W4 multiplies variable $1/a^{1/2}$, function ψ(x−b/a) and pulse wave data MD, and carries out wavelet transformation in heartbeat units. In this way, pulse wave analysis data MKD is generated. In this example, pulse wave analysis data MDK is segregated into the frequency regions 0 Hz~0.5 Hz, 0.5 Hz~1.0 Hz, 1.0 Hz~1.5 Hz, 1.5 Hz~2.0 Hz, 2.0 Hz~2.5 Hz, 2.5 Hz~3.0 Hz, 3.0 Hz~3.5 Hz, and 3.5 Hz~4.0 Hz, and output.

6-1-4. Decision element

Figure 26:
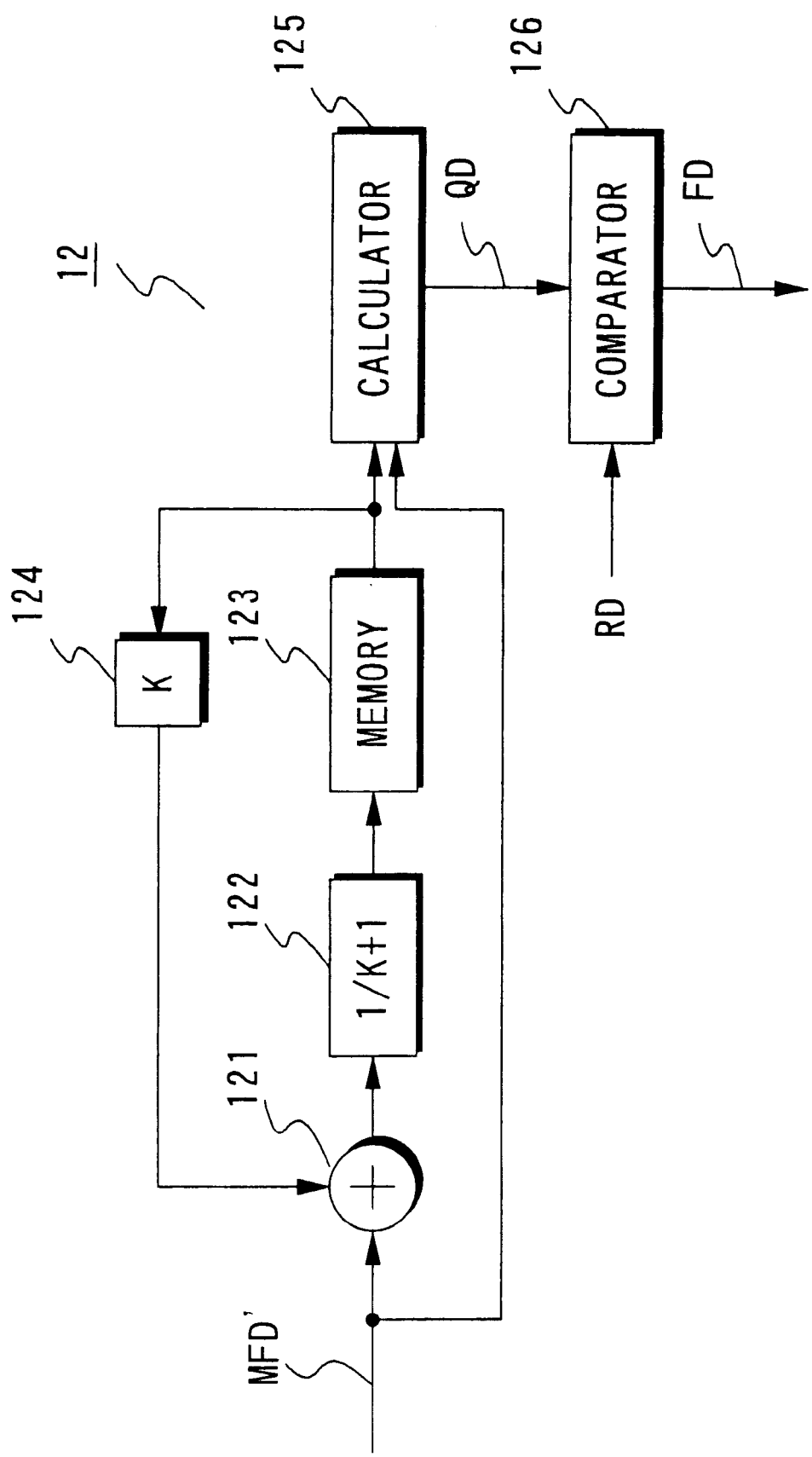
FIG. 26 is a block diagram showing the detailed structure of the decision element according to this same embodiment.

Next, decision element 12 will be explained. FIG. 26 is a block diagram of decision element 12 according to the present embodiment.

In the figure, adder 121, coefficient circuits 122 and 124, and memory 123 are circuits for calculating the average value of corrected pulse wave data MKD' in each frequency region. The coefficient of coefficient circuit 122 is 1/K+1, while the coefficient of coefficient circuit 124 is K. Adder 121 adds the outputs from corrected pulse wave data MKD' and coefficient circuit 124. The data output from adder 121 is stored in memory 123 via coefficient circuit 122. The preceding processing is carried out each time a corrected pulse wave data MKD' is generated, in synchronization with the period of the heart beat. Accordingly, the contents of memory 123 are renewed in synchronization with heart beat.

Here, if the period of the heart beat is t, the current clock time is T, and the data stored in memory 123 is Ma, then data Ma(T) at clock time T may be obtained by the following equation.

$$Ma(T)=\{Ma(T-t)*K+MKD'(T)\}/(K+1)$$

Figure 27:
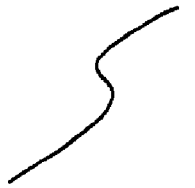
FIG. 27 shows the details of memory 124 according to this same embodiment.

Ma(T−t) in this equation is data obtained at an interval of time t ago, i.e., showing the data from the previous heart beat. Accordingly, data Ma(T) is the weighted average of a past data and the current data. Since this processing is repeated at every interval of time t, the result is that the average value of corrected pulse wave data MKD' is stored in memory 124. Since corrected pulse wave data MKD' is generated in each frequency region, the average is calculated in each frequency region. For this reason, the average values Ma1~Ma8 of corrected pulse wave data MKD' by units of 0.5 Hz is stored in memory 124, as shown in FIG. 27. In this sense, then, memory 124 functions as an average value table.

Next, calculator 125 carries out calculations for evaluation function Q(T) expressed by the following formula, and outputs this as evaluation data QD.

$$Q(T) = \sum Pk \cdot |Mak(T) - Mk(T)|/Mak(T)$$
$$= P1 \cdot |Ma1(T) - M1(T)|/Ma1(T) +$$
$$P2 \cdot |Ma2(T) - M2(T)|/Ma2(T) + \ldots +$$
$$P8 \cdot |Ma8(T) - M8(T)|/Ma8(T)$$

However, Mk(T) is each frequency component of corrected pulse wave data MDK' at clock time T, where k=1~8. Pk is a coefficient which becomes 1 when Mak(T) exceeds a predetermined threshold value, and becomes 0 when Mak(T) is below the threshold. The coefficient is set in this way because it is possible to discriminate whether or not arrhythmia has occurred based on the characteristic portion of the pulse waveform, since this portion has a large energy. On the other hand, when the discrimination of arrhythmia is made based on the portion where the level is low, then the SN ratio is poor. Thus, accurate discrimination cannot be carried out.

For this reason, evaluation function Q(T) indicates the extent to which the corrected pulse wave data MDK' deviates from the average value. Comparator 126 compares the evaluation data QD and the reference data RD, and generates arrhythmia detection information FD when evaluation data QD exceeds reference data RD. Please note that in this embodiment, a value calculated in experiments so that a determination of arrhythmia could be made is used for the value of reference data RD. Reference data RD is set with a certain amount of leeway, so that a non-arrhythmic pulse wave is not mistakenly determined to be an arrhythmia.

It is possible to determine the frequency distribution over a short period of time in wavelet transformation. Accordingly, if the aforementioned time is set to be short, then it is possible to determine whether or not the pulse waveform over a given interval of time has a normal shape. Thus, by this method as well, pulse detection can be carried out. In this case, an advantage is offered in that it is possible to carry out a determination which combines an arrhythmia determination over a time interval and a frequency determination over a frequency region. However, arrhythmia is detected as set forth above, by comparing the reference data RD and the evaluation data QD at each period of the pulse wave. This will be the same in the following fourth and fifth embodiments.

6-2. Operation of the Third Embodiment

The operation of the third embodiment will now be explained with reference to the accompanying figures. FIG. 28 is a diagram for explaining the operation of the third embodiment.

FIG. 28A shows an example of a pulse waveform MH which is detected by pressure pulse wave sensor 130. In this example, pulse waveform MH1 from time T to time T+t is an ordinary wave. Arrhythmia occurs during the interval from time T+t and time T+2t which follows thereafter, however. The pulse is normally continuous in synchronization with the heart beat. However, if an insufficient heart rate occurs, then the crest value in pulse waveform MH2 disappears almost entirely, and an arrhythmia occurs.

During the interval from time T+2t and time T+3t, the heart again contracts and the pulse is generated. In general, it is frequently the case that peak P3 of pulse waveform MH3 occurring immediately after the arrhythmia is larger than peak P1 of a normal pulse waveform MH1, such that this makes up for the insufficiency in heart beat. Further, pulse waveform MH3 is effected by the arrhythmia, such that its position is delayed with respect to pulse waveform MH1 by a factor of ΔT. This positional delay also occurs in pulse waveform MH4. However, peak P4 in pulse waveform MH4 is roughly equivalent to peak P1 of normal pulse waveform MH1.

FIG. 28B is a waveform of the signal output from zero cross detecting circuit 102 shown in FIG. 24. As set forth above, the Q value of ringing filter 101 is set to a high value, so that the output signal is continuous even if the crest value of pulse waveform MH2 after arrhythmia occurs becomes low. Further, pulse waveforms MH3,MH4 have a positional delay of ΔT with respect to the pulse waveform of MH1, however, the phase of the output signal does not change immediately, but gradually follows as time passes. Note that in this example, the frequency of the output signal was 1.3 Hz.

When wavelet transformation is carried out in this way by wavelet transform element 10 in synchronization with the generated output signal, and pulse wave analysis data MKD is generated, then frequency corrector 11 carries out frequency correction to pulse wave analysis data MKD and generates corrected pulse wave data MKD'. FIG. 28C shows each frequency component M1~M8 of corrected pulse wave data MKD' corresponding to each of the pulse waveforms MH1~MH4, respectively. FIG. 28D shows average value data Ma1~Ma8 of corrected pulse wave data MKD' which is stored in memory 124. In this example, the average value Ma1~Ma8 does not change between the interval from time T to time T+4t.

The frequency of the output signal of zero cross detecting circuit 102 is 1.3 Hz. Thus, the frequency of the fundamental wave of pulse waveform MH is 1.3 Hz. For this reason, the value of average value data Ma1 corresponding to 1.0~1.5 Hz is [7], the maximum value. The values of average value data Ma5,Ma7 corresponding to the second and third higher harmonic waves become the next largest at [4]. On the other hand, in the case of corrected pulse wave data MKD' corresponding to an arrhythmic pulse waveform MH2, the crest value is low. Thus, the values of data M1~M8 corresponding to each of the frequency components becomes small.

FIG. 28E shows the evaluation data QD1~QD4 corresponding to each of the pulse waveforms MH1~MH4. In this example, the coefficient Pk becomes 1 in the above evaluation function $Q(T) = \Sigma Pk \cdot |Mak(T) - Mk(T)|/Mak(T)$ when Mak(T) is 4 or greater, and becomes 0 when Mak(T) is less than 4.

For example, QD2 is generated as follows by calculator 125 shown in FIG. 26:

$$QD2 = |Ma3 - M3|/Ma3 + |Ma5 - M5|/Ma5 +$$
$$|Ma3 - M7|/Ma7$$
$$= |7 - 0|/7 + |4 - 2|/4 + |4 - 0|/4$$
$$= 2.5$$

Comparator 126 compares evaluation data QD with reference data RD. In this example, the value of reference data RD is set to [1]. For this reason, pulse waveform MH2 is determined to be an arrhythmia, and pulse waveforms MH1, MH3 and MH4 are determined to be normal. FIG. 28F is an arrhythmia detection flag output from comparator 126 as arrhythmia detection information FD. A high level indicates an arrhythmia, while a low level indicates a normal pulse wave. Additionally, the delay of time t in the arrhythmia detection flag is because time is required for the processing carried out by calculator 125 and comparator 126.

When arrhythmia detection flag is detected as arrhythmia detection information FD, then a indication is made on display 13 that an arrhythmia has occurred, and the clock time of the occurrence is recorded in RAM 14. Then, the number of arrhythmia detection flags is summed by summer 15. When this value exceeds the threshold, the user is notified to this effect by a buzzer. Moreover, the buzzer may also be used to notify the user in the case where the frequency of arrhythmia occurrence per unit time exceeds a threshold value.

As a result of this third embodiment, it is possible to provide a portable arrhythmia detecting apparatus capable of accurately detecting arrhythmia by means of a simple operation. Further, because the user or third party is notified of the time at which the arrhythmia occurred, it is possible to be made aware of the occurrence of an arrhythmia even after the fact. Since the arrhythmia summed information FSD is displayed on display 13, the state of health can be readily known. Also, since buzzer 17 sounds when the arrhythmia summed information FSD exceeds a threshold, it is possible to provide a warning to the user. Additionally, since buzzer 17 sounds when arrhythmia frequency information FHD exceeds a threshold value, it is possible to avoid such severe circumstances as sudden death by taking such counter measures as the administration of medication, even in the case where the arrhythmia occurs frequently during sleep causing the user to enter dangerous condition.

7. Fourth Embodiment

The arrhythmia detection apparatus of the third embodiment assumed that the user was in a state of repose. Pulse becomes strong in an individual who is exercising, however. Thus, when the user is walking, or lifting objects, the pulse waveform will change under the influence of this movement. For this reason, it is difficult to correctly detect arrhythmia accurately with the arrhythmia detection apparatus according to the third embodiment in the case where the user is moving. Thus, the apparatus of the fourth embodiment was conceived in consideration of this point, and has as its objective the provision of an arrhythmia detecting apparatus which can accurately detect arrhythmia even in the presence of body motion, by means of canceling out the body motion component from the pulse waveform.

Figure 29:
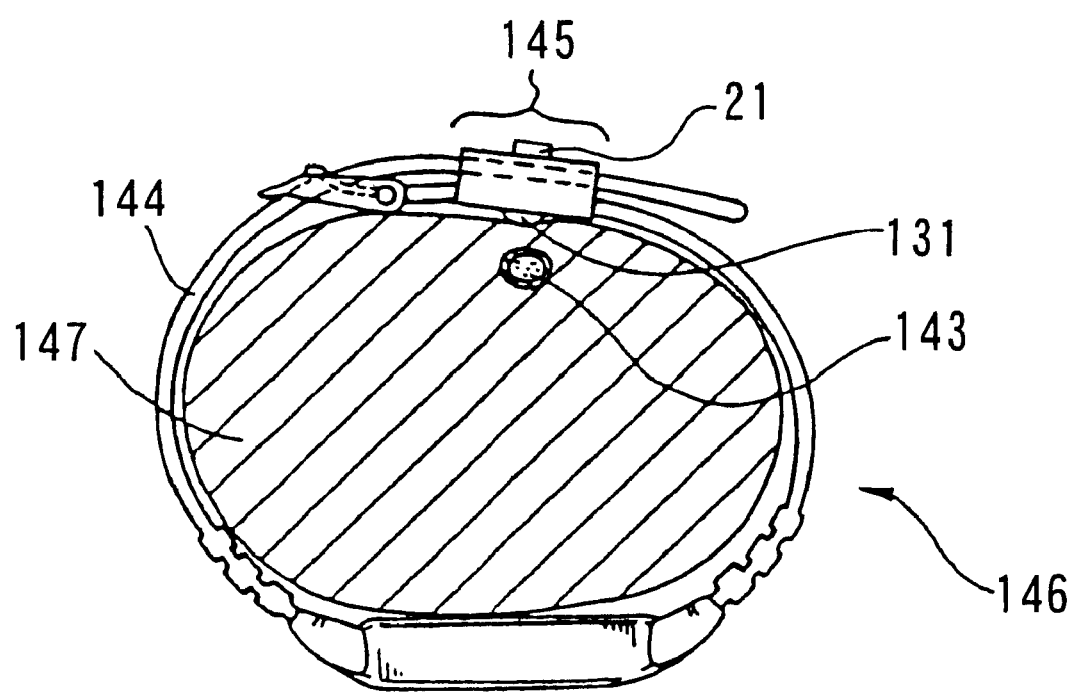
FIG. 29 is an explanatory figure showing the state of the arrhythmia detecting apparatus according to the fourth preferred embodiment of the present invention at the time of use.

7.1. Structure of the Fourth Embodiment 7-1-1. Outer Appearance of the Fourth Embodiment FIG. 29 is a diagram showing the outer structure of the arrhythmia detecting apparatus according to the fourth embodiment at the time of use. FIG. 29 differs from FIG. 22B which shows the outer structure of the third embodiment in that an acceleration sensor 21 is provided opposite elastic rubber 131 in belt-shaped fastener 145. Since acceleration sensor 21 is provided in the vicinity of pressure pulse wave sensor 130 on the lower side of elastic rubber 131 in this case, it is possible to detect body motion applied on the pressure pulse wave sensor 130 with good accuracy.

7-1-2. Electrical Structure of the Fourth Embodiment

Figure 30:
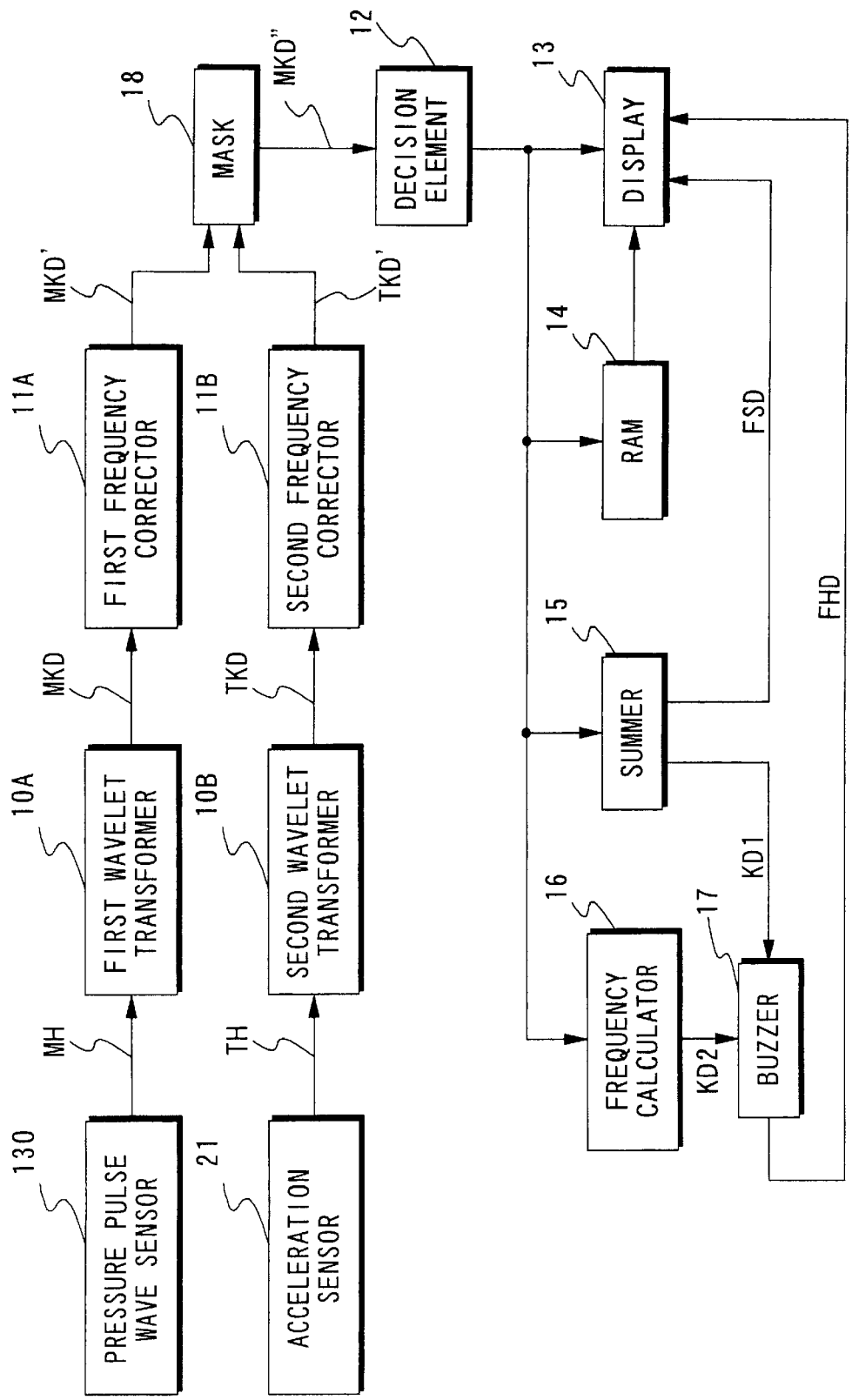
FIG. 30 is a block diagram showing the electrical structure of the arrhythmia detecting apparatus according to this same embodiment.

An explanation will now be made of the electrical structure of the arrhythmia detecting apparatus according to the fourth embodiment. FIG. 30 is a block diagram of the arrhythmia detecting apparatus according to the fourth embodiment.

First wavelet transform element 10A and first frequency corrector 11A in this figure have the same structure as the wavelet transform element 10 and frequency corrector 11 of the third embodiment, and are designed to output corrected pulse wave data MKD' from first frequency corrector 11A.

When body motion waveform TH is detected by acceleration sensor 21, this is supplied to second wavelet transform element 10B. Wavelet transformation is then carried out to the body motion waveform, to generate body motion analysis data TKD. Second wavelet transform element 10B is composed in the same was as the wavelet transform element 10 of the third embodiment. For this reason, body motion analysis data TKD is composed of each of the frequency components obtained by separating the 0~4 Hz frequency region at 0.5 Hz intervals. Second frequency corrector 11B, which has the same structure as the frequency corrector 11 of the third embodiment, generates corrected body motion data TKD' by carrying out frequency correction on body motion analysis data TKD.

Next, mask 18 subtracts corrected body motion data TKD' from corrected pulse wave data MKD', and generates corrected pulse wave data MKD" from which the body motion component has been eliminated. Decision element 12 then carries out arrhythmia determination in the same way as in the third embodiment, based on the corrected pulse wave data MKD". Display 13 and the other parts subsequent to decision element 12 have the same structure as in the third embodiment, and so will not be explained here.

7-2. Operation of the Fourth Embodiment

The operation of the fourth embodiment will now be explained with reference to the figures.

Figure 31A:
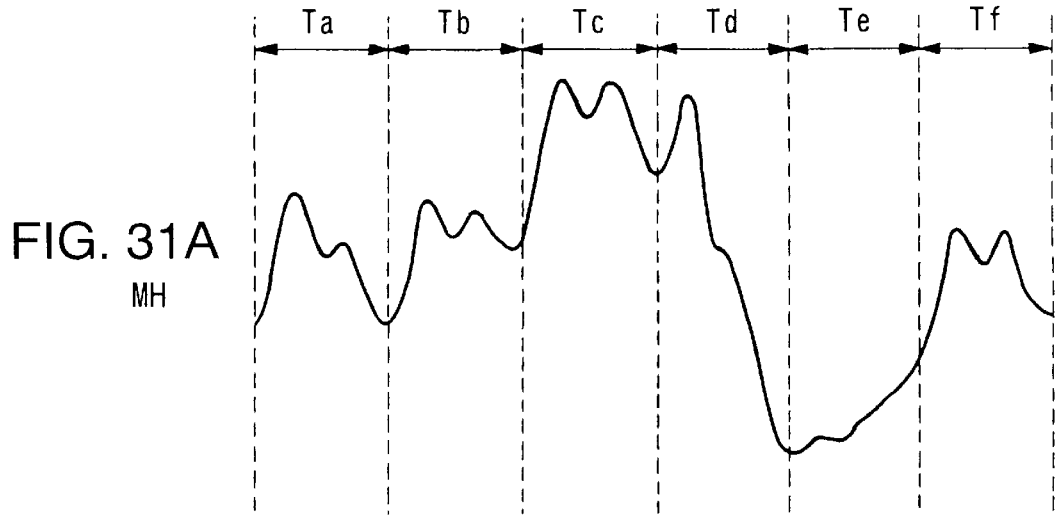
FIGS. 31A, 31B and 31C are waveform diagrams showing the body motion waveform and the pulse waveform according to this same embodiment.
Figure 31B:
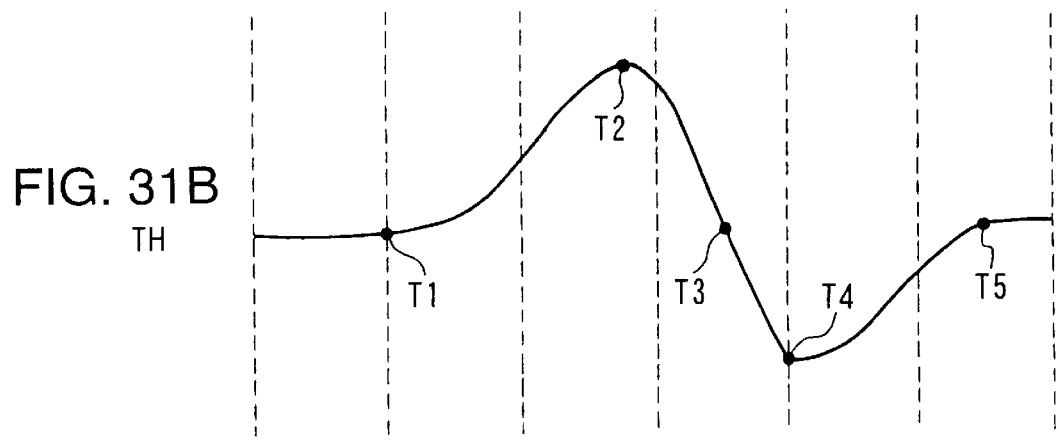

This example assumes the case in which the user lifts a cup with his hand, and then returns it to its original position during the arrhythmia detection. In this case, the pulse waveform MH shown in FIG. 31A is detected by a pressure pulse wave sensor, while the body motion waveform TH is detected simultaneously by FIG. 31B.

Body motion TH begins to increase from time T1, and reaches a positive peak at time T2. Thereafter, body motion TH gradually falls, passing through level 0 at time T2, reaching a negative peak at time T3, and returning to level 0 at time T4. Since body motion waveform TH is detected by acceleration sensor 21, time T3 corresponds to the clock time at which the cup is maximally lifted by the user, time Ti corresponds to the clock time at which the user starts to lift the cup, and time T4 corresponds to the clock time at which the lifting operation is terminated. Accordingly, the time period from time T1 to T4 is the time period during which body motion is present.

Figure 31C:
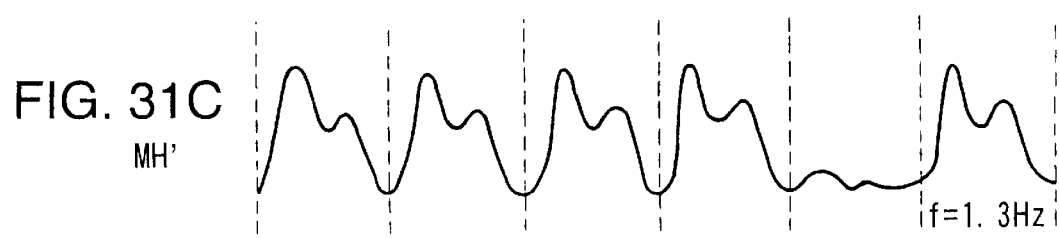

FIG. 31C is the pulse waveform MH' assuming that there is no body motion. From this figure, it may be understood that an arrhythmia occurs during the period Te, while the pulse wave during the periods Ta~Td and Tf is normal. Moreover, in this example, the frequency of the fundamental wave of the pulse waveform MH is 1.3 Hz.

Next, the operation of the arrhythmia detecting apparatus according to the fourth embodiment will be explained with reference given to FIG. 32. Note that the time periods Ta~Tf shown in FIG. 32 correspond to those shown in FIG. 31. FIG. 32A shows the corrected pulse wave data MKD' in this example as data M1~M8 in each frequency region. FIG. 32B shows corrected body motion data TKD' as data M1~M8 in each of the frequency regions. It may be understood from FIG. 32B that the values of data M1 corresponding to 0 Hz~0.5 Hz and data M2 corresponding to 0.5 Hz~1.0 Hz are increasing in time period Ta~Tf. This is because time T1 at which body motion is generated and time T4 at which body motion ends correspond to period Ta and period Tf, respectively.

When corrected pulse wave data MKD' and corrected body motion data TKD' are generated at first and second frequency correctors 11A and 11B, respectively, and supplied to mask 18, mask 18 subtracts corrected body motion data TKD' from corrected pulse wave data MKD', to generate corrected pulse wave data MKD' from which the body motion component has been removed. This corrected pulse wave data MKD', is shown in FIG. 32C. As a result, even if body motion is present, its effect is canceled, making it possible to obtain corrected pulse wave data MKD" which is equivalent to corrected pulse wave data MKD' obtained from a pulse wave when the user is in a state of repose.

Decision element 12 determines whether arrhythmia has occurred based on the corrected pulse wave data MKD". In the processing for this determination, evaluation data QD is generated by referring to average value table (memory 123 in FIG. 26) which is obtained from a normal pulse wave. If average value data Ma1~Ma8 stored in the average value table are as shown in FIG. 32D, then evaluation data QDa~QDf generated in each period are as shown in FIG. 32E. Comparator 126 compares evaluation data QD with reference data RD. In this example, the value of reference table RD is fixed to be [1]. Note that the conditions for setting reference data RD to be variable are as disclosed in the third embodiment. In this example, the value of evaluation data QDe generated at time period Te is 2.5, exceeding the value of reference data RD. A determination is made that arrhythmia has occurred in time period Te, and the arrhythmia detection flag shown in FIG. 32F is generated as arrhythmia detection information FD.

When an arrhythmia flag is detected as arrhythmia detection information FD, then, as in the third embodiment, the fact that an arrhythmia event has occurred is displayed on display 13, and the clock time of the event is stored in RAM 14. The number of arrhythmia detection flags is added by summer 15. When this value exceeds a threshold, the user is notified of this fact by means of a buzzer. Moreover, when the frequency of occurrence per unit time exceeds a threshold, then in this case as well the buzzer is sounded.

The fourth embodiment is designed to carry out wavelet transformation on the body motion waveform TH, and then cancel the body motion component based on this. Thus, it is possible to accurately detect arrhythmia during daily activities or even if the user is exercising. As a result, it is possible to carry out the arrhythmia detection operation without hindering the subject, even in the case where measurements over an extended period of time, such as for arrhythmia sum information FSD over one day, are required. Accordingly, this is useful when diagnosing the subject's physiological state.

8. Fifth Embodiment

The arrhythmia detecting apparatus according to the fourth embodiment detected arrhythmia by detecting body motion using acceleration sensor 21, and canceling out the body motion component included in the corrected pulse wave data MDK' by subtracting corrected body motion data TKD' from corrected pulse wave data MKD'. However, because acceleration sensor 21, second wavelet transform element 10B, and second frequency corrector 11B are required, the structure of the fourth embodiment is complicated. The fifth embodiment of the present invention was conceived in consideration of this point, and intends to offer an arrhythmia detecting apparatus which can accurately detect arrhythmia even in the presence of body motion, despite its simple structure.

8-1. Structure of the Fifth Embodiment

Figure 33:
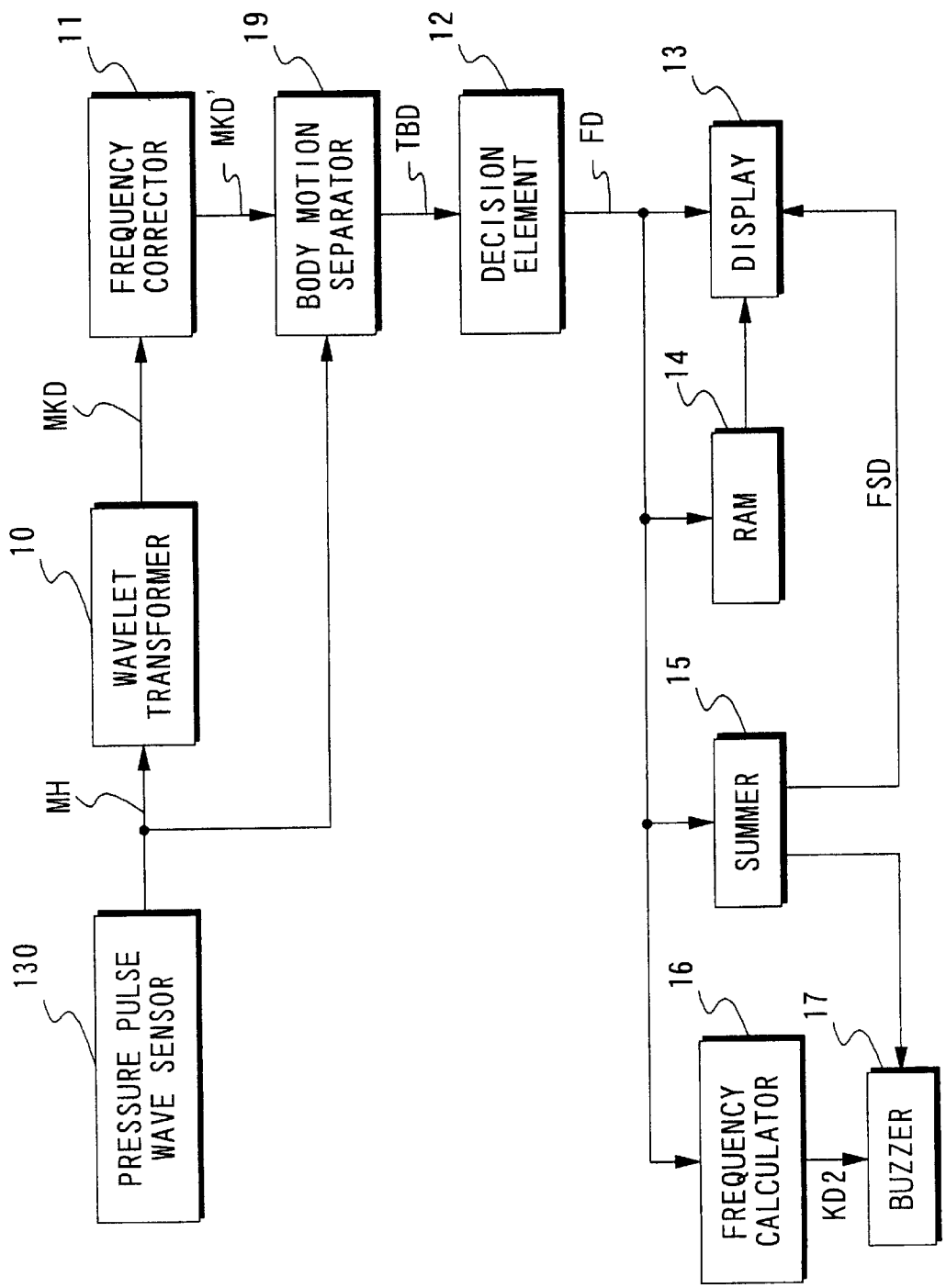
FIG. 33 is a block diagram showing the electrical structure of the arrhythmia detecting apparatus according to the fifth preferred embodiment of the present invention.

The outer appearance of the arrhythmia detecting apparatus according to the fifth embodiment is equivalent to the outer structure of the third embodiment shown in FIGS. 21 and 22, and therefore will not be explained here. The electrical structure of this embodiment will be explained, however. FIG. 33 is a block diagram of the arrhythmia detecting apparatus according to the fifth embodiment. FIG. 33 is equivalent to FIG. 23 explained in connection with the third embodiment, with the exception that a body motion separator 19 is newly disposed between frequency corrector 11 and decision element 12. This point of difference will be explained below.

Body motion separator 19 separates and removes the body motion component from corrected pulse wave data MKD', and generates corrected pulse wave data TBD from which body motion has been separated. Body motion separator 19 takes advantage of the following characteristics of body motion.

Namely, body motion is generated as a result of the vertical movement of the arms or the swinging motion of the arms during running. During the course of daily activities, there is almost no instantaneous movement of the body. For this reason, during daily activities, the frequency component of the body motion pulse wave TH does not become so high, but is typically in the range of 0 Hz~1 Hz. In this case, the frequency of the fundamental wave of the pulse waveform MH is frequently in the range of 1 Hz~2 Hz. Accordingly, during daily activities, the frequency component of the body motion waveform TH is in a frequency region which is lower than the frequency of the fundamental wave of the pulse waveform MH.

On the other hand, during sports such as jogging, the swinging motion of the arms and the like exerts an influence. For this reason, the frequency component of the body motion waveform TH becomes somewhat higher, while the pulse rate increases in response to the amount of exercise. For this reason, the frequency of the fundamental wave of the pulse waveform MH also becomes higher at the same time. Therefore, the frequency component of body motion waveform TH is typically in a frequency range which is lower than the frequency of the fundamental wave of the pulse waveform MH, even when the user is playing a sport.

Figure 34:
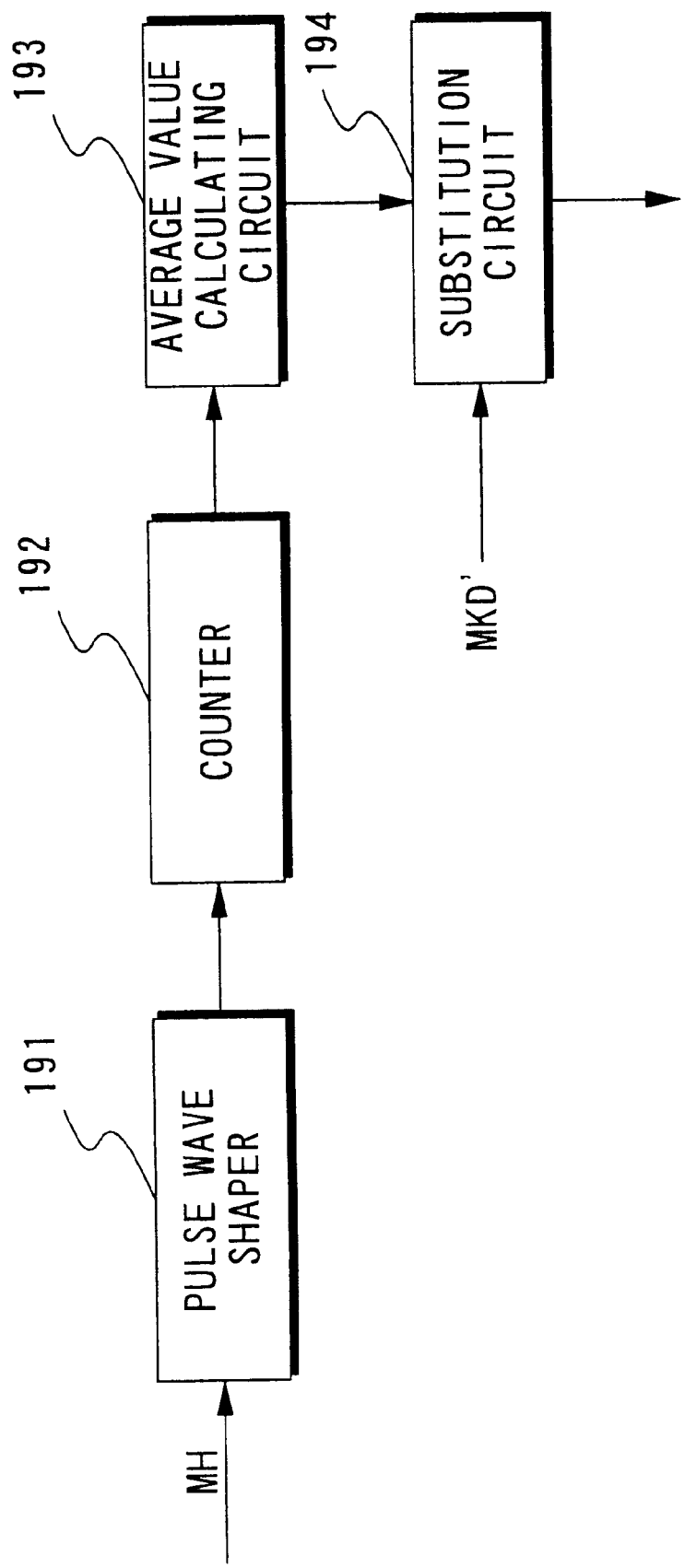
FIG. 34 is a circuit diagram showing the structure of body motion separator 19 according to this same embodiment.

Body motion separator 19 takes advantage of this point to separate the body motion component, and is designed to ignore frequency regions which are lower than the fundamental wave component of pulse waveform MH. In this case, if a body motion component is present in a frequency region which is higher than the fundamental wave component of the pulse waveform MH, then the accuracy of arrhythmia detection falls. However, since there is a higher probability that the body motion component will be in a frequency region which is lower than the fundamental wave component of the pulse waveform MH, it is possible to carry out highly accurate arrhythmia detection. FIG. 34 is a detailed block diagram of body motion separator 19. Waveform shaper 191 performs waveform shaping to pulse waveform MH, and generates a reset pulse synchronized with pulse waveform MH. More specifically, waveform shaper 191 is composed of ringing filter 101, zero cross detecting circuit 102, and the like. Counter 192 counts the clock pulses, which are not shown in the figures, and is designed so that the counter value is reset by means of the reset pulse. Average value calculating circuit 193 calculates the average of the counter value of counter 192, and may be composed of adder 121, coefficient circuits 122 and 123, and memory 123. In this case, the average value calculated by average value calculating circuit 193 corresponds to the average period of pulse waveform MH. Accordingly, if reference is made to the average value, then it is possible to detect the frequency of the fundamental wave of the pulse waveform MH.

Based on the aforementioned average value, substitution circuit 194 specifies the frequency region which includes the frequency of the fundamental wave of pulse waveform MH. For example, when the average value is 0.71 sec, then the frequency of the fundamental wave becomes 1.4 Hz. Thus, the frequency region specified is 1 Hz~1.5 Hz. Thereafter, for the frequency region which is less than the specified frequency region, substitution circuit 194 generates corrected pulse wave data TBD from which the body motion component has been separated, by substituting the corrected pulse wave data MKD' with [0]. As a result, components of frequency regions lower than the frequency of the fundamental wave of pulse waveform MH are ignored in the arrhythmia determination. In this case, the pulse wave component is substituted by [0], along with the body motion component. However, since the characteristic portion of pulse waveform MH is present in a frequency region which is higher than the frequency of the fundamental wave, this substitution to [0] has almost no impact on the determination of arrhythmia.

Based on the thus-generated corrected data TBD from which the body motion component has been separated, decision element 12 generates arrhythmia detection information FD after carrying out the determination of arrhythmia. Display 13 and other parts subsequent to decision element 12 are composed in the same manner as in the third embodiment, and are therefore not explained again here.

8-2. Operation of the Fifth Embodiment

The operation of the fifth embodiment will now be explained with reference to the figures.

Figure 35:
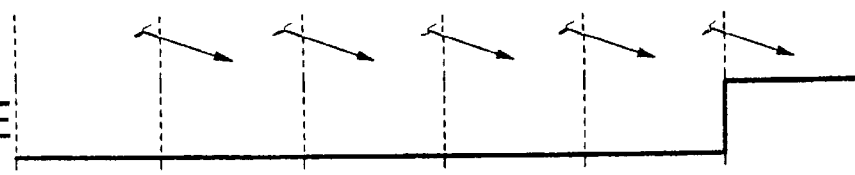
FIGS. 35A, 35B, 35C, 35D and 35E are timing charts for explaining the operation of this same embodiment.

Pulse waveform MH shown in FIG. 31A was detected by a pressure pulse wave sensor 130 in this example. FIG. 35 is a timing chart showing the operation of an arrhythmia detecting apparatus according to the fifth embodiment. The time periods Ta~Tf shown in FIG. 35 correspond to those shown in FIG. 31.

FIG. 35A shows the corrected pulse wave data MKD' in this example as data M1~M8 in each frequency region, and is equivalent to FIG. 32A. The frequency of the fundamental wave of the pulse waveform MH is set to be 1.3 Hz. The frequency region specified by substitution circuit 194 becomes 1.0 Hz~1.5 Hz. Thus, the frequency region for substitution becomes 0.5 Hz~1.0 Hz corresponding to data M2 and 0 Hz~0.5 Hz corresponding to M1. Accordingly, data M1,M2 of corrected pulse wave data MKD' is substituted by [0], generating corrected pulse wave data TBD, shown in FIG. 35B, from which the body motion component has been separated.

Decision element 12 decides arrhythmia based on this corrected pulse wave data TBD from which the body motion component has been removed. Average value table (memory 123 of FIG. 26) obtained from normal pulse waves is referenced during the decision process, generating evaluation data QD. If average value data Ma1~Ma8 stored in the average value table is as shown in FIG. 35C, then evaluation data QDa~QDf generated in each time period becomes as shown in FIG. 35D.

It may be understood from a comparison between FIG. 35D and FIG. 32E that there is a slight difference between evaluation data QDb and QDe. This is due to the presence of a slight 1.0 Hz~1.5 Hz component in body motion. In other words, referring to the corrected body motion data TKD' shown in FIG. 32B, the value of data M3 in time period Tb,Td becomes [1], with the 1.0 Hz~1.5 Hz component being present here. This component is ignored when substitution is carried out by substitution circuit 194, so that a slight deviation is generated. However, the difference between evaluation data QDb,QDe is 0.1, so that even if this difference is ignored, there is very little deterioration in the accuracy of the arrhythmia determination.

Comparator 126 compares evaluation data QD and reference data RD. In this example, the value of reference data RD is fixed at [1]. Note that the reason why the value of reference data RD may be variable is as set forth in the third embodiment.

The value of evaluation data QDe generated in time period Te in this example is 2.5, exceeding the value of reference data RD. Accordingly, a determination is made that arrhythmia has occurred in time period Te, generating the arrhythmia flag shown in FIG. 35E. This arrhythmia flag is equivalent to that shown in FIG. 32F.

When this arrhythmia detection flag is detected as arrhythmia detection information FD, the fact that arrhythmia has occurred is displayed on display 13, in the same manner as in the third embodiment. In addition, the clock time at which the arrhythmia occurred is recorded RAM 14. The number of arrhythmia detection flags is added by summer 15. If this value exceeds the threshold value, then the user is notified by means of a buzzer. Further, if the frequency of occurrence per unit time exceeds a threshold value, then a buzzer is used to notify the user of this fact.

In the fifth embodiment of the present invention, the body motion component is separated by skillfully taking advantage of the characteristic of body motion wherein there is a high probability that the body motion component is present in a frequency region which is lower than the frequency component of the fundamental wave of the pulse waveform MH. For this reason, it is possible to omit the acceleration sensor 21, second wavelet transform element 10B, and second frequency corrector 11B, which are required in the fourth embodiment. Moreover, it is possible to detect arrhythmia accurately even when body motion is present.

9. Modifications

The present invention is not limited to the preceding embodiments, but may, for example, be modified in the following ways.

(1) The third through fifth embodiments employed frequency correctors for comparing the energy in different frequency regions. However, it is also acceptable to detect arrhythmia by focusing on a given frequency region, and comparing the energy levels thereof. In this case, it is not necessary to employ a frequency correction means. For example, when selecting the frequency regions 0~0.4 Hz, 0.4~0.8 Hz, 0.8~1.6 Hz, 1.6~3.2 Hz, and 3.2~6.4 Hz, the fundamental wave component is viewed to be present in the 0.8 Hz~1.6 Hz and 1.6 Hz~3.2 Hz regions. Thus, arrhythmia may be detected by obtaining the sum of these two regions and comparing this to a given reference value.

Figure 36:
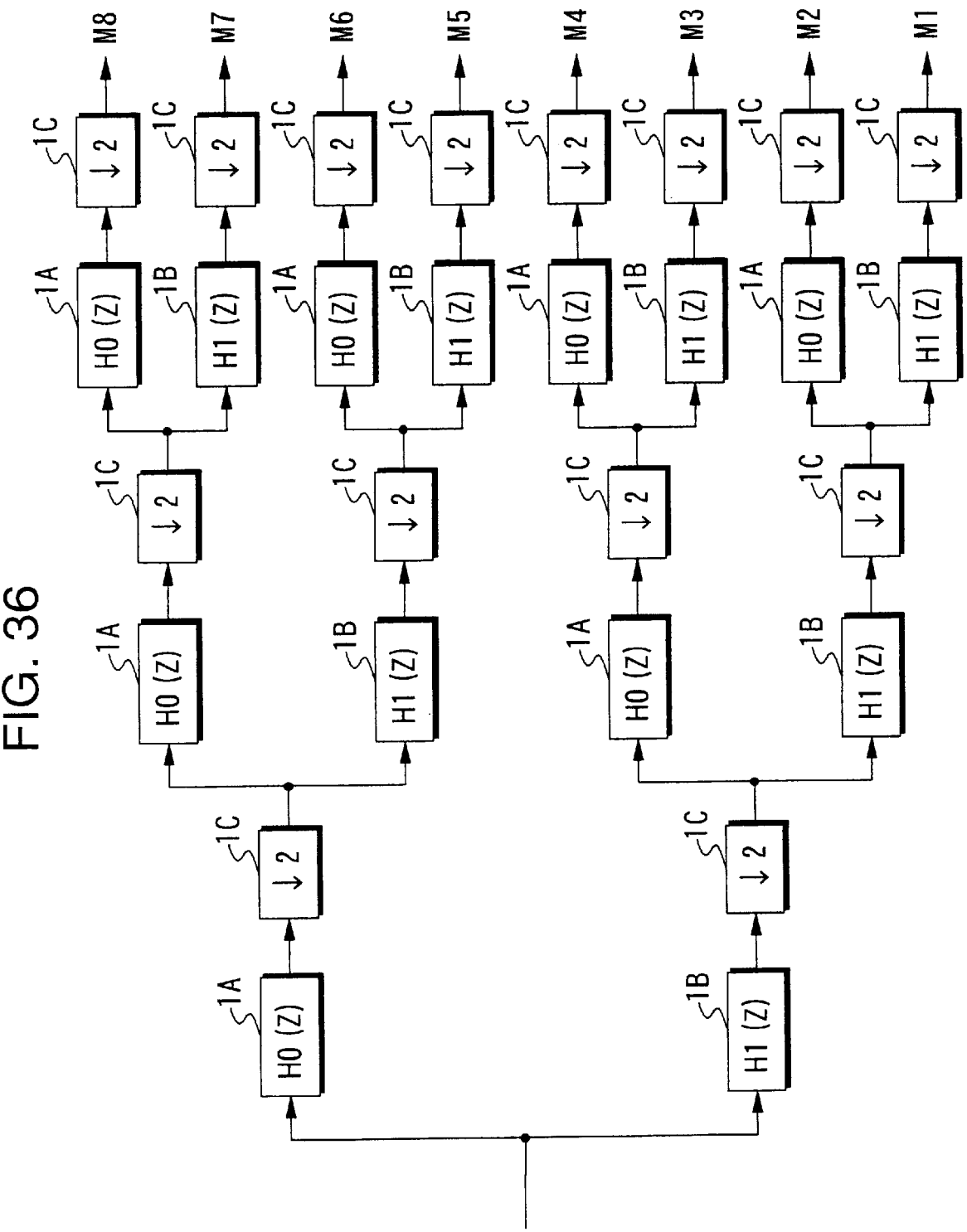
FIG. 36 is a block diagram showing the structure of the filter bank in a modification.

(2) In the third through fifth embodiments, each of wavelet transform elements 10,10A,10B were provided with a normal function developer W which carried out wavelet transformation. However, the present invention is not limited thereto. Rather, wavelet transformation may also be realized by means of a filter bank. An example of the structure of a filter bank is shown in FIG. 36. In this figure, the filter bank is composed of three stages, with the fundamental unit being high-pass filter 1A and decimation filter 1C, and low region filter 1B and decimation filter 1C. High-pass filter 1A and low region filter 1B are designed to separate a given frequency region, and output a high region frequency component and a low region frequency component, respectively. This example preconceives 0 Hz~4 Hz as the frequency range of pulse wave data MD, so that the transmission region of the first high-pass filter 1A is set to 2 Hz~4 Hz, while the transmission region of the first low region filter 1B is set to 0 Hz~2 Hz. Decimation filter 1C weeds out data in each sample.

The thus generated data is supplied to the next stage, and frequency region separation and data weed out is repeated, with data M1~M8 obtained finally with the separation of the 0 Hz~4 Hz frequency region into 8 portions.

The high-pass filter 1A and low region filter 1B may be composed of a transversal filter which includes a delay element (D flip-flop) inside. The human pulse rate is in the range of 40~200 beats. The frequency of the fundamental wave of the pulse waveform MH fluctuates moment by moment in response to physiological state. If it is possible to vary the region to be separated in synchronization with the frequency of the fundamental wave, then it is possible to obtain dynamic information in line with the physiological state. Therefore, a clock supplied to the transversal filter may be timed to the pulse waveform MH, with the region to be separated varied appropriately.

From among the pulse wave analysis data MKD, the representative frequency components which express the characteristics of the pulse waveform MH are the frequency components of the fundamental wave, second higher harmonic wave and third higher harmonic wave. Accordingly, a portion of the output data M1~M8 of the filter bank may be used to carry out arrhythmia determination. In this case, if the filter bank is designed so as to be synchronous with the pulse waveform MH, then it is possible to omit one of the high-pass filter 1A, low region filter 1B and decimation filter 1C, thereby simplifying the structure.

(3) The body motion waveform TH was detected using an acceleration sensor 21 in the fourth embodiment. When body motion is detected, the frequency of the fundamental wave of the pulse waveform MH becomes high because the user is in a state of exercise. This pulse waveform MH undergoes frequency analysis at first wavelet transform element 10A. However, if the frequency region which is the target of frequency analysis is fixed, then it may be difficult to fully analyze the characteristic portions of the pulse waveform MH. For example, when an individual in which the frequency of the fundamental wave of pulse waveform MH at rest is 1 Hz goes running, the frequency of the fundamental wave of pulse waveform MH changes to 2 Hz (corresponding to a pulse rate of 120). By carrying out wavelet transformation within the region 0~4 Hz explained above in the fourth embodiment, it is possible to carry out frequency analysis through the third higher harmonic wave of the pulse waveform MH. However, since the third higher harmonic wave reaches 6 Hz during running, it becomes impossible to carry out frequency analysis.

Therefore, the quantity of exercise may be obtained based on the body motion waveform TH, with the first and second wavelet transform elements 10A,10B being controlled so that the frequency region in which wavelet transformation is carried out shifts to a higher region as the amount of exercise increases.

When forming the first and second wavelet transform elements 10A,10B from filter banks as described above, control of the clock frequency may be carried out in response to the amount of exercise. In other words, it is acceptable to carry out conventional feed back control so that the clock frequency becomes higher as the amount of exercise increases.

During running, the pitch of body motion waveform TH shows the pitch of the return cycle of the runner's arms, and has a constant relationship with the pitch of stride of the feet. Typically, two steps are taken with each swing of the arms. Further, the exercise quantity can be shown as the product of running speed and length of step. In general, as running speed is increased, the pitch tends to increase while length of step tends to decrease. Accordingly, there is a constant relationship between the body motion waveform TH and exercise quantity.

Figure 41:
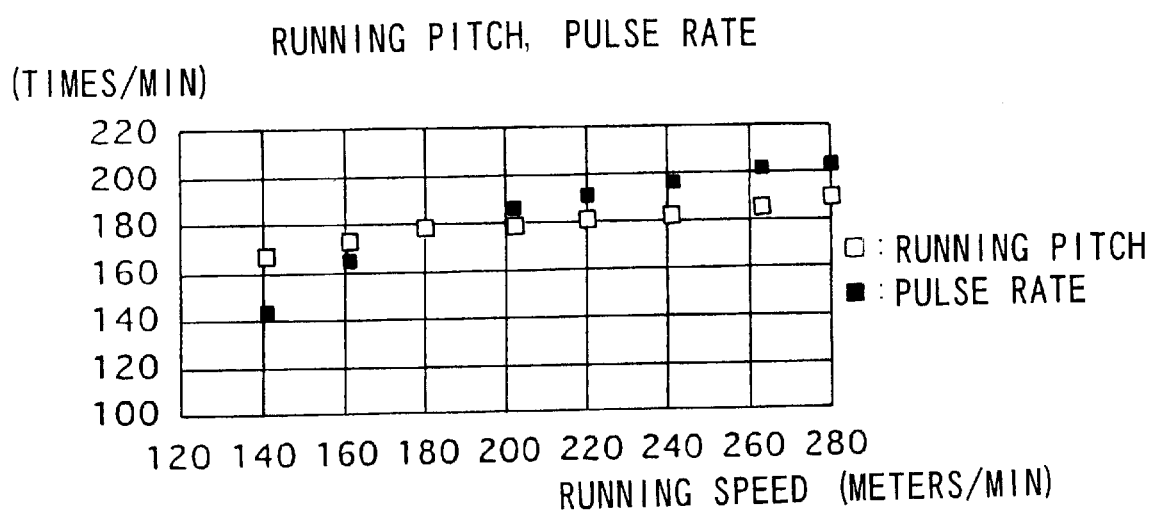
FIG. 41 is a figure for explaining the relationship between beat number and pitch in the modification.

For example, FIG. 41 shows both the relationship between pulse and running speed when running on the ground, and the relationship between running pitch and running speed. As shown in this figure, it is clear that the pulse and running pitch of the test subject increase as the running speed increases. Namely, when the running pitch increases, the exercise quantity and the pulse rate increase accompanying this. Accordingly, the relationship between exercise quantity and the pitch of the body motion waveform TH may be measured in advance, and stored in a table, with the exercise quantity calculated by referring to this table.

From FIG. 41, it may be considered that there is a constant relationship between the pitch of body motion waveform TH and heartbeat. Accordingly, the relationship between the pitch of body motion waveform TH and the frequency region which is the target of frequency analysis may be stored in a table, with the frequency region which is the target of frequency analysis then read out by referring to the table, based on the pitch of the measured body motion waveform TH. More concretely, the relationship between the pitch of the body motion waveform TH and the optimal clock frequency may be measured in advance, and stored in a table, with this table referred to when determining the clock frequency.

In these cases, it is acceptable to store data from only a few sites, rather than determining the relationship with the pitch of body motion waveform TH in detail. The remaining data may then be interpolated.

The modification described above may be employed in an arrhythmia detecting apparatus in which a body motion detecting means such as acceleration sensor 21 and so on has been added to the structure of the fifth embodiment. In this case, the frequency region which is the target of wavelet transformation may be varied in response to the body motion pitch, by detecting the body's exercise state based on the body motion waveform TH detected by the body motion detecting means, and providing a control means which varies the frequency region of the frequency analysis carried out by the wavelet transform element based on the result of the detection.

(4) In the fourth embodiment, a first frequency corrector 11A and a second frequency corrector 11B were provided prior to mask 18, and frequency correction was carried out separately for pulse wave analysis data MDK and body motion analysis data TKD. However, it is also acceptable to provide a frequency corrector after mask 18, in place of first and second frequency correctors 11A,11B. Since frequency correction is carried out in common in this case, it is possible to carry out arrhythmia detection easily with this design.

In the fifth embodiment, a frequency corrector 11 was provided prior to body motion separator 19, however, the present invention is not limited thereto. Rather, frequency corrector 11 may be provided after body motion separator 19, and its output supplied to decision element 12. Namely, frequency correction may be carried out between wavelet transformation and the processing for arrhythmia determination. In addition, it is also acceptable to omit frequency corrector 11.

(5) In the third through fifth embodiments, a controller which generates third warning information KD3 based on arrhythmia frequency information FHD and arrhythmia sum information FSD may be newly provided, with notice provided by supplying third warning information KD3 to buzzer 17. In this case, the controller generates third warning information KD3 when arrhythmia frequency information FHD and arrhythmia sum information FSD both exceed respective predetermined values. The conditions for generating the third warning information may be stored in a table after being related to arrhythmia frequency information FHD and arrhythmia sum information FSD, with third warning information then generated after referring to this table.

(6) Arrhythmia sum information FSD may be displayed in the third through fifth embodiments after carrying out grading of this information. More specifically, when displaying arrhythmia sum information FSD, it is acceptable to display a phrase such as "illness very likely", "caution", "health state average", "health state moderate", or "health state good" on an LCD and so on. In this case, the letters A, B, C, D, and E may be applied as grades to each of these displays, respectively, with these symbols then displayed on an LCD and so on.

(7) The preceding first through fifth embodiments were explained using pressure pulse wave sensor 130 as an example of the pulse wave detection means. However, the present invention is not limited thereto. Rather, any means is acceptable, provided that it is one which is capable of detecting the pulse. Moreover, this applies in either the case where pulse detection is carried out at the radius artery or where it is carried out at the fingertip.

Figure 37:
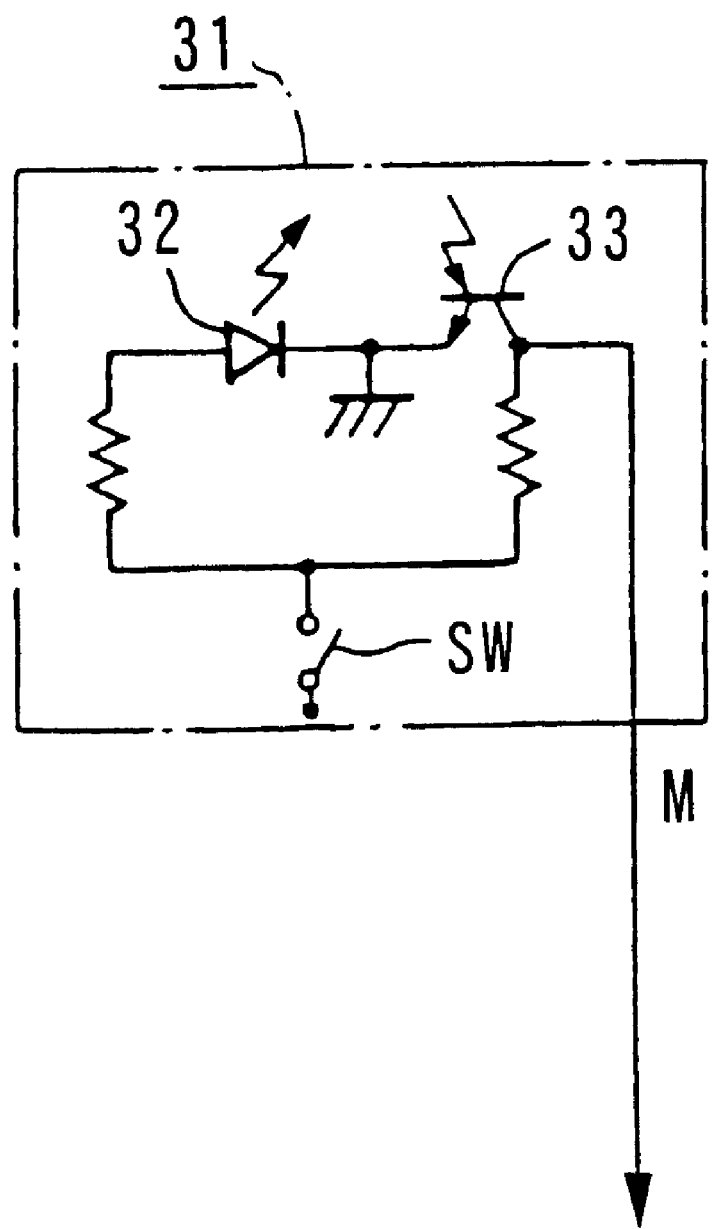
FIG. 37 is a circuit diagram of the photoelectric pulse wave sensor according to a modification.

For example, a photoelectric pulse wave sensor may be used. Photoelectric pulse wave sensors have a design such as shown in FIG. 37, with some sensors of this type employing reflected light and some employing transmitted light.

Photoelectric pulse wave sensors employing reflected light will first be explained. When the switch SW in FIG. 37 is placed in the ON state, causing voltage from the electric to be impressed, light is irradiated from LED 32. This light is received at photo transistor 33 after being reflected by the blood vessels and tissue, with a pulse wave signal M thereby being detected. The wavelength of the light generated by the LED is selected to be in the vicinity of the absorption wavelength peaks of the hemoglobin in the blood. Thus, the level of received light will change in response to the blood flow quantity. Accordingly, by detecting the level of the received light, pulse detection can be accomplished.

When employing reflected light, a InGaN-type (indium-gallium-nitrogen) blue LED is suitably employed for the LED. The generated light spectrum of a blue LED has a peak at 450 nm, for example, with the generated light wavelength region being in the range of 350 to 600 nm. In this case, a GaAsP-type (gallium-arsenic-phosphorous) photo transistor PT may be used for the photo transistor PT corresponding to the LED having the light emitting characteristics described above. The wavelength region of the received light of the photo transistor PT has, for example, a main sensitive region in the range of 300 to 600 nm, with a sensitive region also present below 300 nm. When a blue LED and photo transistor PT such as described above are combined, the pulse wave is detected in the overlapping wavelength region of 300 to 600 nm. This offers the following advantages.

In the case of outside light, it tends to be difficult for light having a wavelength region of 700 nm or less to pass through the tissues of the finger. For this reason, even if the portion of the finger not covered by the sensor-fixing band is irradiated with outside light, the light does not reach photo transistor 33 through the finger tissue. Rather, only light in the wavelength region which does not influence the detection reaches photo transistor 33. On the other hand, light in the low wavelength region of 300 nm or less is almost entirely absorbed by the skin surface. Thus, even if the wavelength region of the received light is set to 700 nm or less, the actual wavelength region of the received light is 300 to 700 nm. Accordingly, it is possible to restrain the impact of outside light, without having to significantly cover the finger. Moreover, the absorption coefficient of blood hemoglobin with respect to light having a wavelength of 300 to 700 nm is large, and is several to 100-fold greater than the absorption coefficient with respect to light having a wavelength of 880 nm. Accordingly, as in this example, when light in the wavelength region (300 to 700 nm) in which the absorption characteristics are large is employed as the detection light, in response to the absorption characteristics of hemoglobin, then the detected value varies with good sensitivity in response to changes in the blood volume. Accordingly, it is possible to increase the S/N ratio of the pulse wave signal which is based on the change in blood volume.

An explanation will now be made of the case where transmitted light is employed. As mentioned above, it tends to be difficult for light in the 700 nm wavelength region or lower to pass through the finger tissue. For this reason, when transmitted light is employed, light having a wavelength of 600 to 1000 nm is irradiated from the light emitting element, with the irradiated light being transmitted in the order of tissue→blood vessels→tissue. The change in the amount of light in the transmitted light is then detected. Since the transmission light is subject to absorption by the hemoglobin in the blood, it is possible to detect the pulse waveform by detecting the change in the light quantity of the transmitted light.

A InGaAs-type (iridium-gallium-arsenic) or GaAs-type (gallium-arsenic) laser emitting diode may be suitably employed for the light emitting element. Since outside light of wavelength 600 to 1000 nm passes readily through the tissues, the S/N of the pulse wave signal will deteriorate if outside light incidences on the light receiving element. Therefore, laser light which has been polarized from the light emitting element may be irradiated, with the transmitted light received at the light receiving element via a polar light filter. As a result, there is no impact from outside light, so that the pulse wave signal can be detected at a good S/N ratio.

Figure 38A:
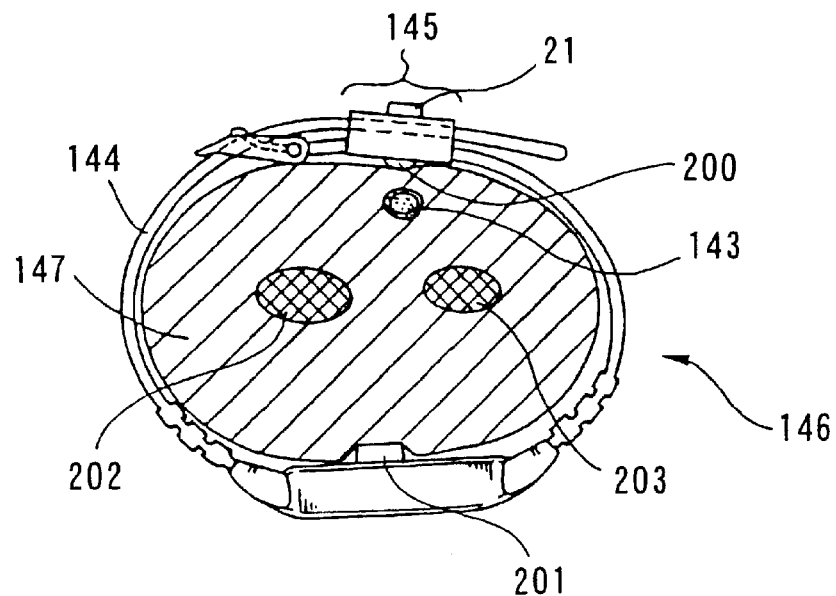
FIGS. 38A and 38B are figures for explaining the state of the photoelectric pulse wave sensor when in use, according to a modification.

A photoelectric pulse wave sensor may be employed in the wrist watch described above. When employing reflected light, a sensor unit which is formed in a unitary manner with the light emitting and light receiving elements may be used in place of elastic rubber 131 and the pressure pulse wave sensor 130 which is provided to the rear thereof. In contrast, when transmitted light is employed, then a light emitting element 200 is provided to the fastener side, and a light receiving element 201 is provided to the wrist watch side, of belt-shaped fastener 145 as shown in FIG. 38A. In this case, light irradiated from light emitting element 200 passes through blood vessel 143, and then travels between the radius 202 and the ulna 203 to reach the light receiving element 201. Since it is necessary that the irradiated light pass through the tissue in the case where employing transmitted light, a wavelength of 600 to 1000 nm is desirable in view of absorption by the tissues.

Figure 38B:
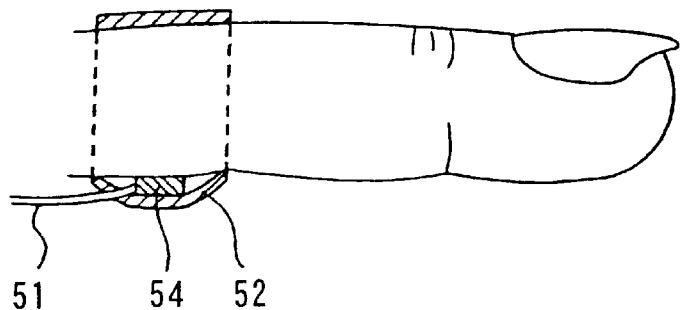
Figure 38C:
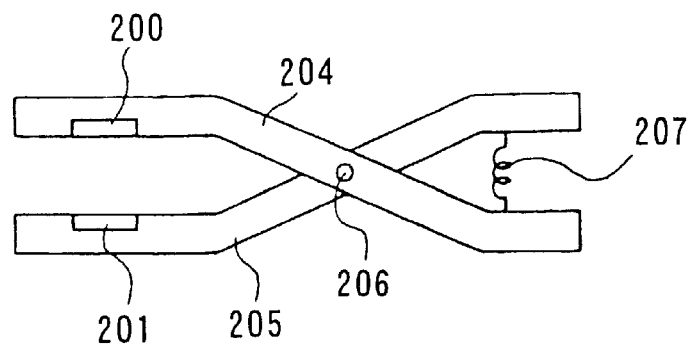

An explanation will now be made of the state of use when the detection position is on the finger. FIG. 38B is an example in which reflected light is used to detect the pulse wave at the fingertip. Light emitting and light receiving elements are incorporated into sensor unit 54. A ring-shaped sensor fixing band 52 is used to fix the apparatus to the finger. In this case, sensor unit 54 and apparatus main body 1 are connected as shown in FIG. 3. Pulse wave signal MS is supplied to apparatus main body 1 via connection cable 51. FIG. 38C is an example in which transmitted light is used to detect the pulse wave. Gripping member 204 and gripping member 205 are biased by means of a spring 207, and are designed to rotate around axis 206. Light emitting element 200 and light receiving element 201 are provided to gripping member 204 and gripping member 205. When employing this pulse wave detecting apparatus, the pulse is detected by gripping the web between the thumb and the index finger with gripping members 204 and 205.

The state of use when the photoelectric pulse wave sensor is combined with a pair of eyeglasses will now be explained. Note that in the arrangement of these eyeglasses, a display device is also incorporated as a means for providing notice to the user. Accordingly, in addition to the function as a pulse wave detector, an explanation will also be made of the functions as a display apparatus.

Figure 39:
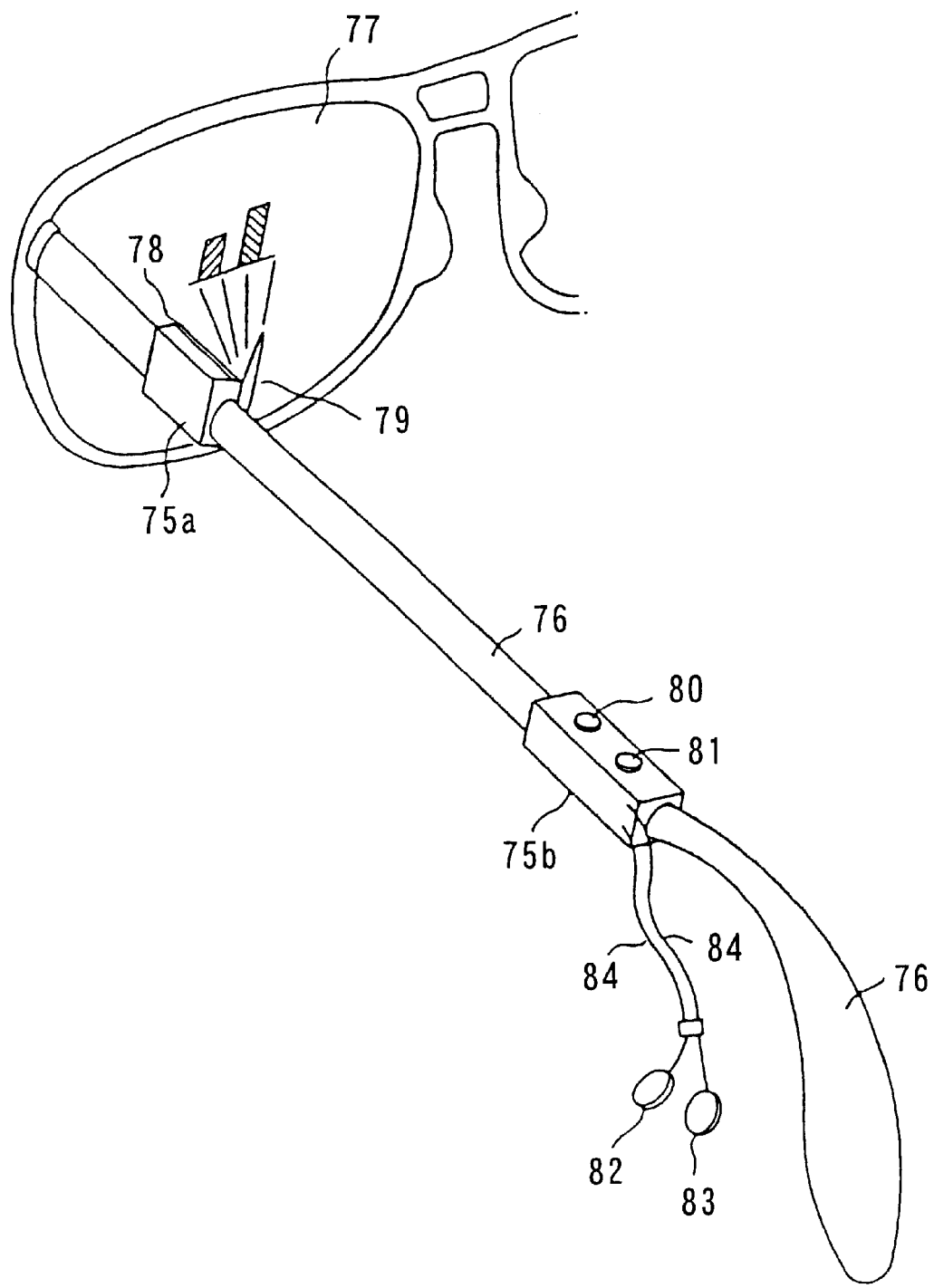
FIG. 39 is a slant view showing a modification in which an apparatus connected to a photoelectric pulse wave sensor is attached to a pair of eyeglasses.

FIG. 39 is a slant view showing an arrangement in which an apparatus to which a pulse wave detector is connected is attached to a pair of eyeglasses. As shown in the figure, the apparatus main body is divided into a main body 75a and a main body 75b, which are attached to the stems 76 of the eyeglasses, respectively. These main bodies are connected electrically via a lead wire embedded in stems 76.

Main body 75a houses a display control circuit. A liquid crystal panel 78 is attached over the entire surface of the lens 77 side of main body 75a. A lens 79 is fixed to the edge of this lateral surface at a specific angle. A drive circuit for liquid crystal panel 78 which includes a light source (not shown) and a circuit for forming display data are incorporated in main body 75a. The light emitted from this light source passes via liquid crystal panel 78, and is reflected at mirror 79 to incident on lens 77 of the eyeglasses. The principle components of the apparatus are incorporated in main body 75b, with various types of buttons provided to the top surface thereof. Note that the functions of these buttons 80,81 will differ for each apparatus.

Photo transistor 33 and LED 32 (see FIG. 37) which form the photoelectric pulse wave sensor are housed in pads 82,83, with pads 82,83 designed to fix in place to the earlobe. These pads 82,83 are electrically connected by lead wires 84,84 which are pulled out from main body 75b.

It is acceptable, for example, for the device to be a photoelectric pulse wave sensor having a design such as shown in FIG. 37. When switch SW is turned ON, causing voltage from the electric source to be impressed, light is irradiated from LED 32, reflected by the blood vessels and tissues, and then received at photo transistor 33, where the pulse wave signal M is detected. The wavelength of the light emitted by the LED in this case is selected so as to be near the absorption wavelength peak of hemoglobin in the blood. For this reason, the level of the received light varies in response to the blood flow volume. Thus, the pulse can be detected by detecting the level of the received light.

Figure 40:
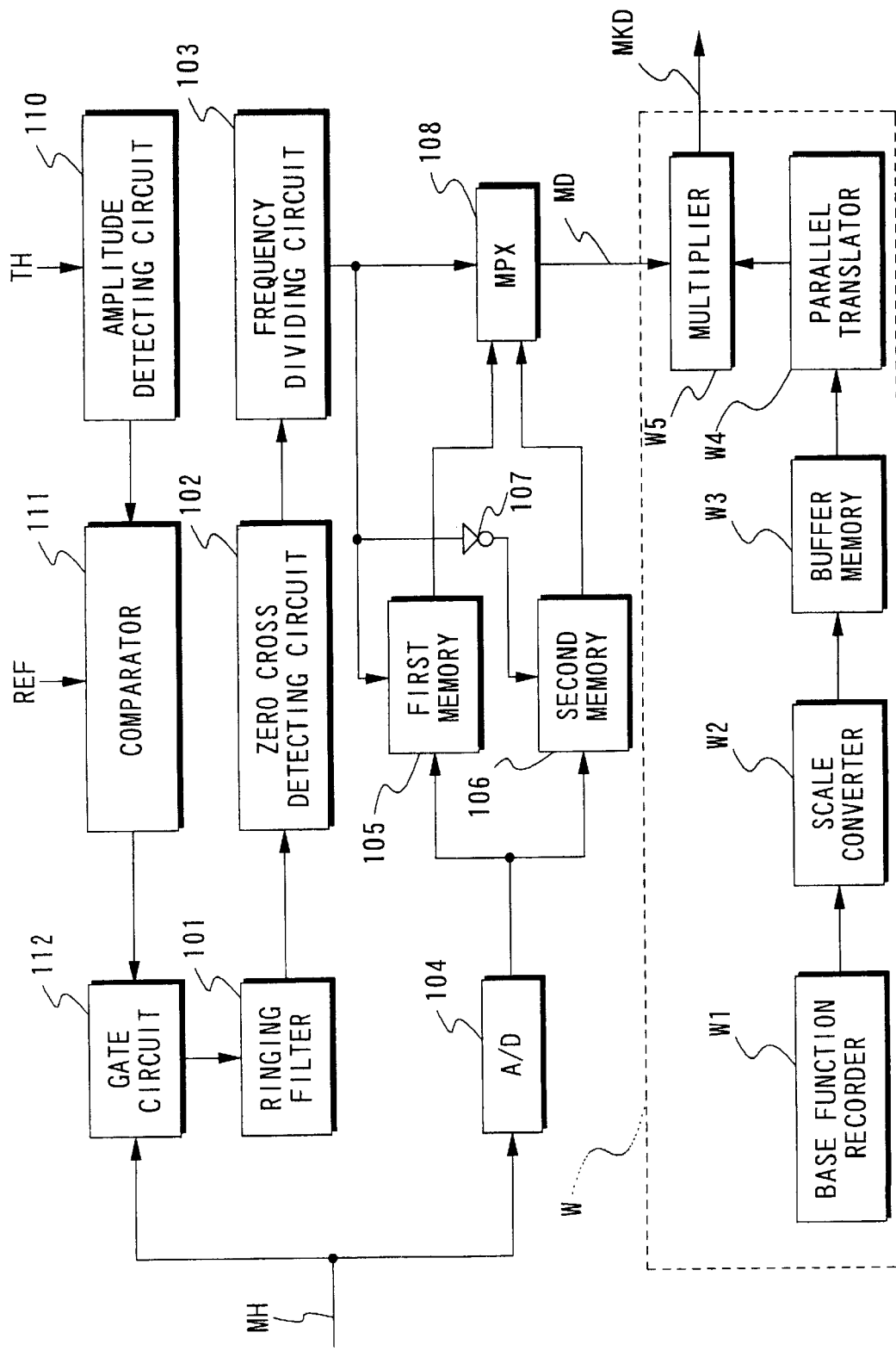
FIG. 40 is a circuit diagram for the first wavelet transforming means according to a modification.

(8) First wavelet transformer 10A in the fourth embodiment may be designed such as shown in FIG. 40.

In FIG. 40, body motion waveform TH is supplied to amplitude detection circuit 110, and the amplitude value PP thereof is detected. This amplitude value PP is compared to a reference value REF by comparator 111. A control signal is then generated at comparator 111 which is at a low level during the interval in which amplitude value PP exceeds reference value REF, and is at a high level during the interval in which amplitude value PP is below reference value REF. This control signal indicates the presence or absence of body motion. Namely, body motion is present during the low level interval, but is absent during the high level interval. Here, reference value REF is determined in advance by experiments to enable discrimination between the presence and absence of body motion. Gate circuit 112 applies a gate to pulse waveform MH based on the control signal. Specifically, the pulse waveform MH may be supplied to the ringing filter when the control signal is at a high level, but not supplied to the ringing filter when the control signal is at a low level. As a result, it is possible to mask pulse waveform MH during the time period in which body motion is present.

The Q value of the ringing filter in this case is set to be high, so that even if the supply of pulse waveform MH is stopped for a fixed period of time, it is possible to continue outputting a sinusoidal wave which is continuous with the waveform output prior to the cessation of supply of pulse waveform MH. Accordingly, even if body motion is present, it is possible to calculate the period of the pulse waveform MH, and carry out wavelet transformation based on the result of this calculation.

(9) It is acceptable to carry out arrhythmia detection as described below in each of the third through fifth embodiments. First, the continuity of the pulse waveform MH is determined from the pulse wave analysis data MKD resulting from wavelet transformation (step S1). Next, when discontinuity is detected, a determination of the presence or absence of body motion is made based on the body motion waveform TH (step S2). When a determination is made that body motion is present, then the body motion component is removed from the pulse wave component by means of the method described in the fourth and fifth embodiments, with the arrhythmia determination them made based on this result (step S3). Conversely, when a determination is made in step S1 that the pulse waveform is continuous, then a determination is made that arrhythmia was not present (step S4).

(10) When body motion is absent in the first through fifth embodiments, then it is not necessary to carry out FFT transformation or wavelet transformation processing. Rather, an irregular pulse may be detected based on the number which is calculated for each portion in which the pulse waveform exceeds the threshold value. It frequently occurs during daily activities that there is a continuous period during which there is no body motion. Thus, by switching the processing in response to the presence or absence of body motion, it is possible to reduce the processing time, as well as cut down on power consumption.

What is claimed:

1. An arrhythmia detecting apparatus comprising:
   a pulse wave detecting means which non-invasively detects the pulse waveform in the body;
   a body motion component excluding means which excludes the only influence of the body motion from the pulse waveform detected by said pulse wave detecting means; and
   a notifying means which provides notice of information showing the pure pulse waveform obtained after the only influence of the body motion has been excluded by said body motion component excluding means.

2. An arrhythmia detecting apparatus according to claim 1, further comprising:
   body motion detecting means which detects motion of the body and outputs a body motion waveform; and
   wherein said body motion component excluding means excludes the only influence of the body motion specified by said body motion waveform from the pulse waveform detected by said pulse wave detecting means.

3. An arrhythmia detecting apparatus comprising:
   a pulse wave detecting means which non-invasively detects the pulse waveform in the body;
   a body motion component excluding means which excludes the body motion component from the pulse waveform detected by said pulse wave detecting means;
   an arrhythmia detecting means which detects arrhythmia by monitoring changes in the pure pulse waveform obtained after the body motion component has been excluded by said body motion component excluding means; and
   a notifying means which provides notice of the results of detection by said arrhythmia detecting means.

4. An arrhythmia detecting apparatus according to claim 3, further comprising:
   body motion detecting means which detects body motion and outputs a body motion waveform;
   a reference value deciding means which obtains a representative value for the interval between pulse waves which compose said pulse waveform during the interval for determining a reference value, and sets said representative value as the reference value for the pulse wave interval; and
   a comparing means which obtains an interval value with respect to the pulse waveform detected by said pulse wave detecting means, and determines the difference between said interval value and said reference value; wherein,
   said body motion component excluding means supplies the pulse waveform detected by said pulse wave detecting means to said comparing means only in the case where a body motion waveform is not output from said body motion detecting means; and
   said notifying means provides notice of the difference obtained by said comparing means.

5. An arrhythmia detecting apparatus according to claim 3, further comprising:
   body motion detecting means which detects body motion and outputs a body motion waveform;
   a reference value deciding means which obtains a representative value for the interval between pulse waves which compose said pulse waveform during the interval for determining the reference value, and sets said representative value as the reference value for the pulse wave interval;
   a comparing means which obtains the interval with respect to the pulse waveform detected by said pulse wave detecting means, and obtains the difference between said interval value and said reference value; and
   a deciding means which determines that arrhythmia has occurred when said difference obtained by said comparing means is outside a prespecified range; wherein,
   said body motion component excluding means supplies the pulse waveform detected by said pulse wave detecting means to said comparing means only in the case where a body motion waveform is not output from said body motion detecting means; and
   said notifying means provides notice of the result of determination by said deciding means.

6. An arrhythmia detecting apparatus according to claim 4, wherein said arrhythmia detecting means has a reference value updating means which updates said reference value using said intervals, in the case where the difference obtained by said comparing means for two continuous pulse wave intervals is within a prespecified range.

7. An arrhythmia detecting apparatus according to claim 3, wherein:
said arrhythmia detecting means has a frequency analysis means which carries out frequency analysis on the pulse waveform detected by said pulse wave detecting means;
said body motion component excluding means excludes the body motion component from the frequency analysis results obtained from said frequency analysis means; and
said arrhythmia detecting means detects arrhythmia using said frequency analysis results from which the body motion component has been excluded by said body motion component excluding means.

8. An arrhythmia detecting apparatus according to claim 7, wherein:
said arrhythmia detecting means has a body motion constancy deciding means which determines the presence or absence of constancy in body motion based on the body motion waveform output from said body motion detecting means; and
said arrhythmia detecting means detects arrhythmia based on the results of frequency analysis by said frequency analysis means, only in the case where said body motion constancy deciding means has determined that constancy is present in body motion.

9. An arrhythmia detecting apparatus according to claim 7, wherein:
said arrhythmia detecting means employs a Fourier transform means as said frequency analysis means, said Fourier transform means carrying out Fast Fourier transform to the pulse waveform detected by said pulse wave detecting means.

10. An arrhythmia detecting apparatus according to claim 9, wherein:
said arrhythmia detecting means has a range estimating means which estimates the appropriate range of variation in the beat frequency; and
a determination is made that arrhythmia has occurred in the case where a frequency spectral line projecting into the range of variation estimated by said range estimating means is not present in the frequency analysis results of said Fourier transform means.

11. An arrhythmia detecting apparatus according to claim 9, further comprising:
body motion detecting means which detects the motion of the body and outputs a body motion waveform; wherein,
said arrhythmia detecting means has said Fourier transform means as a first Fourier transform means, and a second Fourier transform means which carries out Fast Fourier transform to the body motion waveform detected by said body motion detecting means;
said body motion component excluding means subtracts the results of said second Fourier transform from the results of analysis by said first Fourier transform means; and said arrhythmia detecting means detects arrhythmia using the results of the subtraction operation by said body motion component excluding means.

12. An arrhythmia detecting apparatus according to claim 9, further comprising:
body motion detecting means which detects the motion of the body and outputs a body motion waveform; wherein,
said arrhythmia detecting means includes said Fourier transform means as a first Fourier transform means, and a second Fourier transform means which carries out Fast Fourier transform to said body motion waveform detected by said body motion detecting means;
said body motion component excluding means obtains the frequency component corresponding to body motion from the results of frequency analysis by said second Fourier transform means, and excludes said frequency component from the frequency analysis results of said first Fourier transform; and
said arrhythmia detecting means detects arrhythmia using the frequency analysis results from which the frequency component corresponding to body motion has been excluded by said body motion component excluding means.

13. An arrhythmia detecting apparatus according to claim 7, wherein:
said arrhythmia detecting means employs a wavelet transforming means for said frequency analysis means, the wavelet transforming means carrying out wavelet transformation to the pulse waveform detected by said pulse wave detecting means, and generating pulse wave analysis data at each frequency region; and
a determination is made that arrhythmia has occurred when an anomalous portion is detected by analyzing the continuity of said pulse wave analysis data in each frequency region.

14. An arrhythmia detecting apparatus according to claim 13, wherein said arrhythmia detecting means has a frequency correcting means which carries out correction of said pulse wave analysis data based on each of the corresponding frequencies, so that the power density per frequency becomes constant, and generates corrected pulse wave data; wherein, a determination is made that arrhythmia has occurred when an anomalous portion is detected by analysis of the continuity of said corrected pulse wave data in each frequency region.

15. An arrhythmia detecting apparatus according to claim 13, further comprising body motion detecting means which detects the motion of the body and outputs a body motion waveform; wherein,
said arrhythmia detecting means is provided with said wavelet transforming means as said first wavelet transforming means, and a second wavelet transforming means which carries out wavelet transformation to said body motion pulse wave detected by said body motion detecting means, and generates body motion analysis data at each frequency region;
said body motion component excluding means has a mask means which subtracts said body motion analysis data from said pulse wave analysis data and generates pulse wave analysis data from which body motion has been removed; and
said arrhythmia detecting means determines that arrhythmia has occurred when an anomalous portion is detected by analyzing the continuity of said pulse wave analysis data generated by said mask means in each frequency region.

16. An arrhythmia detecting apparatus according to claim 13, further comprising:
body motion detecting means which detects the motion of the body and outputs a body motion waveform; and wherein said arrhythmia detecting means includes:
  said wavelet transforming means as a first wavelet transforming means;
  a frequency correcting means which carries out correction of the pulse wave analysis data based on each of the corresponding frequencies, so that the power density per frequency becomes constant;
  a second wavelet transforming means which carries out wavelet transformation to the body motion waveform detected by said body motion detecting means, and generates body motion analysis data for each frequency region;
  a second frequency correcting means which carries out correction of said body motion analysis data based on each of the corresponding frequencies, so that the power density per frequency becomes constant, and generates corrected body motion data; and
  said body motion component excluding means has a mask means which subtracts said corrected body motion data from said corrected pulse wave data, and generates corrected pulse wave data from which body motion has been excluded;
  said arrhythmia detecting means determining that arrhythmia has occurred when an anomalous portion is detected by analyzing the continuity of said corrected pulse wave data generated by said mask means in each frequency region.

17. An arrhythmia detecting apparatus according to claim 13, further comprising:
  body motion detecting means which detects the motion of the body and outputs a body motion waveform; wherein,
    said arrhythmia detecting means includes said wavelet transforming means as a first wavelet transforming means, and a second wavelet transforming means which carries out wavelet transformation of the body motion waveform detected by said body motion detecting means, and generates body motion analysis data in each frequency region;
    said body motion component excluding means has a mask means which subtracts said body motion analysis data from said pulse wave analysis data and generates at each frequency region pulse wave data from which body motion has been excluded; and
    said arrhythmia detecting means has a frequency correcting means which carries out correction of said pulse wave data based on each of the corresponding frequencies, so that the power density per frequency becomes constant, and generates corrected pulse wave data;
  said arrhythmia detecting means making a determination that arrhythmia has occurred when an anomalous portion is detected by analyzing the continuity of said corrected pulse wave data generated by said mask means at each frequency region.

18. An arrhythmia detecting apparatus according to claim 13, further comprising:
  body motion detecting means which detects the motion of the body and outputs a body motion waveform; wherein,
    said body motion component excluding means generates pulse wave data after excluding frequency components corresponding to body motion from among the pulse wave analysis data; and
    said arrhythmia detecting means determines that arrhythmia has occurred when an anomalous portion is detected by analyzing the continuity of the pulse wave data in each frequency region.

19. An arrhythmia detecting apparatus according to claim 13, further comprising:
  body motion detecting means which detects the motion of the body and outputs a body motion waveform; wherein,
    said arrhythmia detecting means includes a frequency correcting means which carries out correction of the pulse wave analysis data based on each of the corresponding frequencies, so that the power density per frequency becomes constant, and generates corrected pulse wave data;
    said body motion component excluding means generates pulse wave data after excluding frequency components corresponding to body motion from among said corrected pulse wave data; and
    said arrhythmia detecting means makes a determination that arrhythmia has occurred when an anomalous portion is detected by analyzing the continuity of the pulse wave data in each frequency region.

20. An arrhythmia detecting apparatus according to claim 13, wherein said arrhythmia detecting means includes:
  a pulse wave period detecting means which detects the period of the pulse waveform; and wherein
  said wavelet transforming means carries out wavelet transformation in synchronization with said detected period.

21. An arrhythmia detecting apparatus according to claim 15 wherein:
  said arrhythmia detecting means includes a pulse wave period detecting means which detects the period of said pulse waveform; and
  said first wavelet transforming means and said second wavelet transforming means carry out wavelet transformation in synchronization with said detected period.

22. An arrhythmia detecting apparatus according to claim 3 further comprising a recording means which records the time at which an arrhythmia event is detected by said arrhythmia detecting means.

23. An arrhythmia detecting apparatus according to claim 22, wherein notice is provided of information which has been related to the arrhythmia event time stored in said recording means.

24. An arrhythmia detecting apparatus according to claim 22, wherein notice is provided after associating information related to an arrhythmia event time stored in said recording means with physiological rhythms in the body, and rendering said information into a graph.

25. An arrhythmia detecting apparatus according to claim 3 further comprising a frequency calculating means which calculates the number of times that a determination of arrhythmia is made by said arrhythmia detecting means during a prespecified period of time, as arrhythmia frequency information.

26. An arrhythmia detecting apparatus according to claim 25, further comprising a second notifying means which provides notice when said arrhythmia frequency information exceeds a specific value determined in advance.

27. An arrhythmia detecting apparatus according to claim 3 further comprising a summing means which sums the number of times that an arrhythmia determination was made by said arrhythmia detecting means, and generates arrhythmia sum information.

28. An arrhythmia detecting apparatus according to claim 27, further comprising a third notifying means which provides notice when said arrhythmia sum information exceeds a specific value determined in advance.

29. An arrhythmia detecting apparatus according to claim 3 further comprising:
a frequency calculating means which calculates the number of times that a determination of arrhythmia is made by said arrhythmia detecting means during a specific period of time, as arrhythmia frequency information; and
a summing means which sums the number of times that an arrhythmia determination was made by said arrhythmia detecting means, and generates arrhythmia sum information.

30. An arrhythmia detecting apparatus according to claim 3 further comprising:
a frequency calculating means which calculates the number of times that a determination of arrhythmia is made by said arrhythmia detecting means during a specific period of time, as arrhythmia frequency information; and
a summing means which sums the number of times that an arrhythmia determination was made by said arrhythmia detecting means, and generates arrhythmia sum information; and
a fourth notifying means which provides notice when both said arrhythmia frequency information and said arrhythmia sum information exceed the respective specific values determined in advance therefor.

31. An arrhythmia detecting apparatus according to claim 25, wherein notice is provided of said arrhythmia frequency information.

32. An arrhythmia detecting apparatus according to claim 27, wherein notice is provided of said sum information.

33. An arrhythmia detecting apparatus according to claim 29, wherein notice is provided of said arrhythmia frequency information and said sum information.

34. An arrhythmia detecting apparatus according to claim 3, wherein arrhythmia detecting processing and various notice processing may be carried out in parallel by the arrhythmia detecting means.

35. An arrhythmia detecting apparatus according to claim 1, wherein said pulse wave detecting means comprises a pressure pulse wave sensor which uses pressure to detect the arterial pulse in the body.

36. An arrhythmia detecting apparatus according to claim 1, wherein said pulse wave detecting means receives reflected light obtained when the detection site on the body is irradiated with light having a wavelength of 300 to 700 nm, and detects the received light signal as a pulse waveform.

37. An arrhythmia detecting apparatus according to claim 1, wherein said pulse wave detecting means receives transmitted light obtained when the detection site on the body is irradiated with light having a wavelength of 600 to 1000 nm, and detects the received light signal as the pulse waveform.

* * * * *